(12) United States Patent
Pinchasi et al.

(10) Patent No.: US 7,560,100 B2
(45) Date of Patent: Jul. 14, 2009

(54) MIXTURES OF POLYPEPTIDES, COMPOSITIONS CONTAINING AND PROCESSES FOR PREPARING SAME, FOR TREATING NEURODEGENERATIVE DISEASES

(75) Inventors: Irit Pinchasi, Ra'anana (IL); Ben-Zion Dolitzky, Petach-Tikva (IL); Anton Frenkel, Modiin (IL); Michal Schwartz, Rehovot (IL); Ruth Arnon, Rehovot (IL); Rina Aharoni, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 11/223,408

(22) Filed: Sep. 9, 2005

(65) Prior Publication Data
US 2006/0122113 A1    Jun. 8, 2006

Related U.S. Application Data

(60) Provisional application No. 60/608,844, filed on Sep. 9, 2004.

(51) Int. Cl.
*A61K 31/74* (2006.01)
(52) U.S. Cl. .................... 424/78.17; 424/78.37
(58) Field of Classification Search .............. None
See application file for complete search history.

(56) References Cited

U.S. PATENT DOCUMENTS

| | | | |
|---|---|---|---|
| 3,849,550 A | 11/1974 | Teitelbaum et al. | |
| 4,594,409 A | 6/1986 | Hayashi et al. | |
| 5,639,726 A * | 6/1997 | Lawrence et al. | 514/12 |
| 5,668,117 A * | 9/1997 | Shapiro | 514/55 |
| 5,800,808 A | 9/1998 | Konfino et al. | |
| 5,858,964 A | 1/1999 | Aharoni et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,214,791 B1 * | 4/2001 | Arnon et al. | 514/2 |

(Continued)

FOREIGN PATENT DOCUMENTS

DE    3930733    3/1991

(Continued)

OTHER PUBLICATIONS

U.S. Appl. No. 11/373,794, filed Mar. 9, 2006, Pinchasi et al.

(Continued)

*Primary Examiner*—Jeffrey E Russel
(74) *Attorney, Agent, or Firm*—John P. White; Cooper & Dunham LLP

(57) ABSTRACT

The invention provides a composition comprising a mixture of polypeptides, wherein each polypeptide (a) is a copolymer of the amino acids L-glutamic acid, L-alanine, L-tyrosine, and L-lysine, and (b) may be in the form of a pharmaceutically acceptable salt; and wherein in the mixture (i) the polypeptides have an average molecular weight in the range 13,500 to 18,500 daltons, (ii) 13% to 38% of the polypeptides have a diethylamide group instead of a carboxyl group present at one end thereof, and (iii) 68% of the polypeptides have a molecular weight between 7,000 and 41,000 daltons. In an embodiment, the average molecular weight is 16,000 daltons. The invention also provides a method of treating a human subject afflicted with a neurodegenerative disease comprising administering to the human subject a therapeutically effective amount of any of the disclosed compositions so as to thereby treat the human subject.

43 Claims, 31 Drawing Sheets

U.S. PATENT DOCUMENTS

| | | |
|---|---|---|
| 6,342,476 B1 | 1/2002 | Konfino et al. |
| 6,362,161 B1 | 3/2002 | Konfino et al. |
| 6,514,938 B1 | 2/2003 | Gad et al. |
| 6,620,847 B2 | 9/2003 | Konfino et al. |
| 6,800,285 B2 | 10/2004 | Rodriguez et al. |
| 6,800,287 B2 | 10/2004 | Gad et al. |
| 6,844,314 B2 | 1/2005 | Eisenbach-Schwartz et al. |
| 6,939,539 B2 | 9/2005 | Konfino et al. |
| 7,022,663 B2 | 4/2006 | Gilbert et al. |
| 7,033,582 B2 | 4/2006 | Yong et al. |
| 7,074,580 B2 | 7/2006 | Gad et al. |
| 7,163,802 B2 | 1/2007 | Gad et al. |
| 7,199,098 B2 | 4/2007 | Konfino et al. |
| 7,279,172 B2 | 10/2007 | Aharoni et al. |
| 7,407,936 B2 | 8/2008 | Eisenbach-Schwartz et al. |
| 2002/0055466 A1 | 5/2002 | Aharoni et al. |
| 2002/0077278 A1 | 6/2002 | Yong et al. |
| 2003/0170729 A1 | 9/2003 | Klinger |
| 2004/0006022 A1 | 1/2004 | Strominger et al. |
| 2005/0019322 A1 | 1/2005 | Rodriguez et al. |
| 2005/0170004 A1 | 8/2005 | Rosenberger et al. |
| 2005/0171286 A1 | 8/2005 | Konfino et al. |
| 2006/0052586 A1 | 3/2006 | Dolitzky |
| 2006/0172942 A1 | 8/2006 | Dolitzky |
| 2006/0264354 A1 | 11/2006 | Aharoni et al. |
| 2007/0021324 A1 | 1/2007 | Dolitzky |
| 2007/0021341 A1 | 1/2007 | Sela et al. |
| 2007/0037740 A1 | 2/2007 | Pinchasi et al. |
| 2007/0048794 A1 | 3/2007 | Gad et al. |
| 2007/0054857 A1 | 3/2007 | Pinchasi et al. |
| 2007/0059798 A1 | 3/2007 | Gad et al. |
| 2007/0161566 A1 | 7/2007 | Pinchasi |
| 2007/0173442 A1 | 7/2007 | Vollmer |

FOREIGN PATENT DOCUMENTS

| | | |
|---|---|---|
| EP | 0378246 | 6/1990 |
| RU | 1690368 | 8/1990 |
| RU | 1469826 | 11/1995 |
| SU | 1182051 | 7/1985 |
| SU | 1664845 | 7/1991 |
| WO | WO 98/30227 | 7/1998 |
| WO | WO 00/05250 | 2/2000 |
| WO | WO 00/18794 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2004/043995 | 5/2004 |
| WO | WO 2005/041933 | 5/2005 |
| WO | WO 2006/050122 | 5/2006 |
| WO | WO 2008/006026 | 1/2008 |

OTHER PUBLICATIONS

Aharoni, R., "Copolymer 1 inhibits manifestations of graft rejection," *Transplantation*, Aug. 2001, 72(4), 598-605.
Bodanszky, M., "Principles of Peptide Synthesis," Springer-Verlag, Berlin, Heidelberg, New York, Tokyo, 1984. 118-229.
Bornstein, *Hosp. Pract. (Off. Ed.)*, May 15, 1992, vol. 27 (No. 5) L135-138, 141-142, 145-158.
Bornstein, "Cop 1 May be Beneficial for Patients with Exacerbating-remitting Form of Multiple Sclerosis", *Adv. Ther.(USA)*, 1987, 4, 206 (Abstract).
Bornstein, et al., "A Pilot Trial of Cop 1 in Exacerbating-remitting Multiple Sclerosis", *New Eng. J. Med.*, 1987, 317(7), 408-414.
Bornstein, et al., "A Placebo-controlled, Double-blind, Randomized Two-center, Pilot Trial of Cop 1 in Chronic Progressive Multiple Sclerosis", *Neurol.*, 1991, 41, 533-539.
Bornstein, et al., "Clinical Experience with COP-1 in Multiple Sclerosis", *Neurol.*, 1988, 38(Suppl. 2), 66-69.
Bornstein, et al., "Rationale for Immunomodulating Therapies of Multiple Sclerosis", *Neurology*, 1988 38(Suppl 2) 80-81.
Bornstein, et al., "Clinical Trials of a Synthetic Polypeptide (Colpolymer 1) for the Treatment of Multiple Sclerosis" in Gonsett et al., *Immunological and Clinical Aspects of Multiple Sclerosis* (MTP Press, The Hague, 1984) 144-150.
Bornstein, et al., "Clinical Trials of Cop 1 in Multiple Sclerosis" in *Handbook of Multiple Sclerosis* (S.D. Cook Marcel Rekker, ed., 1990) 469-480.
Bornstein, et al., "Clinical Trials of Copolymer 1 in Multiple Sclerosis", *Ann. N.Y. Acad. Sci.* (USA), 1984, 366-372.
Bornstein, et al., "Multiple Sclerosis: Clinical Trials of a Synthetic Polypeptide, Copolymer 1", *Neurol.*, 1985, 35 (Suppl. I), 103 (Abstract).
Bornstein, et al., "Multiple Sclerosis: Trial of a Synthetic Polypeptide", *Ann. Neurol.*, 1982, 11, 317-319.
Bornstein, et al., "Pilot Trial of COP-1 in Chronic Progressive Multiple Sclerosis: Preliminary Report", from *The International Multiple Sclerosis Conference: An Update on Multiple Sclerosis*, Roma (Italy), Sep. 15-17, 1988, in *Elsevier Science Publisher*, 1989, 225-232.
Bornstein, et al., "Treatment of Multiple Sclerosis with a Synthetic Polypeptide: Preliminary Results", *Ann. Neurol.*, 1980, 8, 117 (Abstract).
Bornstein, et al., "Treatment of Multiple Sclerosis with a Synthetic Polypeptide: Preliminary Results", *Trans. Am. Neurol. Assoc.*, 1980, 105, 348-350.
Bornstein, et al., "Treatment of Multiple Sclerosis with Copolymer 1" in *Treatment of Multiple Sclerosis: Trial Design, Results and Future Perspectives* (Rudick R.A. & Goodkin D.E., eds., Springer Verlag, London, 1992) 173-198.
Korczyn et al., "Safety profile of copolymer 1: Analysis of cumulative experience in the United States and Israel," *J. Neurol.*, Apr. 1996; 243 (4 Suppl 1) pp. S23-S26.
Teitelbaum D., Copolymer 1 induces T cells of the T helper type 2 that crossreact with myelin basic protein and suppress experimental autoimmune encephalomyelitis, *Proc. Natl. Acad. Sci. U.S.A.*, Sep. 1997, 94(20), 10821-10826.
U.S. Appl. No. 10/543,764, filed Jul. 18, 2005, Aharoni et al.
U.S. Appl. No. 11/516,860, filed Sep. 9, 2006, Gad et al.
Aharoni, R., "Copolymer 1 inhibits manifestations of graft rejection," *Transplantation*, Aug. 2001, 72(4), 598-605.
U.S. Appl. No. 09/359,099, filed Jul. 22, 1999, Strominger, et al.
U.S. Appl. No. 10/228,850, filed Sep. 14, 2005, Schwartz, et al.
U.S. Appl. No. 10/577,588, filed Apr. 27, 2006, Rosenberger, et al.
U.S. Appl. No. 10/591,195, filed Aug. 30, 2006, Hayardeny, et al.
U.S. Appl. No. 11/373,794, filed Mar. 9, 2006, Pinchasi.
U.S. Appl. No. 11/590,338, filed Oct. 30, 2006, Pinchasi.
U.S. Appl. No. 11/654,374, filed Jan. 16, 2007, Schwartz, et al.
U.S. Appl. No. 11/661,060, filed Feb. 22, 2007, Schipper, et al.
U.S. Appl. No. 11/811,684, filed Jun. 12, 2007, Frenkel, et al.
U.S. Appl. No. 11/823,780, filed Jun. 27, 2007, Pinchasi.
U.S. Appl. No. 11/884,633, Kreitman, et al.
PCT International Preliminary Report on Patentability issued Mar. 22, 2007 for International Application No. PCT/US05/032553.
PCT International Search Report issued Jun. 6, 2006 for International Application No. PCT/US05/032553.
PCT Written Opinion issued Jun. 6, 2006 for International Application No. PCT/US05/032553.
U.S. Appl. No. 12/284,041, filed Sep. 18, 2008, Pinchasi et al.
Copaxone® in *Physician's Desk Reference*, Medical Economics Co., Inc., Montvale, NJ, 2003, 3115-3118, (Exhibit 4).
Copaxone® (glatiramer acetate injection), prescribing information [package insert], Teva Neuroscience Inc; May, 2007, www.copaxone.com/ pdf/ PrescribingInformation.pdf, (Exhibit 5).

* cited by examiner

IL-2

IFN-γ

IL-10

\* p < 0.01 (RGC count in test group vs. negative control group)

IL-2

IFN-γ

IL-10

IL-4

* p < 0.05;  ** p < 0.01 (RGC count in test group vs. vehicle control group)

TV-A = the polypeptide mixture of the invention
TV-B = glatiramer acetate

TV-A= The Polypeptide Mixture of the Invention

* p < 0.05; ** p < 0.01 (RGC count in test group vs. vehicle control group)

monthly p = 1.64x10$^{-9}$;  weekly p = 1.29x10$^{-15}$ (RGC count in test group vs. vehicle control group)

━━━ Sample: PP Marker 1/Guanidine 4.5M
━━━ Sample: PP Marker 2/Guanidine 4.5M
━━━ Sample: PP Marker 3/Guanidine 4.5M
       Sample: PP Marker 4/Guanidine 4.5M
━━━ Sample: PP Marker 5/Guanidine 4.5M ———— Sample: PP Marker 1/Guanidine 4.5M
———— Sample: PP Marker 2/Guanidine 4.5M
———— Sample: PP Marker 3/Guanidine 4.5M
............ Sample: PP Marker 4/Guanidine 4.5M
———— Sample: PP Marker 5/Guanidine 4.5M
———— Sample: PP Mixture of the Invention Linear Parameters

| Markers Set | Slope | Intercept | R2 |
|---|---|---|---|
| Polypeptide Markers 1-5 (A) | -0.188 | 1.542 | 0.992 |
| Glatiramer Acetate Markers (B) | -0.284 | 1.935 | 0.997 |
| Protein Markers (sigma) (C) | -0.218 | 1.698 | 0.960 |
| Protein Markers (Amersham) (D) | -0.232 | 1.785 | 0.990 |

SEQUENCE LISTING

<160> NUMBER OF SEQ ID NOS: 10

<210> SEQ ID NO 1
<211> LENGTH: 149
<212> TYPE: PRT
<213> ORGANISM: Artificial Sequence
<220> FEATURE:
<223> OTHER INFORMATION: Molecular weight marker

<400> SEQUENCE: 1

```
Ala Glu Lys Tyr Lys Ala Lys Lys Ala Lys Glu Lys Ala Tyr Lys Lys
1               5                   10                  15

Lys Ala Lys Glu Ala Lys Lys Ala Lys Tyr Lys Ala Lys Glu Ala Lys
                20                  25                  30

Ala Tyr Lys Ala Glu Lys Lys Ala Lys Tyr Ala Lys Ala Lys Glu Lys
                35                  40                  45

Ala Tyr Ala Lys Ala Lys Glu Ala Lys Ala Tyr Ala Lys Ala Lys Ala
                50                  55                  60

Lys Ala Glu Lys Ala Lys Ala Lys Ala Lys Tyr Ala Glu Lys Ala Lys
65                  70                  75                  80

Ala Ala Lys Tyr Ala Glu Lys Ala Ala Lys Tyr Ala Glu Ala Lys Ala
                85                  90                  95

Lys Ala Ala Glu Ala Lys Tyr Ala Ala Glu Ala Lys Glu Ala Ala Lys
                100                 105                 110

Ala Ala Glu Ala Lys Tyr Ala Ala Lys Ala Glu Ala Ala Lys Tyr Ala
                115                 120                 125

Ala Glu Lys Ala Ala Glu Lys Tyr Ala Lys Ala Glu Ala Ala Ala Glu
                130                 135                 140

Ala Lys Glu Ala Ala
145
```

<210> SEQ ID NO 2
<211> LENGTH: 169
<212> TYPE: PRT
<213> ORGANISM: Artificial Sequence
<220> FEATURE:
<223> OTHER INFORMATION: Molecular weight marker

<400> SEQUENCE: 2

```
Ala Lys Lys Lys Tyr Lys Ala Lys Glu Lys Ala Lys Lys Lys Lys Ala
1               5                   10                  15

Lys Glu Lys Lys Tyr Lys Ala Lys Lys Ala Lys Tyr Lys Glu Lys Ala
                20                  25                  30

Ala Lys Tyr Lys Ala Lys Lys Ala Lys Ala Tyr Lys Ala Lys Lys Ala
                35                  40                  45

Glu Lys Ala Lys Ala Lys Ala Glu Lys Ala Lys Ala Tyr Ala Glu Lys
                50                  55                  60

Ala Lys Ala Lys Tyr Ala Lys Glu Ala Lys Lys Tyr Ala Glu Lys Ala
65                  70                  75                  80

Lys Lys Ala Glu Tyr Lys Ala Lys Glu Ala Ala Glu Lys Ala Lys Ala
                85                  90                  95

Tyr Ala Lys Glu Ala Ala Lys Ala Glu Lys Ala Ala Lys Ala Ala Glu
                100                 105                 110

Lys Ala Ala Lys Ala Tyr Ala Lys Ala Glu Ala Ala Lys Glu Ala
                115                 120                 125
```

Ala Tyr Ala Ala Lys Ala Glu Ala Lys Ala Tyr Ala Glu Ala
            130                 135                 140

Ala Lys Ala Glu Tyr Ala Ala Glu Ala Ala Lys Gly Ala Ala Tyr Ala
145                 150                 155                 160

Ala Ala Glu Tyr Ala Ala Glu Ala Ala
                165

<210> SEQ ID NO 3
<211> LENGTH: 190
<212> TYPE: PRT
<213> ORGANISM: Artificial Sequence
<220> FEATURE:
<223> OTHER INFORMATION: Molecular weight marker

<400> SEQUENCE: 3

Ala Lys Lys Lys Tyr Lys Ala Lys Glu Lys Ala Lys Lys Lys Ala
1               5                   10                  15

Lys Glu Lys Lys Lys Tyr Lys Ala Lys Glu Lys Ala Lys Lys Tyr
                20                  25                  30

Lys Glu Lys Ala Ala Lys Tyr Lys Ala Lys Lys Ala Lys Lys Glu Ala
            35                  40                  45

Ala Lys Tyr Lys Lys Ala Lys Ala Glu Lys Ala Lys Tyr Ala Lys Glu
    50                  55                  60

Lys Ala Glu Lys Ala Lys Ala Tyr Ala Glu Lys Ala Lys Ala Lys Tyr
65                  70                  75                  80

Ala Lys Glu Ala Lys Lys Tyr Ala Glu Lys Ala Lys Ala Lys Glu Tyr
                85                  90                  95

Lys Ala Lys Glu Ala Ala Glu Lys Ala Lys Tyr Ala Lys Glu Ala
            100                 105                 110

Ala Lys Ala Glu Ala Lys Ala Lys Tyr Ala Ala Glu Lys Ala Ala
        115                 120                 125

Glu Ala Ala Lys Ala Ala Tyr Ala Lys Ala Glu Ala Ala Lys Ala Ala
    130                 135                 140

Lys Glu Ala Ala Tyr Ala Ala Lys Ala Glu Ala Ala Lys Ala Ala Tyr
145                 150                 155                 160

Ala Ala Glu Ala Ala Lys Ala Glu Tyr Ala Ala Glu Ala Ala Lys Glu
                165                 170                 175

Ala Ala Tyr Ala Ala Ala Glu Tyr Ala Ala Ala Glu Ala Ala
            180                 185                 190

<210> SEQ ID NO 4
<211> LENGTH: 221
<212> TYPE: PRT
<213> ORGANISM: Artificial Sequence
<220> FEATURE:
<223> OTHER INFORMATION: Molecular weight marker

<400> SEQUENCE: 4

Ala Lys Lys Lys Tyr Lys Ala Lys Glu Lys Ala Lys Ala Lys Lys
1               5                   10                  15

Lys Ala Lys Glu Lys Lys Lys Tyr Lys Ala Lys Glu Lys Lys Ala
                20                  25                  30

Lys Lys Tyr Lys Glu Lys Ala Ala Lys Tyr Ala Lys Lys Glu Lys
            35                  40                  45

Ala Lys Lys Glu Ala Lys Tyr Lys Lys Ala Lys Lys Tyr Lys Ala
        50                  55                  60

Glu Lys Ala Lys Tyr Ala Lys Glu Lys Ala Lys Glu Lys Ala Lys Ala
65                  70                  75                  80

Tyr Ala Glu Lys Ala Glu Lys Ala Ala Lys Tyr Ala Ala Lys Glu Ala
            85                  90                  95

Lys Lys Tyr Ala Glu Lys Ala Ala Glu Lys Lys Ala Glu Tyr Lys Ala
            100                 105                 110

Lys Glu Ala Ala Glu Lys Tyr Ala Ala Lys Ala Tyr Ala Ala Lys Glu
            115                 120                 125

Ala Ala Lys Ala Tyr Lys Glu Ala Lys Ala Ala Lys Tyr Ala Lys Ala
            130                 135             140

Ala Glu Lys Ala Ala Lys Glu Ala Ala Lys Ala Ala Tyr Ala Ala
145                 150                 155                 160

Lys Ala Glu Ala Ala Lys Glu Ala Ala Lys Ala Ala Tyr Ala Ala
                165                 170                 175

Ala Lys Ala Glu Ala Ala Ala Lys Ala Ala Ala Tyr Ala Ala Glu
                180                 185                 190

Ala Ala Ala Lys Ala Glu Tyr Ala Ala Glu Ala Ala Lys Glu Ala
                195                 200                 205

Ala Tyr Ala Ala Ala Glu Tyr Ala Ala Ala Glu Ala Ala
            210                 215                 220

<210> SEQ ID NO 5
<211> LENGTH: 249
<212> TYPE: PRT
<213> ORGANISM: Artificial Sequence
<220> FEATURE:
<223> OTHER INFORMATION: Molecular weight marker

<400> SEQUENCE: 5

Ala Lys Lys Lys Tyr Lys Ala Lys Glu Lys Lys Ala Lys Tyr Lys Ala
1               5                   10                  15

Lys Lys Glu Lys Lys Ala Lys Glu Lys Lys Ala Lys Lys Lys Tyr Lys
                20                  25                  30

Ala Lys Lys Lys Ala Ala Glu Lys Lys Tyr Ala Lys Glu Lys Lys Ala
            35                  40                  45

Lys Glu Lys Ala Ala Lys Lys Tyr Lys Ala Lys Lys Glu Lys Ala Lys
        50                  55                  60

Lys Glu Ala Ala Lys Tyr Lys Lys Ala Lys Lys Tyr Lys Ala Glu Lys
65                  70                  75                  80

Lys Ala Lys Tyr Ala Ala Lys Glu Lys Ala Lys Glu Lys Ala Lys Ala
                85                  90                  95

Tyr Ala Glu Lys Lys Ala Glu Lys Ala Ala Lys Tyr Ala Ala Lys Glu
            100                 105                 110

Ala Lys Lys Tyr Ala Glu Lys Ala Ala Glu Lys Lys Ala Glu Tyr Lys
            115                 120                 125

Ala Lys Glu Ala Ala Glu Lys Tyr Ala Ala Lys Ala Lys Glu Tyr Ala
            130                 135                 140

Ala Glu Lys Glu Ala Ala Lys Ala Tyr Lys Glu Ala Lys Ala Ala Lys
145                 150                 155                 160

Tyr Ala Lys Ala Ala Glu Lys Ala Ala Lys Glu Ala Ala Lys
                165                 170                 175

Ala Ala Tyr Ala Ala Lys Ala Glu Ala Ala Lys Glu Ala Ala Lys Glu
            180                 185                 190

Ala Ala Tyr Ala Ala Lys Ala Glu Ala Ala Tyr Ala Ala Ala
            195                 200                 205

Lys Ala Ala Ala Ala Tyr Ala Ala Glu Ala Ala Ala Lys Ala Glu Tyr
210                 215                 220

-continued

```
Ala Ala Ala Glu Ala Ala Ala Lys Glu Ala Tyr Ala Ala Glu
225                 230                 235                 240

Tyr Ala Ala Ala Ala Glu Ala Ala Ala
                245

<210> SEQ ID NO 6
<211> LENGTH: 453
<212> TYPE: DNA
<213> ORGANISM: Artificial Sequence
<220> FEATURE:
<223> OTHER INFORMATION: Molecular weight marker

<400> SEQUENCE: 6
atggccgaga atacaaggc taagaaagcg aaggaaaaag catacaagaa aaaggccaaa        60
gaagcaaaaa aggcaaaata taaggctaaa gaagcgaaag cgtataaagc agaaaaaaag      120
gcgaaatatg caaaagcaaa agaaaaggct tatgctaaag ccaaggaggc aaaagcatac      180
gcgaaagcca agcaaaagc cgaaaaggct aaagctaaag cgaaatatgc tgagaaagct      240
aaagccgcga gtatgccga aaaagcggcc aaatatgcgg aagccaaagc aaaggccgct      300
gaggcaaaat atgccgcaga agctaaagaa gctgcgaaag ccgcggaagc aaaatacgcg      360
gcaaaggcag aagcggccaa atatgccgcg gagaaggccg cggaaaagta tgcgaaagct      420
gaagccgcgg ccgaggcgaa agaggcggcg taa                                  453

<210> SEQ ID NO 7
<211> LENGTH: 513
<212> TYPE: DNA
<213> ORGANISM: Artificial Sequence
<220> FEATURE:
<223> OTHER INFORMATION: Molecular weight marker

<400> SEQUENCE: 7
atggcaaaga gaaatataa ggcgaaagaa aagaaggcta agaagaaagc aaaagagaag       60
aagtacaaag ccaagaaggc gaaatacaaa gaaaaggcgg caaagtataa ggctaaaaag      120
gcgaaagcta atacaaagc caaagccgag aaagcgaaag ctaaagcaga aaaagcgaaa      180
gcttatgcgg aaaagcgaa agcaaaatat gcgaaagaag ccaaaaagta tgcggagaaa      240
gcaaaaaaag ctgagtataa agctaaagaa gccgcagaaa aagctaaagc ttatgccaaa      300
gaggctgcaa aagcagaaaa agctgcgaaa gcagcggaaa aagccgctaa ggcttatgcg      360
aaagcggaag ccgcagccaa agaagctgcc tacgccgcga aagcagaagc taaagcggcc      420
tatgccgcag aggcagccaa agcggaatac gcggctgaag cggcaaaaga ggcggcttac      480
gcagccgcgg aatacgcggc cgaggcggcc taa                                  513

<210> SEQ ID NO 8
<211> LENGTH: 576
<212> TYPE: DNA
<213> ORGANISM: Artificial Sequence
<220> FEATURE:
<223> OTHER INFORMATION: Molecular weight marker

<400> SEQUENCE: 8
atggcaaaga gaaatataa ggcgaaagaa aagaaggcta agaagaaagc aaaagagaag       60
aagaaataca agccaagga aagaaagcc aaaaagtaca agaaaaggc ggcaaagtat      120 aaggctaaaa aggcgaaaaa ggaagcggct aaatacaaaa aggccaaagc cgagaaagcg      180
aaatatgcga aggaaaaagc agaaaaagcg aaagcttatg cggaaaaagc gaaagcaaaa      240
tatgcgaaag aagccaaaaa gtatgcggag aaagcaaaaa agctgagta taaagctaaa      300
```

```
gaagccgcag aaaaagctaa agcttatgcc aaagaggctg caaaagcaga agccaaagct    360
gcgaaatatg cagcggaaaa agccgctgag gctgccaaag cagcctatgc gaaagcggaa    420
gccgcaaaag cagccaaaga agctgcctac gccgcgaaag cagaagctgc caaagcggcc    480
tatgccgcag aggcagccaa agcggaatac gcggctgaag cggcaaaaga ggcggcttac    540
gcagccgcgg aatacgcggc cgcggaggcc gcgtaa                              576
```

<210> SEQ ID NO 9
<211> LENGTH: 669
<212> TYPE: DNA
<213> ORGANISM: Artificial Sequence
<220> FEATURE:
<223> OTHER INFORMATION: Molecular weight marker

<400> SEQUENCE: 9

```
atggcaaaga gaaatataa ggcgaaagaa aagaaggcta aggctaagaa gaaagcaaaa     60
gagaagaaga aatacaaagc caagaaagaa aagaaagcca aaagtacaa agaaaaggcg    120 gcaaagtata aggctaaaaa ggagaaagcg aaaaaggaag cggctaaata caaaaaggcc    180
aaaaagtaca agccgagaa agcgaaatat gcgaaggaaa agcaaaaga aaagcgaaa     240 gcttatgcgg aaaaagcgga gaaagctgca aaatatgcgg ccaaagaagc caaaaagtat    300
gcggagaaag cagctgagaa aaaagctgag tataaagcta agaagccgc agaaaaatac    360 gcggctaaag cttatgccgc taagaggct gcaaaagcat ataaggaagc caaagctgcg    420
aaatatgcga agctgcgga aaaagccgct gcgaaagagg ctgccaaagc agcctatgcg    480
gccaaagcgg aagccgcaaa agaggcagcc aaagaagctg cctacgccgc ggcaaaagca    540
gaagctgccg ctgcgaaagc ggctgcctat gccgcagagg cagccgctaa agcggaatac    600
gcggctgaag cggcagcgaa agaggcggct tacgcagccg cggaatacgc ggccgcggag    660
gccgcgtaa                                                            669
```

<210> SEQ ID NO 10
<211> LENGTH: 753
<212> TYPE: DNA
<213> ORGANISM: Artificial Sequence
<220> FEATURE:
<223> OTHER INFORMATION: Molecular weight marker

<400> SEQUENCE: 10

```
atggcgaaaa aaagtacaa agctaaggag aaaaaggcga atataaggc aaagaaggag      60 aaaaaggcga agaaaagaa ggctaagaag aaatataaag cgaagaagaa agccgctgag    120
aagaaatacg ccaaagagaa aaaggcgaaa gaaaaggcgg caagaaata aggctaaa     180 aaggagaaag cgaaaaagga agcggctaaa tacaaaaagg ccaaaaagta caaagccgag    240
aaaaaggcga atatgcggc caaggaaaaa gcaaagaaa agcgaaagc ttatgcggaa     300 aaaaaggcgg agaaagctgc aaaatatgcg ccaaagaag ccaaaaagta tgcggagaaa    360
gcagctgaga aaaagctga gtataaagct aagaagccg cagaaaaata cgcggctaaa    420
aaggccgagt atgccgctga aaagaggct gcaaaagcat ataaggaagc caaagctgcg    480
aaatatgcga agctgcgga aaaagccaaa gctgcgaaag aggctgccaa agcagcctat    540
gcggccaaag cggaagccgc aaaagaggca gccaaagaag ctgcctacgc cgcggcaaaa    600
gcagaagctg ccgcttatgc agcggccaaa gcggcggctg cctatgccgc agaggcagcc    660
```

-continued

```
gctaaagcgg aatacgcggc tgcagaagcg gcagcgaaag aggcggctta cgcagccgcg    720
gaatacgcgg ccgcggccga ggcggctgca taa                                 753
```

MIXTURES OF POLYPEPTIDES, COMPOSITIONS CONTAINING AND PROCESSES FOR PREPARING SAME, FOR TREATING NEURODEGENERATIVE DISEASES

This application claims benefit of U.S. Provisional Application No. 60/608,844, filed Sep. 9, 2004, the contents of which are hereby incorporated herein by reference.

Throughout this application various patent and nonpatent publications are referenced, full citations of which are provided. The disclosures of these publications in their entireties are hereby incorporated by reference into this application in order to more fully describe the state of the art to which this invention pertains.

BACKGROUND OF THE INVENTION

Copolymers of L-glutamic acid, L-alanine, L-tyrosine, and L-lysine and mixtures thereof have long been known. (U.S. Pat. No. 3,849,550, issued Nov. 19, 1974 (Teitelbaum, et al.))

Over the last two decades such copolymer mixtures have been extensively studied, and numerous modifications as well as potential uses have been identified. As a result of these efforts, a commercial product, COPAXONE®, was developed which is now marketed.

Specifically, COPAXONE® is the brand name for a pharmaceutical composition which contains glatiramer acetate (GA) as the active ingredient. COPAXONE® contains the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate is 4,700-11,000 daltons. Chemically, glatiramer acetate is designated L-glutamic acid polymer with L-alanine, L-lysine and L-tyrosine, acetate (salt). Its structural formula is:

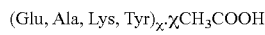

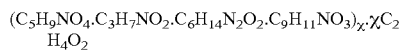

CAS-147245-92-9

("Copaxone", *Physician's Desk Reference*, (2000), Medical Economics Co., Inc., (Montvale, N.J.), 3115.)

Glatiramer acetate is approved for use in the reduction of the frequency of relapses in patients with relapsing-remitting multiple sclerosis. Multiple sclerosis has been classified as an autoimmune disease. Glatiramer acetate has also been disclosed for use in the treatment of other autoimmune diseases (Publication No. US 2002/0055466 A1 for R. Aharoni et al.), inflammatory non-autoimmune diseases (Publication No. US 2005/0014694 A1 for V. Wee Yong et al.; and U.S. Patent Application No. 2002/0077278 A1, published Jun. 20, 2002 (Young et al.)) and to promote nerve regeneration and/or to prevent or inhibit secondary degeneration which may follow primary nervous system injury (Publication No. US 2003/0004099 A1 for M. Eisenbach-Schwartz et al.; and U.S. Patent Application No. 2002/0037848 A1, published Mar. 28, 2002 (Eisenbach-Schwartz)). Furthermore, glatiramer acetate has been disclosed as a treatment for immune mediated diseases (e.g., U.S. Pat. No. 6,514,938 B1, issued Feb. 4, 2003 (Gad et al.); PCT International Publication No. WO 01/60392, published Aug. 23, 2001 (Gilbert et al.); and PCT International Publication No. WO 00/27417, published May 19, 2000 (Aharoni et al.) as well as diseases associated with demyelination (PCT International Publication No. WO 01/97846, published Dec. 27, 2001 (Moses et al.).

As a result of further study and improvement, a new mixture of such copolymers has been developed which has potential as a well-tolerated non-steroidal medication for the treatment of multiple sclerosis and other diseases as described more fully herein.

SUMMARY OF THE INVENTION

The invention provides a composition comprising a mixture of polypeptides, wherein each polypeptide (a) is a copolymer of the amino acids L-glutamic acid, L-alanine, L-tyrosine, and L-lysine, and (b) may be in the form of a pharmaceutically acceptable salt; and wherein in the mixture (i) the polypeptides have an average molecular weight in the range 13,500 to 18,500 daltons, (ii) 13% to 38% of the polypeptides have a diethylamide group instead of a carboxyl group present at one end thereof, and (iii) 68% of the polypeptides have a molecular weight between 7,000 and 41,000 daltons. In an embodiment, the average molecular weight is 16,000 daltons.

This invention also provides a process for making a composition comprising a mixture of polypeptides, comprising:

a) polymerizing N-carboxyanhydrides of L-tyrosine, L-alanine, γ-benzyl glutamate and trifluoroacetyl lysine with a predetermined amount of diethylamine to form a mixture of protected polypeptides;

b) removing the benzyl protecting group from the protected polypeptides by contacting the polypeptides with a hydrogen bromide and acetic acid solution at a temperature in the range of 17° C. to 23° C. for a period of 7 to 18 hours to produce a mixture of trifluoroacetyl protected polypeptides;

c) removing the trifluoroacetyl protecting group from the trifluoroacetyl protected polypeptides by contacting the protected polypeptides with an organic base solution to obtain deprotected polypeptide; and d) subjecting the deprotected polypeptides from step c) to ultrafiltration, thereby forming the composition.

The currently available data suggests that the development of the polypeptide mixture of the invention may address patient and physician needs by providing convenience (less frequent injections), increased and sustained efficacy, and improved neuroprotective potential.

DETAILED DESCRIPTION OF THE INVENTION

1. Embodiments of the Invention

Figure 1:
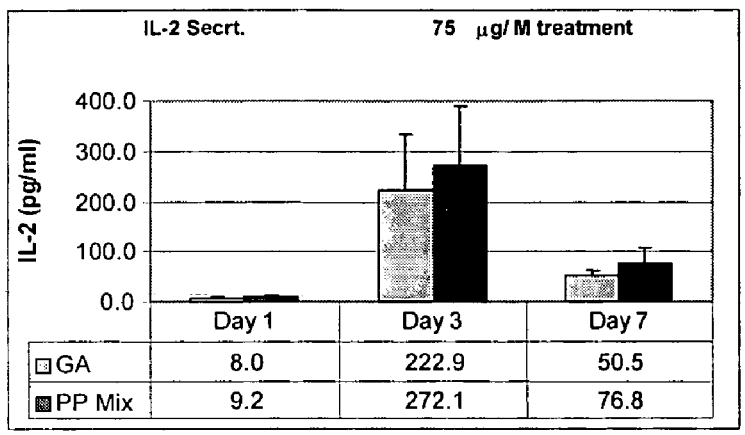
FIG. 1 Cytokine secretion (IL-2, IFN-γ, IL-10) from mouse splenocytes following a single injection of the mixture of polypeptides of the invention or GA. [The bars represent the mean±STD of values obtained in 2-3 experiments. M=mouse.]
Figure 1:
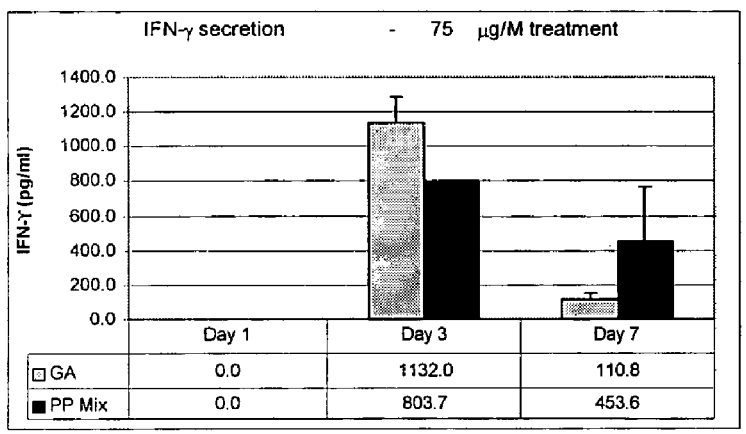
Figure 1:
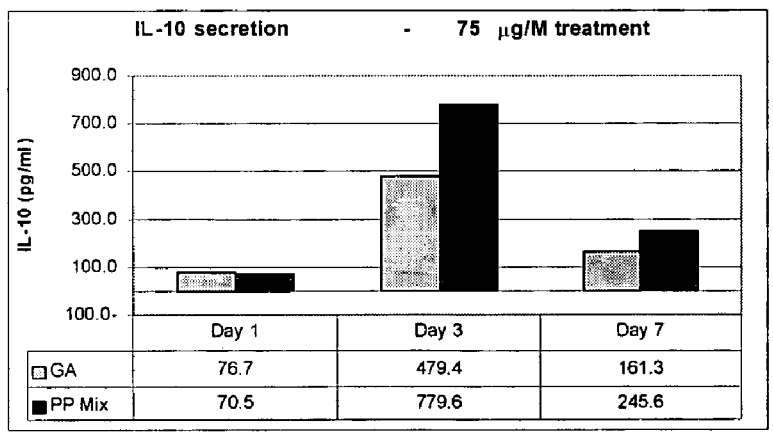

The invention provides a composition comprising a mixture of polypeptides, wherein each polypeptide (a) is a copolymer of the amino acids L-glutamic acid, L-alanine, L-tyrosine, and L-lysine, and (b) may be in the form of a pharmaceutically acceptable salt; and wherein in the mixture (i) the polypeptides have an average molecular weight in the range 13,500 to 18,500 daltons, (ii) 13% to 38% of the polypeptides have a diethylamide group instead of a carboxyl group present at one end thereof, and (iii) 68% of the polypeptides have a molecular weight between 7,000 and 41,000 daltons. In an embodiment, the average molecular weight is 16,000 daltons.

In any of the disclosed embodiments, the amino acids are present in the mixture in an amount such that the average molar fraction of the amino acids is: L-glutamic acid 0.129-0.153; L-alanine 0.392-0.462; L-tyrosine 0.086-0.100; and L-lysine 0.300-0.374. In an embodiment, the amino acids are present in the mixture in an amount such that the average molar fraction of the amino acids is: L-glutamic acid 0.141; L-alanine 0.427; L-tyrosine 0.095; and L-lysine 0.338.

In any of the disclosed embodiments, 19% to 28% of the polypeptides in the mixture can have diethylamide at one end thereof; the remainder of polypeptides in the mixture may have a carboxyl group at the C-terminus.

In another embodiment, 35-45% of the polypeptides in the mixture have a L-alanine at the N-terminus, preferably 37-41%, or 38-39%, or 39%.

In yet another embodiment, less than 5%, preferably less than 3%, of the polypeptides in the mixture have a molecular weight below 4,700 daltons.

In an embodiment, polypeptides in the mixture do not all have the same amino acid sequence.

In any of the disclosed embodiments, the mixture of polypeptides may have a circular dichroism value of 0.91.

In any of the disclosed embodiments, the polypeptides are in the form of a pharmaceutically acceptable salt, which may be an organic salt, an acid addition salt. In a further embodiment, the salt is an acetate salt or chloride salt.

In any of the disclosed embodiments, the composition disclosed may be further characterized by having at least 90% suppressive activity in an EAE blocking test when administered at a dose of 100 μg/mouse of the polypeptide mixture.

In any of the disclosed embodiments, the composition may be lyophilized.

The invention also provides a pharmaceutical composition comprising a therapeutically effective amount of the composition of any of the disclosed embodiments and a pharmaceutically acceptable carrier. In an embodiment, the pharmaceutically acceptable carrier comprises mannitol.

The pharmaceutical composition may further be a liposome, comprises an adjuvant. In a still further embodiment, the adjuvant such as alum, a phospholipid, a DNA adjuvant, complete Feund's adjuvant, or incomplete Freund's adjuvant.

In any of the disclosed embodiments, the polypeptide mixture may be in or attached to a nanoparticle, for example, electrostatically.

In any of the disclosed embodiments, the effective amount may be 0.1 mg to 70 mg. In an embodiment the effective amount may be 0.5 mg to 60 mg; 1 mg to 50 mg; 5 mg to 35 mg; 10 mg to 30 mg; 45 mg to 70 mg; 50 mg to 70 mg; 15 mg to 25 mg; 18 mg to 22 mg; 0.1 mg to 2 mg; 0.5 mg to 1.5 mg; 2 mg to 7 mg; 4 mg to 6 mg; 12 mg to 18 mg; 14 mg to 16 mg; 17 mg to 23 mg; 19 mg to 21 mg; 27 mg to 33 mg; 29 mg to 31 mg; 47 mg to 53 mg; or 49 mg to 51 mg. In another embodiment, the effective amount may be 1 mg; 5 mg; 15 mg; 20 mg; 30 mg; or 50 mg.

In any of the disclosed embodiments, the composition may have a pH between 5.5 and 9.0; between 5.5 and 8.5; between 5.5 and 7.5; between 5.5 and 7.0; between 5.5 and 6; may be 5.7; or may be 5.5.

The invention also provides a pharmaceutical composition of any of any of the disclosed embodiments, further comprising at least one of riluzole, glatiramer acetate, baclofen, phenytoin, quinine, amitriptyline, phenothiazine, chlorpromazine, butyrophenone neuroleptics, geldanamycin, RNA interference, trehalose, cystamine, rapamycin, glucocorticoid, nonsteroidal anti-inflammatory drug, minocycline, folic acid, creatine, dichloroacetate, nicotinamide, riboflavin, carnitine, tauroursodeoxycholic acid, ginko biloba, coenzyme Q10, vitamin A, vitamin C, vitamin E, selenium, lipoic acid, arginine, mithramycin, remacemide, filuzole, lamotrigine, memantine, gabamentin, HDAC inhibitors, retinoic acid, reserpine, anticholinergics, diphenoxylate, loperamide, deodorized opium tincture, codeine, metronidazole, sulfasalazine, corticosteroid, azathioprine, 6-mercaptopurine, cyclosporine, T lymphocyte aphaeresis, 4-amino quinolines, methotrexate), loperamide, 5-aminosalicylic acid (5-ASA), balsalazide, olsalazine, ACTH 75, ACTH 120, antibiotic, pilocarpine, isoptocarpine timolol hemihydrate, timolol maleate, betaxolol, levobunolol, carteolol, metipranolol, epinephrine, dipivefrin, carbachol, apraclonidine, brimonidine, dorzolamide, latanoprost, travaprost, brimatoprost, brinzolamide, cholinesterase inhibitor, demecarium, isoblurophate, carbonic anhydrase inhibitor, mannitol, oral glycerin, and mydriatics, memantine, atropine, meclizine, dienhydrinate, prochlorperazine, scopolamine, diphenhydramine, clonazepam, gabapentin, primidone, botulinum toxin, actazolamide, and cabidopa-levodopa, isoniazid, diazepam, clonazepam, dantrolene sodium, tizanidine, clonidine, sildenafil, alprostadil, papaverine, bisacodyl, magnesium hydroxide, glycerin, psyllium hydrophilic mucilloid, sodium phosphate, anti-tumor necrosis factor (TNF), docusate, oxybutynin, desmopressin, vasopressin, tolterodine, carbamazepine, imipramine, bethane, phenoxybenzamine, terazosin, propantheline, oxybutonin, hyoscyamine, methenamine, nitrofurantoin, phenazopyridine, ciprofloxacin, amantadine, pemoline, vitamin D derivative, modafinil, fluoxetine, sertraline, venlafaxine, citalopram, parocetine, trazodone, nortriptyline, imipramine, dothiepin, lofepramine, doxepin, protriptyline, tranylcypromine, moclobemide, bupropion, nefazodone, mirtazapine, zolpidem, alprazolam, temazepam, buspirone, gabatentin, topiramate, zonisamide, desipramine, imipramine, doxepin, protriptyline, pentozifylline, hydroxyzine, natalizumab, steroids, muscle relaxants, prednisolone, dexamethasone, corticotrophin, immunosuppressants, acyclovir, azathioprine, cyclophosphamide, mitoxantrone, cyclosporine, methotrexate, cladribine, interferons, laquinimod, alemtuzumab, 4-aminopyridine, 3,4-diaminopyridine, eliprodil, IV immunoglobin, pregabalin, or ziconotide.

In any of the disclosed embodiments, the compostion may be lyophilized.

This invention also provides a process for making a composition comprising a mixture of polypeptides, comprising:

e) polymerizing N-carboxyanhydrides of L-tyrosine, L-alanine, γ-benzyl glutamate and trifluoroacetyl lysine with a predetermined amount of diethylamine to form a mixture of protected polypeptides;

f) removing the benzyl protecting group from the protected polypeptides by contacting the polypeptides with a hydrogen bromide and acetic acid solution at a temperature in the range of 17° C. to 23° C. for a period of 7 to 18 hours to produce a mixture of trifluoroacetyl protected polypeptides;

g) removing the trifluoroacetyl protecting group from the trifluoroacetyl protected polypeptides by contacting the protected polypeptides with an organic base solution to obtain deprotected polypeptide; and h) subjecting the deprotected polypeptides from step c) to ultrafiltration, thereby forming the composition.

In an embodiment, the removal of the benzyl protecting group in step b) may be performed at a temperature in the range of 17-21° C. In a further embodiment the removal of the benzyl protecting group in step b) may be conducted at a temperature in the range of 19-20° C.

In any embodiment of the process, the removal of the benzyl protecting group in step b) may be conducted over a period of 7 to 15 hours, for example approximately 15 hours.

In any embodiment of the process, the organic base in step c) may be a primary amine, a secondary amine, a tertiary amine, methanolic ammonia, piperidine.

In any embodiment of the process, the hydrogen bromide and acetic acid solution is from 10% to 36% hydrobromic acid in acetic acid. In another embodiment, the hydrobromic acid in acetic acid is from 16% to 33% hydrobromic acid in acetic acid; 18% to 33% hydrobromic acid in acetic acid; 20% to 37% hydrobromic acid in acetic acid; 20% to 33% hydrobromic acid in acetic acid; 22% to 33% hydrobromic acid in acetic acid; 24% to 33% hydrobromic acid in acetic acid; 25% to 35% hydrobromic acid in acetic acid; 26% to 33% hydrobromic acid in acetic acid; 28% to 33% hydrobromic acid in acetic acid; 30% to 34% hydrobromic acid is acetic acid; 30% to 33% hydrobromic acid in acetic acid; or 32% to 33% hydrobromic acid in acetic acid. In a further embodiment, the solution is 33% hydrobromic acid in acetic acid. In another embodiment, the solution is 16% hydrobromic acid in acetic acid.

The hydrogen bromide and acetic acid solution may be pretreated with a bromine scavenger, such as phenol, in order to remove free bromine.

In an embodiment, the process of any of disclosed embodiments may further comprise a step of lyophilizing the composition.

This invention also provides a process for preparing a pharmaceutical composition comprising combining a therapeutically effective amount of the composition of any of the disclosed embodiments with a pharmaceutically acceptable carrier disclosed herein.

This inevention further provides a method of treating a human subject afflicted with an autoimmune disease comprising administering to the subject a therapeutically effective amount of any of the disclosed compositions, so as to treat the human subject.

The invention also provides a method of treating a human subject afflicted with an inflammatory non-autoimmune disease, an immune mediated disease, or a disease associated with demyelination comprising administering to the subject a therapeutically effective amount of any of the disclosed compositions, so as to treat the human subject.

The invention further provides a method of alleviating a symptom of an autoimmune disease in a subject afflicted with such a disease, comprising administering to the human subject a therapeutically effective amount of any of the disclosed compositions in an amount effective to alleviate the symptom.

The invention also provides a method of alleviating a symptom of an inflammatory non-autoimmune disease, an immune mediated disease, or a disease associated with demyelination in a subject afflicted with such a disease, comprising administering to the human subject a therapeutically effective amount of any of the disclosed compositions in an amount effective to alleviate the symptoms.

The invention also provides a method of promoting nerve regeneration or preventing or inhibiting secondary degeneration which may otherwise follow primary nervous system injury in a human subject comprising administering to the human subject a therapeutically effective amount of any of the disclosed compositions.

The invention also provides a method of treating a human subject afflicted with a neurodegenerative disease comprising administering to the human subject a therapeutically effective amount of any of the disclosed compositions so as to thereby treat the human subject.

The invention further provides a method of alleviating a symptom of a deurodegenerative disease comprising administering to the human subject the composition of any of the embodiments or of the pharmaceutical compostion of any of any of the embodiments in an amount effective to alleviate the symptom.

The neurodegenerative disease may be Huntington's disease, in which case, the method may further comprise administering to the subject phenothiazine, butyrophenone neuroleptics, haloperidol, reserpine, or a combination thereof.

The neurodegenerative disease may be glaucoma, in which case, the method preserves the structural integrity of the optic nerve of the human subject afflicted with glaucoma, preserves the retinal cells in the human subject afflicted with glaucoma and/or reduces the rate of visual field loss in the human subject afflicted with glaucoma.

When the neurodegenerative disease is glaucoma, the method can further comprise administering to the subject a second agent, wherein the second agent is glatiramer acetate, pilocarpine, timolol maleate, betaxolol, levobunolol, metipranolol, epinephrine, dipivefrin, carbachol, potent cholinesterase inhibitors, carbonic anhydrase inhibitors, atropine, mydriatics, or a combination thereof. Preferably, the amount of the composition and the dose of the second agent, taken together, are effective to treat the subject; each of the amount of the composition taken alone, and the dose of the second agent taken alone is effective to treat the subject, or either the amount of the composition taken alone or the dose of the second agent taken alone is not effective to treat the human subject.

In an embodiment, the human subject never previously received the second agent for therapy.

In an embodiment, the human subject may have received both the polypeptide mixture of the invention and the second agent, but subsequently the second agent is discontinued.

When the neurodegenerative disease is glaucoma, the treatment may further comprise laser trabeculoplasty, filtering surgery, peripheral iridectomy, or laser iridectomy.

When the neurodegenerative disease is glaucoma, the composition may be administered once every 1 to 12 weeks; once every 3 to 12 weeks; once every 3 to 8 weeks; once every 2 to 6 weeks; once every 1 to 2 weeks; once every 3 to 5 weeks; once every 4 to 10 weeks; once every 4 weeks; once every 2 months.

When the neurodegenerative disease is glaucoma, the amount of the composition may be 0.1 mg to 70 mg of the composition; 0.5 mg to 60 mg of the composition; 1 mg to 50 mg of the composition; 5 mg to 35 mg of the composition; 10 mg to 30 mg of the composition; 45 mg to 70 mg of the composition; 50 mg to 70 mg of the composition; 15 mg to 25 mg of the composition; 18 mg to 22 mg of the composition; 0.1 mg to 2 mg of the composition; 0.5 mg to 1.5 mg of the composition; 2 mg to 7 mg of the composition; 4 mg to 6 mg of the composition; 12 mg to 18 mg of the composition; 14 mg to 16 mg of the composition; 17 mg to 23 mg of the composition; 19 mg to 21 mg of the composition; 27 mg to 33 mg of the composition; 29 mg to 31 mg of the composition; 47 mg to 53 mg of the composition; 49 mg to 51 mg of the composition; 5 mg of the composition; 15 mg of the composition; 30 mg of the composition; and 50 mg of the composition.

When the neurodegenerative disease is glaucoma, the administration may be through an intravenous, intraperitoneal, intramuscular, subcutaneous, oral, intranasal, buccal, vaginal, rectal, intraocular, intrathecal, topical or intradermal route. In an embodiment, the composition may be administered intranasally and the dose may be less than 1 mg or the composition may be administered orally and the dose may be 70 mg. Preferably, the composition is administered by injection.

The invention also provides a method of treating a human subject afflicted with an inflammatory bowel disease comprising administering to the human subject a therapeutically effective amount of any disclosed composition so as to treat the inflammatory bowel disease.

The subject invention further provides a method of alleviating a symptom of an inflammatory bowel disease comprising administering to the human subject any disclosed composition in an amount effective to alleviate the symptom.

When the disease is inflammatory bowel disease, the method may further comprise administering to the subject a second agent, wherein the second agent is an anticholinergic, diphenoxylate, loperamide, deodorized opium tincture, codeine, antibiotics, metronidazole, sulfasalazine, corticosteroids, prednisone, hydrocortisone, antimetabolites, azathioprine, 6-mercaptopurine, cyclosporine, methotrexate, 4-amino quinolines, loperamide, 5-aminosalicylic acid (5-ASA), sulfasalazine, olsalazine, prednisone, ACTH 75, ACTH 120, antibiotics, or a combination thereof. In an embodiment, the effective amount of the composition and the dose of the second agent, taken together, may be effective to treat the patient afflicted with inflammatory bowel disease; each of the effective amount of the composition, taken alone, and the dose of the second agent, taken alone may be effective to treat the patient afflicted with inflammatory bowel disease;

or either the effective amount of the composition taken alone, or the dose of the second agent taken alone may be not effective to treat the patient afflicted with inflammatory bowel disease.

In an embodiment, the human subject never previously received the second agent as a treatment for inflammatory bowel disease.

In another embodiment, the human subject received both the polypeptide mixture of the invention and the second agent, but subsequently the second agent is discontinued.

In a further embodiment, the method may further comprise ingestion of an elemental diet, hyperalimentation, surgery, proctoclectomy with abdominoperineal resection, emergency colectomy, subtotal colectomy with ileostomy or rectosigmoid mucous fistula.

The inflammatory bowel disease may be Crohn's Disease or ulcerative colitis.

In an embodiment of the method, the amount of the composition may be from 0.1 mg to 70 mg of the composition; 0.5 mg to 60 mg mg of the composition; 1 mg to 50 mg of the composition; 5 mg to 35 mg of the composition; 10 mg to 30 mg of the composition; 45 mg to 70 mg of the composition; 50 mg to 70 mg of the composition; 15 mg to 25 mg of the composition; 18 mg to 22 mg of the composition; 0.1 mg to 2 mg of the composition; 0.5 mg to 1.5 mg of the composition; 2 mg to 7 mg of the composition; 4 mg to 6 mg of the composition; 12 mg to 18 mg of the composition; 14 mg to 16 mg of the composition; 17 mg to 23 mg of the composition; 19 mg to 21 mg of the composition; 27 mg to 33 mg of the composition; 29 mg to 31 mg of the composition; 47 mg to 53 mg of the composition; 49 mg to 51 mg of the composition; 5 mg of the composition; 15 mg of the composition; 30 mg of the composition; and 50 mg of the composition.

In an embodiment of the method, the composition may be administered every 1 to 60 days; every 1 to 30 days; every 5 to 60 days; every 7 to 60 days; every 5 to 30 days; every 20 to 40 days; every 50 to 60 days; every 5 to 9 days; every 6 to 8 days; every 7 days; every 14 days; 30 days; 60 days; or every 2 months.

In the method, the administration of the composition may be through an intravenous, intraperitoneal, intramuscular, subcutaneous, oral, intranasal, buccal, vaginal, rectal, intraocular, intrathecal, topical or intradermal route.

Preferably, the composition is administered by injection. More preferably, the composition is administered orally.

The invention also provides a method of treating a human subject afflicted with multiple sclerosis comprising administering to the human subject a therapeutically effective amount of any disclosed composition so as to thereby treat the human subject afflicted with multiple sclerosis.

The invention further provides a method of alleviating a symptom of multiple sclerosis in a human subject afflicted with multiple sclerosis comprising administering to the human subject an amount of any disclosed composition in an amount effective to alleviate the symptom of multiple sclerosis.

The invention still further provides a method of reducing the frequency of relapses in a human subject afflicted with relapse remitting multiple sclerosis comprising administering to the human subject a therapeutically effective amount of any disclosed composition so as to thereby reduce the frequency of relapses in the human subject.

The invention also provides a method of reducing the disability based on the EDSS scale of a human subject afflicted with multiple sclerosis comprising administering to the human subject a therapeutically effective amount of any disclosed composition so as to thereby reduce the disability based on EDSS scale in the human subject.

The invention further provides a method of reducing lesions detected by magnetic resonance imagining (MRI) in a human subject afflicted with multiple sclerosis comprising administering to the human subject a therapeutically effective amount of any disclosed composition so as to thereby reduce the lesions detected by MRI in the human afflicted with multiple sclerosis.

When the disease is multiple sclerosis, the method may further comprise administration of a second agent, wherein the second agent is glatiramer acetate, a pain reliever, a steroid, a muscle relaxant, prednisone, dexamethasone, an immunosuppressant, azathioprine, cyclophosphamide, an interferon, natalizumab, riluzole, alphacalcidol, calcitriol, rasagiline, minocycline, mitoxantrone, simvastatin, or a combination thereof. Preferably, the second agent is glatiramer acetate. In an embodiment, the amount of the composition and the dose of the second agent taken together are effective to treat the subject; each of the amount of the composition taken alone, and the dose of the second agent taken alone is effective to treat the subject; or either the effective amount of the composition taken alone, the dose of the second agent taken alone is not effective to treat the subject. In a further embodiment, the subject never previously received the second agent for therapy. In another embodiment, the subject has received the second agent for therapy, but is no longer receiving the second agent for therapy.

In any embodiment of the method, it may further comprise plasmaphoresis, or total lymphoid radiation.

In any embodiment of the method, the composition may be administered every 1 to 60 days; 1 to 30 days; every 5 to 60 days; every 7 to 60 days; every 5 to 30 days; every 20 to 40 days; every 50 to 60 days; every 5 to 9 days; every 6 to 8 days; every 7 days; every 14 days; 30 days; 60 days; or every 2 months.

In the method, the amount of the composition may be 0.1 mg to 100 mg of the composition; 1 mg to 80 mg of the composition; 1 mg to 50 mg of the composition; 5 mg to 25 mg of the composition; 25 mg to 75 mg of the composition; 2 mg to 8 mg of the composition; 4 mg to 6 mg of the composition; 12 mg to 18 mg of the composition; 14 mg to 16 mg of the composition; 27 mg to 33 mg of the composition; 29 mg to 31 mg of the composition; 47 mg to 53 mg of the composition; 49 mg to 51 mg of the composition; 5 mg of the composition; 15 mg of the composition; 30 mg of the composition; or 50 mg of the composition.

In any embodiment of the method the administration may be through an intravenous, intraperitoneal, intramuscular, subcutaneous, oral, intranasal, buccal, vaginal, rectal, intraocular, intrathecal, topical or intradermal route. Preferably, the administering of the composition is by injection or orally.

The invention also provides any of the disclosed compositions for use as a medicament.

The invention further provides a product containing the composition of any of the disclosed compositions and a second pharmaceutical agent, as a combined preparation for simultaneous, separate or sequential use as a medicament.

The invention still further provides a use of any disclosed composition for the manufacture of a medicament for the treatment of a disease in a human subject.

The invention also provides a use of any disclosed composition and of a second agent for the manufacture of a medicament for the treatment of a disease in a human subject.

The invention also provides a process for preparing a composition comprising:

preparing a mixture of polypeptides, wherein each polypeptide in the mixture (a) is a copolymer of the amino acids L-alanine, L-glutamic acid, L-tyrosine and L-lysine, and (b) may be present in the form of a pharmaceutically acceptable salt; and wherein in the mixture 13% to 38% of the polypeptides have a diethylamide group instead of a carboxyl group present at one end thereof;

determining the average molecular weight of the polypeptides in the mixture by size exclusion chromatography on a gel permeation chromatography column calibrated using a plurality of copolymers of defined sequence and molecular weight; and including in the composition only those polypeptide mixtures determined to have an average molecular weight between 13,500 and 18,500 Daltons, wherein each of the copolymers is a polypeptide consisting of L-alanine, L-glutamic acid, L-tyrosine and L-lysine with a defined molecular weight between 12,000 and 30,000 Daltons.

The invention further provides a process for determining whether polypeptides in a mixture have an average molecular weight between 13,500 daltons and 18,500 daltons, each of which polypeptides (a) is a copolymer of the amino acids L-alanine, L-glutamic acid, L-tyrosine and L-lysine, and (b) may be present in the form of a pharmaceutically acceptable salt, and wherein 13% to 38% of the polypeptides in the mixture have a diethylamide group instead of a carboxyl group present at one end thereof, comprising subjecting the polypeptide mixture to gel permeation chromatography to determine whether the polypeptides in the mixture have the average molecular weight, wherein the gel permeation chromatography is carried out on a column calibrated by subjecting a plurality of molecular weight markers to chromatography on the column to establish a relationship between retention time on the column and molecular weight, each such marker being a copolymer of L-alanine, L-glutamic acid, L-tyrosine, L-lysine, having a defined sequence, and having a defined molecular weight between 12,000 and 30,000 Daltons.

The invention still further provides a process for determining the average molecular weight of a mixture of polypeptides, each of which polypeptides (a) is a copolymer of the amino acids L-alanine, L-glutamic acid, L-tyrosine and L-lysine, and (b) may be present in the form of a pharmaceutically acceptable salt, and wherein in the mixture 13% to 38% of the polypeptides have a diethylamide group instead of a carboxyl group present at one end thereof, which process comprises subjecting the polypeptide mixture to gel permeation chromatography so as to determine the average molecular weight of the polypeptides in the mixture, wherein the gel permeation chromatography is carried out on a column calibrated by subjecting a plurality of molecular weight markers to chromatography on the column to establish a relationship between retention time on the column and molecular weight, each such marker being a copolymer of L-alanine, L-glutamic acid, L-tyrosine and L-lysine, having a defined sequence, and having a defined molecular weight of 12,000 to 30,000 daltons.

In an embodiment of the disclosed process, the average molecular weight of the polypeptides in the mixture may be 16,000 daltons.

In another embodiment, the gel permeation chromatography column may comprise a cross-linked agarose, for example, a cross-linked agarose with an exclusion limit of $2 \times 10^6$ Daltons, an optimal separation range of 1000 to $3 \times 10^5$ Daltons, and a bead diameter of 20-40 μm.

In a further embodiment, each of the plurality of molecular weight markers may have a molecular weight between 16,000 and 27,000 daltons.

In any of the disclosed embodiments of the process, in each marker the amino acids may be present in an amount such that the molar fraction of L-glutamic acid is 0.129-0.153, of L-alanine is 0.392-0.462, of L-tyrosine is 0.086-0.100, and of L-lysine is 0.300-0.374.

In any of the disclosed embodiments of the process, the plurality of molecular weight markers may comprise five polypeptides having the following sequences:

(SEQ ID NO: 1)
AEKYKAKKAKEKAYKKKAKEAKKAKYKAKEAKAYKAEKKAKYAKAKEKAY

AKAKEAKAYAKAKAKAEKAKAKAKYAEKAKAAKYAEKAAKYAEAKAKAAE

AKYAAEAKEAAKAAEAKYAAKAEAAKYAAEKAAEKYAKAEAAAEAKEAA;

(SEQ ID NO: 2)
AKKKYKAKEKKAKKKAKEKKYKAKKAKYKEKAAKYKAKKAKAKYKAKAEK

AKAKAEKAKAYAEKAKAKYAKEAKKYAEKAKKAEYKAKEAAEKAKAYAKE

AAKAEKAAKAAEKAAKAYAKAEAAAKEAAYAAKAEAKAAYAAEAAKAEYA

AEAAKEAAYAAAEYAAEAA;

(SEQ ID NO: 3)
AKKKYKAKEKKAKKKAKEKKKYKAKEKKAKKYKEKAAKYKAKKAKKEAAK

YKKAKAEKAKYAKEKAEKAKAYAEKAKAKYAKEAKKYAEKAKKAEYKAKE

AAEKAKAYAKEAAKAEAKAAKYAAEKAAEAAKAAYAKAEAAKAAKEAAYA

AKAEAAKAAYAAEAAKAEYAAEAAKEAAYAAAEYAAAEAA;

(SEQ ID NO: 4)
AKKKYKAKEKKAKAKKKAKEKKKYKAKKEKKAKKYKEKAAKYKAKKEKAK

KEAAKYKKAKKYKAEKAKYAKEKAKEKAKAYAEKAEKAAKYAAKEAKKYA

EKAAEKKAEYKAKEAAEKYAAKAYAAKEAAKAYKEAKAAKYAKAAEKAAA

KEAAKAAYAAKAEAAKEAAKEAAYAAAKAEAAAAKAAAYAAEAAAKAEYA

AEAAAKEAAYAAAEYAAAEAA;

or (SEQ ID NO: 5)
AKKKYKAKEKKAKYKAKKEKKAKEKKAKKKYKAKKKAAEKKYAKEKKAKE

KAAKKYKAKKEKAKKEAAKYKKAKKYKAEKKAKYAAKEKAKEKAKAYAEK

KAEKAAKYAAKEAKKYAEKAAEKKAEYKAKEAAEKYAAKKAEYAAEKEAA

KAYKEAKAAKYAKAAEKAKAAKEAAKAAYAAKAEAAKEAAKEAAYAAAKA

EAAAYAAAKAAAAYAAEAAAKAEYAAAEAAAKEAAYAAAEYAAAAEAAA, wherein A represents L-alanine, K represents L-lysine, Y represents L-tyrosine, and E represents L-glutamic acid.

Any disclosed embodiment of the process, may further comprise combining the composition with a pharmaceutically acceptable carrier, for example, mannitol.

Any disclosed embodiment of the process, may further comprise sterilizing the composition.

Any disclosed embodiment of the process, may further comprise lyophilizing the composition.

The invention also provides a polypeptide consisting of consecutive amino acids having a sequence selected from the following:

(SEQ ID NO: 1)
AEKYKAKKAKEKAYKKKAKEAKKAKYKAKEAKAYKAEKKAKYAKAKEKAY

AKAKEAKAYAKAKAKAEKAKAKAKYAEKAKAAKYAEKAAKYAEAKAKAAE

AKYAAEAKEAAKAAEAKYAAKAEAAKYAAEKAAEKYAKAEAAAEAKEAA;

(SEQ ID NO: 2)
AKKKYKAKEKKAKKKAKEKKYKAKKAKYKEKAAKYKAKKAKAKYKAKAEK

AKAKAEKAKAYAEKAKAKYAKEAKKYAEKAKKAEYKAKEAAEKAKAYAKE

AAKAEKAAKAAEKAAKAYAKAEAAAKEAAYAAKAEAKAAYAAEAAKAEYA

AEAAKEAAYAAAEYAAEAA;

(SEQ ID NO: 3)
AKKKYKAKEKKAKKKAKEKKKYKAKEKKAKKYKEKAAKYKAKKAKKEAAK

YKKAKAEKAKYAKEKAEKAKAYAEKAKAKYAKEAKKYAEKAKKAEYKAKE

AAEKAKAYAKEAAKAEAKAAKYAAEKAAEAAKAAYAKAEAAKAAKEAAYA

AKAEAAKAAYAAEAAKAEYAAEAAKEAAYAAAEYAAAEAA;

(SEQ ID NO: 4)
AKKKYKAKEKKAKAKKKAKEKKKYKAKKEKKAKKYKEKAAKYKAKKEKAK

KEAAKYKKAKKYKAEKAKYAKEKAKEKAKAYAEKAEKAAKYAAKEAKKYA

EKAAEKKAEYKAKEAAEKYAAKAYAAKEAAKAYKEAKAAKYAKAAEKAAA

KEAAKAAYAAKAEAAKEAAKEAAYAAAKAEAAAAKAAAYAAEAAAKAEYA

AEAAAKEAAYAAAEYAAAEAA;
or (SEQ ID NO: 5)
AKKKYKAKEKKAKYKAKKEKKAKEKKAKKKYKAKKKAAEKKYAKEKKAKE

KAAKKYKAKKEKAKKEAAKYKKAKKYKAEKKAKYAAKEKAKEKAKAYAEK

KAEKAAKYAAKEAKKYAEKAAEKKAEYKAKEAAEKYAAKKAEYAAEKEAA

KAYKEAKAAKYAKAAEKAKAAKEAAKAAYAAKAEAAKEAAKEAAYAAAKA

EAAAYAAAKAAAAYAAEAAAKAEYAAAEAAAKEAAYAAAEYAAAAEAAA, wherein A represents L-alanine, K represents L-lysine, Y represents L-tyrosine, and E represents L-glutamic acid.

The invention also provides a disclosed polypeptide of having the sequence:

(SEQ ID NO: 1)
AEKYKAKKAKEKAYKKKAKEAKKAKYKAKEAKAYKAEKKAKYAKAKEKAY

AKAKEAKAYAKAKAKAEKAKAKAKYAEKAKAAKYAEKAAKYAEAKAKAAE

AKYAAEAKEAAKAAEAKYAAKAEAAKYAAEKAAEKYAKAEAAAEAKEAA.

The invention also provides a disclosed polypeptide of having the sequence:

(SEQ ID NO: 2)
AKKKYKAKEKKAKKKAKEKKYKAKKAKYKEKAAKYKAKKAKAKYKAKAEK

AKAKAEKAKAYAEKAKAKYAKEAKKYAEKAKKAEYKAKEAAEKAKAYAKE

AAKAEKAAKAAEKAAKAYAKAEAAAKEAAYAAKAEAKAAYAAEAAKAEYA

AEAAKEAAYAAAEYAAEAA.

The invention also provides a disclosed polypeptide of having the sequence:

(SEQ ID NO: 3)
AKKKYKAKEKKAKKKAKEKKKYKAKEKKAKKYKEKAAKYKAKKAKKEAAK

YKKAKAEKAKYAKEKAEKAKAYAEKAKAKYAKEAKKYAEKAKKAEYKAKE

AAEKAKAYAKEAAKAEAKAAKYAAEKAAEAAKAAYAKAEAAKAAKEAAYA

AKAEAAKAAYAAEAAKAEYAAEAAKEAAYAAAEYAAAEAA.

The invention also provides a disclosed polypeptide of having the sequence:

(SEQ ID NO: 4)
AKKKYKAKEKKAKAKKKAKEKKKYKAKKEKKAKKYKEKAAKYKAKKEKAK

KEAAKYKKAKKYKAEKAKYAKEKAKEKAKAYAEKAEKAAKYAAKEAKKYA

EKAAEKKAEYKAKEAAEKYAAKAYAAKEAAKAYKEAKAAKYAKAAEKAAA

KEAAKAAYAAKAEAAKEAAKEAAYAAAKAEAAAAKAAAYAAEAAAKAEYA

AEAAAKEAAYAAAEYAAAEAA.

The invention also provides a disclosed polypeptide of having the sequence:

(SEQ ID NO: 5)
AKKKYKAKEKKAKYKAKKEKKAKEKKAKKKYKAKKKAAEKKYAKEKKAKE

KAAKKYKAKKEKAKKEAAKYKKAKKYKAEKKAKYAAKEKAKEKAKAYAEK

KAEKAAKYAAKEAKKYAEKAAEKKAEYKAKEAAEKYAAKKAEYAAEKEAA

KAYKEAKAAKYAKAAEKAKAAKEAAKAAYAAKAEAAKEAAKEAAYAAAKA

EAAAYAAAKAAAAYAAEAAAKAEYAAAEAAAKEAAYAAAEYAAAAEAAA.

The invention further provides DNA encoding any of the disclosed polypeptide sequences.

The invention also provides DNA of the disclosed polypeptide of having the sequence:

(SEQ ID NO: 6)
ATGGCCGAGAAATACAAGGCTAAGAAAGCGAAGGAAAAAGCATACAAGAA

AAAGGCCAAAGAAGCAAAAAAGGCAAAATATAAGGCTAAAGAAGCGAAAG

CGTATAAAGCAGAAAAAAAGGCGAAATATGCAAAAGCAAAAGAAAAGGCT

TATGCTAAAGCCAAGGAGGCAAAAGCATACGCGAAAGCCAAAGCAAAAGC

CGAAAAGGCTAAAGCTAAAGCGAAATATGCTGAGAAAGCTAAAGCCGCGA

AGTATGCCGAAAAAGCGGCCAAATATGCGGAAGCCAAAGCAAAGGCCGCT

GAGGCAAAATATGCCGCAGAAGCTAAAGAAGCTGCGAAAGCCGCGGAAGC

AAAATACGCGGCAAAGGCAGAAGCGGCCAAATATGCCGCGGAGAAGGCCG

CGGAAAAGTATGCGAAAGCTGAAGCCGCGGCCGAGGCGAAAGAGGCGGCG

TAA.

The invention also provides DNA of the disclosed polypeptide of having the sequence:

(SEQ ID NO: 7)
ATGGCAAAGAAGAAATATAAGGCGAAAGAAAAGAAGGCTAAGAAGAAAGC

AAAAGAGAAGAAGTACAAAGCCAAGAAGGCGAAATACAAAGAAAAGGCGG

CAAAGTATAAGGCTAAAAAGGCGAAAGCTAAATACAAAGCCAAAGCCGAG

-continued

```
AAAGCGAAAGCTAAAGCAGAAAAAGCGAAAGCTTATGCGGAAAAAGCGAA

AGCAAAATATGCGAAAGAAGCCAAAAAGTATGCGGAGAAAGCAAAAAAG

CTGAGTATAAAGCTAAAGAAGCCGCAGAAAAAGCTAAAGCTTATGCCAAA

GAGGCTGCAAAAGCAGAAAAAGCTGCGAAAGCAGCGGAAAAAGCCGCTAA

GGCTTATGCGAAAGCGGAAGCCGCAGCCAAAGAAGCTGCCTACGCCGCGA

AAGCAGAAGCTAAAGCGGCCTATGCCGCAGAGGCAGCCAAAGCGGAATAC

GCGGCTGAAGCGGCAAAAGAGGCGGCTTACGCAGCCGCGGAATACGCGGC

CGAGGCGGCCTAA.
```

The invention also provides DNA of the disclosed polypeptide of having the sequence:

```
                                          (SEQ ID NO: 8)
ATGGCAAAGAAGAAATATAAGGCGAAAGAAAAGAAGGCTAAGAAGAAAGC

AAAAGAGAAGAAGAAATACAAAGCCAAGGAAAAGAAAGCCAAAAAGTACA

AAGAAAAGGCGGCAAAGTATAAGGCTAAAAAGGCGAAAAAGGAAGCGGCT

AAATACAAAAAGGCCAAAGCCGAGAAAGCGAAATATGCGAAGGAAAAAGC

AGAAAAAGCGAAAGCTTATGCGGAAAAAGCGAAAGCAAAATATGCGAAAG

AAGCCAAAAAGTATGCGGAGAAAGCAAAAAAGCTGAGTATAAAGCTAAA

GAAGCCGCAGAAAAGCTAAAGCTTATGCCAAAGAGGCTGCAAAAGCAGA

AGCCAAAGCTGCGAAATATGCAGCGGAAAAAGCCGCTGAGGCTGCCAAAG

CAGCCTATGCGAAAGCGGAAGCCGCAAAAGCAGCCAAAGAAGCTGCCTAC

GCCGCGAAAGCAGAAGCTGCCAAAGCGGCCTATGCCGCAGAGGCAGCCAA

AGCGGAATACGCGGCTGAAGCGGCAAAAGAGGCGGCTTACGCAGCCGCGG

AATACGCGGCCGCGGAGGCCGCGTAA.
```

The invention also provides DNA of the disclosed polypeptide of having the sequence:

```
                                          (SEQ ID NO: 9)
ATGGCAAAGAAGAAATATAAGGCGAAAGAAAAGAAGGCTAAGGCTAAGAA

GAAAGCAAAAGAGAAGAAGAAATACAAAGCCAAGAAAGAAAAGAAAGCCA

AAAAGTACAAAGAAAAGGCGGCAAAGTATAAGGCTAAAAAGGAGAAAGCG

AAAAAGGAAGCGGCTAAATACAAAAAGGCCAAAAAGTACAAAGCCGAGAA

AGCGAAATATGCGAAGGAAAAAGCAAAGAAAAAGCGAAAGCTTATGCGG

AAAAAGCGGAGAAAGCTGCAAAATATGCGGCCAAAGAAGCCAAAAAGTAT

GCGGAGAAAGCAGCTGAGAAAAAGCTGAGTATAAAGCTAAAGAAGCCGC

AGAAAAATACGCGGCTAAAGCTTATGCCGCTAAAGAGGCTGCAAAAGCAT

ATAAGGAAGCCAAAGCTGCGAAATATGCGAAAGCTGCGGAAAAAGCCGCT

GCGAAAGAGGCTGCCAAAGCAGCCTATGCGGCCAAAGCGGAAGCCGCAAA

AGAGGCAGCCAAAGAAGCTGCCTACGCCGCGGCAAAAGCAGAAGCTGCCG

CTGCGAAAGCGGCTGCCTATGCCGCAGAGGCAGCCGCTAAAGCGGAATAC

GCGGCTGAAGCGGCAGCGAAAGAGGCGGCTTACGCAGCCGCGGAATACGC

GGCCGCGGAGGCCGCGTAA.
```

The invention also provides DNA of the disclosed polypeptide of having the sequence:

```
                                         (SEQ ID NO: 10)
ATGGCGAAAAAAAAGTACAAAGCTAAGGAGAAAAAGGCGAAATATAAGGC

AAAGAAGGAGAAAAAGGCGAAAGAAAAGAAGGCTAAGAAGAAATATAAAG

CGAAGAAGAAAGCCGCTGAGAAGAAATACGCCAAAGAGAAAAAGGCGAAA

GAAAAGGCGGCAAAGAAATATAAGGCTAAAAAGGAGAAAGCGAAAAAGGA

AGCGGCTAAATACAAAAAGGCCAAAAAGTACAAAGCCGAGAAAAAGGCGA

AATATGCGGCCAAGGAAAAAGCAAAAGAAAAAGCGAAAGCTTATGCGGAA

AAAAAGGCGGAGAAAGCTGCAAAATATGCGGCCAAAGAAGCCAAAAAGTA

TGCGGAGAAAGCAGCTGAGAAAAAGCTGAGTATAAAGCTAAAGAAGCCG

CAGAAAAATACGCGGCTAAAAAGGCCGAGTATGCCGCTGAGAAAGAGGCT

GCAAAAGCATATAAGGAAGCCAAAGCTGCGAAATATGCGAAAGCTGCGGA

AAAAGCCAAAGCTGCGAAAGAGGCTGCCAAAGCAGCCTATGCGGCCAAAG

CGGAAGCCGCAAAAGAGGCAGCCAAAGAAGCTGCCTACGCCGCGGCAAAA

GCAGAAGCTGCCGCTTATGCAGCGGCCAAAGCGGCGGCTGCCTATGCCGC

AGAGGCAGCCGCTAAAGCGGAATACGCGGCTGCAGAAGCGGCAGCGAAAG

AGGCGGCTTACGCAGCCGCGGAATACGCGGCCGCGGCCGAGGCGGCTGCA

TAA.
```

The invention further provide a process for making the polypeptide of any of the disclosed DNA of the disclosed polypeptide sequences, comprising expressing under suitable conditions the polypeptide from DNA encoding the polypeptide in a suitable cell, and isolating the polypeptide so expressed. In an embodiment, the DNA consists of consecutive nucleotides having a sequence selected from the following:

```
                                          (SEQ ID NO: 6)
ATGGCCGAGAAATACAAGGCTAAGAAAGCGAAGGAAAAAGCATACAAGAA

AAAGGCCAAAGAAGCAAAAAAGGCAAAATATAAGGCTAAAGAAGCGAAAG

CGTATAAAGCAGAAAAAAGGCGAAATATGCAAAAGCAAAAGAAAAGGCT

TATGCTAAAGCCAAGGAGGCAAAAGCATACGCGAAAGCCAAAGCAAAAGC

CGAAAAGGCTAAAGCTAAAGCGAAATATGCTGAGAAAGCTAAAGCCGCGA

AGTATGCCGAAAAAGCGGCCAAATATGCGGAAGCCAAAGCAAAGGCCGCT

GAGGCAAAATATGCCGCAGAAGCTAAAGAAGCTGCGAAAGCCGCGGAAGC

AAAATACGCGGCAAAGGCAGAAGCGGCCAAATATGCCGCGGAGAAGGCCG

CGGAAAAGTATGCGAAAGCTGAAGCCGCGGCCGAGGCGAAAGAGGCGGCG

TAA;

(SEQ ID NO: 7)
ATGGCAAAGAAGAAATATAAGGCGAAAGAAAAGAAGGCTAAGAAGAAAGC

AAAAGAGAAGAAGTACAAAGCCAAGAAGGCGAAATACAAAGAAAAGGCGG

CAAAGTATAAGGCTAAAAAGGCGAAAGCTAAATACAAAGCCAAAGCCGAG

AAAGCGAAAGCTAAAGCAGAAAAAGCGAAAGCTTATGCGGAAAAAGCGAA

AGCAAAATATGCGAAAGAAGCCAAAAAGTATGCGGAGAAAGCAAAAAAG
```

-continued
CTGAGTATAAAGCTAAAGAAGCCGCAGAAAAAGCTAAAGCTTATGCCAAA

GAGGCTGCAAAAGCAGAAAAAGCTGCGAAAGCAGCGGAAAAAGCCGCTAA

GGCTTATGCGAAAGCGGAAGCCGCAGCCAAAGAAGCTGCCTACGCCGCGA

AAGCAGAAGCTAAAGCGGCCTATGCCGCAGAGGCAGCCAAAGCGGAATAC

GCGGCTGAAGCGGCAAAAGAGGCGGCTTACGCAGCCGCGGAATACGCGGC

CGAGGCGGCCTAA;

(SEQ ID NO: 8)
ATGGCAAAGAAGAAATATAAGGCGAAAGAAAAGAAGGCTAAGAAGAAAGC

AAAAGAGAAGAAGAAATACAAAGCCAAGGAAAAGAAAGCCAAAAAGTACA

AAGAAAAGGCGGCAAAGTATAAGGCTAAAAAGGCGAAAAAGGAAGCGGCT

AAATACAAAAAGGCCAAAGCCGAGAAAGCGAAATATGCGAAGGAAAAAGC

AGAAAAAGCGAAAGCTTATGCGGAAAAAGCGAAAGCAAATATGCGAAAG

AAGCCAAAAAGTATGCGGAGAAAGCAAAAAAAGCTGAGTATAAAGCTAAA

GAAGCCGCAGAAAAAGCTAAAGCTTATGCCAAAGAGGCTGCAAAAGCAGA

AGCCAAAGCTGCGAAATATGCAGCGGAAAAAGCCGCTGAGGCTGCCAAAG

CAGCCTATGCGAAAGCGGAAGCCGCAAAAGCAGCCAAAGAAGCTGCCTAC

GCCGCGAAAGCAGAAGCTGCCAAAGCGGCCTATGCCGCAGAGGCAGCCAA

AGCGGAATACGCGGCTGAAGCGGCAAAAGAGGCGGCTTACGCAGCCGCGG

AATACGCGGCCGCGGAGGCCGCGTAA;

(SEQ ID NO:9)
ATGGCAAAGAAGAAATATAAGGCGAAAGAAAAGAAGGCTAAGGCTAAGAA

GAAAGCAAAAGAGAAGAAGAAATACAAAGCCAAGAAAGAAAGAAAGCCA

AAAAGTACAAAGAAAAGGCGGCAAAGTATAAGGCTAAAAAGGAGAAAGCG

AAAAAGGAAGCGGCTAAATACAAAAAGGCCAAAAAGTACAAAGCCGAGAA

AGCGAAATATGCGAAGGAAAAAGCAAAGAAAAAGCGAAAGCTTATGCGG

AAAAAGCGGAGAAAGCTGCAAAATATGCGGCCAAAGAAGCCAAAAAGTAT

GCGGAGAAAGCAGCTGAGAAAAAGCTGAGTATAAAGCTAAAGAAGCCGC

AGAAAAATACGCGGCTAAAGCTTATGCCGCTAAAGAGGCTGCAAAAGCAT

ATAAGGAAGCCAAAGCTGCGAAATATGCGAAAGCTGCGGAAAAAGCCGCT

GCGAAAGAGGCTGCCAAAGCAGCCTATGCGGCCAAAGCGGAAGCCGCAAA

AGAGGCAGCCAAAGAAGCTGCCTACGCCGCGGCAAAAGCAGAAGCTGCCG

CTGCGAAAGCGGCTGCCTATGCCGCAGAGGCAGCCGCTAAAGCGGAATAC

GCGGCTGAAGCGGCAGCGAAAGAGGCGGCTTACGCAGCCGCGGAATACGC

GGCCGCGGAGGCCGCGTAA;

or (SEQ ID NO: 10)
ATGGCGAAAAAAAAGTACAAAGCTAAGGAGAAAAAGGCGAAATATAAGGC

AAAGAAGGAGAAAAAGGCGAAAGAAAAGAAGGCTAAGAAGAAATATAAAG

CGAAGAAGAAAGCCGCTGAGAAGAAATACGCCAAAGAGAAAAAGGCGAAA

GAAAAGGCGGCAAAGAAATATAAGGCTAAAAAGGAGAAAGCGAAAAAGGA

AGCGGCTAAATACAAAAAGGCCAAAAAGTACAAAGCCGAGAAAAAGGCGA

AATATGCGGCCAAGGAAAAAGCAAAAGAAAAAGCGAAAGCTTATGCGGAA

-continued
AAAAGGCGGAGAAAGCTGCAAAATATGCGGCCAAAGAAGCCAAAAAGTA

TGCGGAGAAAGCAGCTGAGAAAAAGCTGAGTATAAAGCTAAAGAAGCCG

CAGAAAAATACGCGGCTAAAAAGGCCGAGTATGCCGCTGAGAAAGAGGCT

GCAAAAGCATATAAGGAAGCCAAAGCTGCGAAATATGCGAAAGCTGCGGA

AAAAGCCAAAGCTGCGAAAGAGGCTGCCAAAGCAGCCTATGCGGCCAAAG

CGGAAGCCGCAAAAGAGGCAGCCAAAGAAGCTGCCTACGCCGCGGCAAAA

GCAGAAGCTGCCGCTTATGCAGCGGCCAAAGCGGCGGCTGCCTATGCCGC

AGAGGCAGCCGCTAAAGCGGAATACGCGGCTGCAGAAGCGGCAGCGAAAG

AGGCGGCTTACGCAGCCGCGGAATACGCGGCCGCGGCCGAGGCGGCTGCA

TAA.

Therapeutic Uses

Based on the data gathered, the mixture of polypeptides of the invention is contemplated for use in treating at least the same conditions as glatiramer acetate has been disclosed to treat. Specific diseases and classes of diseases are discussed below.

An autoimmune disease or disorder is one where the immune system produces autoantibodies to an endogenous antigen with consequent injury to tissues (Merck Manual of Diagnosis and Therapy (1999), Merck Research Laboratories, (Whitehouse Station, N.J.), 1061). These diseases may be either cell-mediated disease (e.g. T-cell) or antibody-mediated (e.g. B cell) disorders (U.S. Patent Application Publication No. 20020055466 A1, published May 9, 2002 (Aharoni, et al.)). Autoimmune diseases are contemplated for treatment with the composition comprising the mixture of polypeptides of the invention.

Specific autoimmune diseases contemplated for treatment with the composition comprising the mixture of polypeptides of the invention are polyarthritis, juvenile arthritis, Felty's syndrome, autoimmune hemolytic anemia, autoimmune oophoritis, autoimmune thyroiditis, autoimmune uveoretinitis, Crohn's disease, ulcerative colitis such as in inflammatory bowel disease, chronic immune thrombocytopenic purpura, contact sensitivity disease, diabetes mellitus, Graves disease, Guillain-Barre's syndrome, Hashimoto's disease (thyroiditis), idiopathic myxedema, myasthenia gravis, psoriasis, pemphigus vulgaris, rheumatoid arthritis, uveitis, lupus nephritis, CNS lupus or systemic lupus erythematosus. GA has been disclosed for use in the treatment of these diseases in, e.g. U.S. Patent Application Publication No. 20020055466 A1, published May 9, 2002 (Aharoni, et al.); U.S. Pat. No. 6,514,938 B1, issued Feb. 4, 2003 to Gad, et al.; PCT International Publication No. WO 01/60392, published Aug. 23, 2001 (Gilbert, et al.); U.S. Patent Application Publication No. 2004/0006022, published Jan. 8, 2004 (Strominger, et al.).

Inflammatory, non-autoimmune diseases are diseases which impact the central nervous system, but do not include an autoimmune component and are associated with an inflammatory response in the subject afflicted with the disease. Inflammatory, non-autoimmune diseases are contemplated for treatment with the composition comprising the mixture of polypeptides of the invention. Specific inflammatory, non-autoimmune diseases contemplated for treatment with the polypeptide mixtures of the invention are Alzheimer's disease, Parkinson's disease, HIV encephalopathy, brain tumor, glaucoma, neuropathy, dementia, central nervous system infection, central nervous system bacterial infection, meningitis, stroke, and head trauma. GA has been disclosed for use in the treatment of these diseases in, e.g. U.S. Patent Application Publication No. 20020077278 A1, published Jun. 20, 2002 (Young, et al.).

The composition of the invention is also contemplated to be useful to promote nerve regeneration or to prevent or inhibit secondary degeneration which may otherwise follow primary nervous system (NS) injury, e.g., closed head injuries and blunt trauma, such as those caused by participation in dangerous sports, penetrating trauma, such as gunshot wounds, hemorrhagic stroke, ischemic stroke, glaucoma, cerebral ischemia, or damages caused by surgery such as tumor excision.

In addition, the composition of the mixture may be used to ameliorate the effects of disease that result in a degenerative process, e.g., degeneration occurring in either gray or white matter (or both) as a result of various diseases or disorders (such as neurodegenerative diseases), including, without limitation: diabetic neuropathy, senile dementias, Alzheimer's disease, Parkinson's Disease, Huntington's disease, uveitis, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, obstructive lung disease, chronic ataxic neuropathy, ophthalmic neuropathy, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease, lipoproteinemia, epilepsy, hyperalgesia, psychosis, seizures, abnormally elevated intraocular pressure, oxidative stress, opiate tolerance and dependence. Multiple sclerosis is not considered a neurodegenerative disease in this disclosure, but rather a demyelinating disease. In addition, mixtures of this invention are contemplated to be useful for their glutamate protective aspect, i.e. for injury or disease caused or exacerbated by glutamate toxicity, for example, post-operative treatments generally, and surgical tumor removal from the central nervous system (CNS). GA has been disclosed for use in the treatment of these diseases in, e.g. U.S. Patent Application Publication No. 20020037848 A1, published Mar. 28, 2002 (Eisenbach-Schwartz) and U.S. Patent Application Publication No. 20030004099 A1, published Jan. 2, 2003 (Eisenbach-Schwartz).

Certain immune-mediated diseases contemplated for treatment with a composition comprising the polypeptide mixture of the invention are characterized by undesirable immune hypersensitivity to one or more antigens and include host-versus-graft disease (HVGD) and graft-versus-host disease (GVHD), which are exemplified, respectively, by graft rejection by the host immune system and by attack on the host by donor T cells. These diseases are a significant barrier to transplantation systems such as organ transplantations and bone marrow reconstitutions. Other immune mediated diseases that are contemplated for treatment by the polypeptide mixture of the invention include delayed-type hypersensitivity (DTH) which is associated with contact antigens such as poison ivy and poison oak and various chemicals, as well as tuberculosis, leprosy, leishmaniasis, deep fungal infections, etc. GA has been disclosed for use in the treatment of these diseases in, e.g. U.S. Pat. No. 6,514,938 B1, issued Feb. 4, 2003 to Gad, et al.; and PCT International Publication No. WO 01/60392, published Aug. 23, 2001 (Gilbert, et al.); PCT International Publication No. WO 00/27417, published May 19, 2000 (Aharoni, et al.).

Polypeptide mixtures of the invention are also contemplated as a treatment for diseases associated with demyelination of central nervous system axons such as multiple sclerosis, acute disseminated encephalomyelitis, transverse myelitis, demyelinating genetic diseases, spinal cord injury, virus-induced demyelination, Progressive Multifocal Leucoencephalopathy, Human Lymphotrophic T-cell Virus I (HTLVI)-associated myelopathy, and nutritional metabolic disorders such as vitamin B12 deficiency and central pontine-myelinolysis. GA has been disclosed for use in the treatment of these diseases in, e.g. PCT International Publication No. WO 01/97846, published Dec. 27, 2001 (Moses, et al.).

Methods of Administration

Methods of administration include all standard methods, e.g. by parenteral, intravenous, intraperitoneal, intramuscular, subcutaneous, mucosal, oral, intranasal, buccal, vaginal, rectal, intraocular, intrathecal, topical, transdermal and intradermal routes. Administration can be systemic or local.

For oral administration excipients such as lactose or milk sugars, as well as high molecular weight polyethylene glycols and the like may be used.

Liquid dosage forms for oral administration of the polypeptide mixture include pharmaceutically acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

For intraocular administration the polypeptide mixture may be formulated into pharmaceutical compositions with pharmaceutically acceptable carriers, such as water or saline and may be formulated into eye drops.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the polypeptide mixture. For buccal administration, the compositions may take the form of tablets or lozenges formulated in conventional manner. The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The polypeptide mixture may also be formulated in rectal compositions such as suppositories or retention enemas, e.g., containing conventional suppository bases such as cocoa butter or other glycerides.

For administration by inhalation, the polypeptide mixture according to the present invention is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

Pharmaceutical compositions comprising the mixture of polypeptides of the invention may optionally be administered with an adjuvant in the usual manner for immunization. Non-limiting examples of such adjuvants include alum and incomplete Freund's adjuvant. Other manners of improving the immunogenicity of the administered peptide or polypeptide include administration in the form of an aggregation or a complex with albumin or with other carriers, all as are well known to those of ordinary skill in the vaccine art. Metabolizable lipid emulsions, such as Intralipid or Lipofundin may also be used as vehicles for the Cop 1 therapy in the manner disclosed in PCT International Publication No. WO 97/02016, published Jan. 23, 1997 (Cohen et al), the entire contents of which being hereby incorporated herein by reference.

When the mixture of polypeptides of the invention is administered orally, it may be mixed with other food forms and consumed in solid, semi-solid, suspension, or emulsion form; and it may be mixed with pharmaceutically acceptable carriers, including water, suspending agents, emulsifying agents, flavor enhancers, and the like. In one embodiment, the oral composition is enterically-coated. Use of enteric coatings is well known in the art. For example, Lehman teaches enteric coatings such as Eudragit S and Eudragit L. (Lehman, K., "Acrylic Coatings in Controlled Realse Tablet Manufacturer", Manufacturing Chemist and Aerosol News, p. 39 (1973)) The Handbook of Pharmaceutical Excipients, 2.sup.nd Ed., also teaches Eudragit S and Eudragit L applications. One Eudragit which may be used in the present invention is L30D55.

The mixture of polypeptides of the invention may also be administered nasally in certain of the above-mentioned forms by inhalation or nose drops. Furthermore, oral inhalation may be employed to deliver the mixture of polypeptides of the invention to the mucosal linings of the trachea and bronchial passages.

The mixture of polypeptides can also be administered in the form of liposome delivery systems, such as small unilamellar vesicles, large unilamallar vesicles, and multilamellar vesicles. Liposomes can be formed from a variety of phospholipids, such as phosphatidylcholines, or lipids, such as cholesterol and stearylamine. The compounds may be administered as components of tissue-targeted emulsions.

Examples of liposomes which can be used in this invention include the following: (1) CellFectin, 1:1.5 (M/M) liposome formulation of the cationic lipid N,NI,NII,NIII-tetramethyl-N,NI,NII,NIII-tetrapalmity-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-trimethyl-ammoniummethylsulfate) (Boehringer Manheim); and (4) Lipofectamine, 3:1 (M/M) liposome formulation of the polycationic lipid DOSPA and the neutral lipid DOPE (GIBCO BRL).

The invention also provides a pharmaceutical pack or kit comprising one or more containers filled with one or more of the ingredients of the pharmaceutical compositions of the invention.

The mixture of polypeptides disclosed in this application, having a net positive charge, can be attached electrostatically to charged nanoparticles or nanoparticle by mixing an aqueous solution of the polypeptide mixture of the invention with a suspension of the nanoparticles or microparticles. The suspension thus formed of the polypeptide mixture attached to the nanoparticles or nanoparticle can be lyophilized to a powder for long-term storage. The lyophilized powder can be reconstituted in buffer to re-obtain the suspension of drug. Suspensions of attached drug thus obtained are particularly suited for oral delivery. If made with particles having an average diameter below 200 nm the suspension is suitable for sublingual delivery since nanoparticles can transverse the sublingual membrane. For oral delivery to the gastrointestinal tract larger nanoparticles can be used since they are the size most readily recognized by the Peyer's patches and M-cells. For such oral delivery a nano-suspension, as a lyophilized powder or as a reconstituted suspension, may be delivered to the small intestine by using an enteric coated capsule. The enhanced stability of the peptide or protein when attached in a nano-suspension formulation allows for more time for the peptide drug to be absorbed in the intestine before it is degraded by enzymes in the gastrointestinal tract. Production of nanoparticles can be achieved by methods well known in the art. An example of a nanoparticle involving glatiramer acetate is described in PCT International Publication No. WO 2005/041933.

Combination Therapies with the Polypeptide Mixture

In various embodiments, the claimed methods can encompass the administration of a therapeutically effective amount of the polypeptide mixture of the invention alone, or in combination with another therapeutic or prophylactic agent. By administration in combination, it is meant that the polypeptide mixture of the invention can be administered either substantially simultaneously with the second agent, or that the second agent can be administered in a stepwise fashion with the polypeptide mixture of the invention. Thus, in various embodiments, depending on the particular treatment regime chosen by the physician, one may administer the polypeptide mixture of the invention at the same time as the second agent, or in other embodiments, the polypeptide mixture of the invention and the second agent can be administered hours, days, or possibly even weeks apart. Alternatively, the polypeptide mixture of the invention and the second agent are administered together for a period of time, after which, administration of the second agent is discontinued while administration of the polypeptide mixture of the invention is continued. The desired treatment regime can be determined by one skilled in the art depending upon the particulars of the patient being treated, and the desired outcome.

Furthermore, in various embodiments depending on the particular treatment regime chosen by the physician, one may administer the polypeptide mixture of the invention and the second agent, when administered in a combination as described above, in lower dosages as determined by one skilled in the art. Any therapeutic or prophylactic agent useful in the treatment of the diseases for which the polypeptide mixture of the invention may be used can be the second agent according to this invention.

The polypeptide mixture of the invention can be used together with the second agent from the inception of the treatment of the patient or the mixture can be added to a treatment regimen after the patient has already been receiving the second agent for some time. Likewise, the second agent can be added to the treatment regimen after the patient received the mixture for some time. Alternatively, the mixture can be used to replace an agent when, for example, the patient's response to the agent deteriorates or when the patient experiences side effects using the other agent.

For the treatment of multiple sclerosis or its symptoms, the second agent may be glatiramer acetate (COPAXONE®), natalizumab (TYSABRI®), steroids, muscle relaxants, oral prednisone (DELTASONE®), methylprednisolone (DEPO-MEDROL®, SOLU-MEDROL®), prednisolone (DELTA-CORTEF®), dexamethasone (DECADRON®, TOBRA-DEX®, AK-TROL®, DEXPAK, MEDROL®), adreno-corticotrophic hormone (ACTH) (ACTHAR®), corticotrophin, immunosuppressants, acyclovir, azathioprine (IMURAN®), cyclophosphamide (CYTOXAN®, NEOSAR®), mitoxantrone (NOVANTRONE®), cyclosporine (SANDIMMUNE®), methotrexate, cladribine (LEUSTATINE®), interferons (AVONEX®, BETASERON®, BETAFERON®, REBIF®), laquinimod, ginko biloba, natalizumab (ANTEGREN®), alemtuzumab (CAMPATH®-1H), 4-aminopyridine (FAMPRIDINE), 3,4-diaminopyridine, eliprodil, IV immunoglobin (GAMMAGARD®, GAMMAR®-IV, GAMIMUNE® N, IVEEGAM®, PANGLOBULIN®, SANDOGLOBULIN®, VENOGLOBULIN®), ANERGIX®-MS, pregabalin, or ziconotide.

For the treatment of pain and/or altered sensation (dysaesthesia) related to multiple sclerosis, the second agent may be carbamazepine (TEGRETOL®, EPITOL®, ATRETOL, CARBATROL®), gabatentin (NEURONTIN®), topiramate (TOPAMAX®), zonisamide (ZONEGRAN®), phenyloin (DILANTIN®), desipramine (NORPRAMIN®), amitriptyline (ELAVIL®), imipramine (TOFRANIL®, IMAVATE, JANIMINE), doxepin (SINEQUAN®, ADAPIN, TRIADAPIN, ZONALON®), protriptyline (VIVACTIL®), pentozifylline (TRENTAL®), ibuprophen (ADVIL®, MOTRIN®), asprin, acetaminophen, or hydroxyzine (ATARAX®).

For the treatment of depression, anxiety, and/or insomnia related to multiple sclerosis, the second agent may be fluoxetine (PROZAC®), sertraline (ZOLOFT®, LUSTRAL®) venlafaxine (EFFEXOR XR®), citalopram (CELEXA®), parocetine (PAXIL®, SEROXAT), trazodone (DESYREL®, TRIALODINE), amitriptyline (ELAVIL®), nortriptyline (PAMELOR®, AVENTYL®), imipramine (TOFRANIL®, IMAVATE, JANIMINE), dothiepin (PROTHIADEN), lofepramine (GAMANIL), doxepin (SINEQUAN®, ADAPIN, DRIADAPIN, ZONALON®), protriptyline (VIVACTIL®), tranylcypromine (PARNATE®), moclobemide (MANERIX, AURORIX), bupropion (WELLBUTRIN SR®, AMFEBUTAMONE), nefazodone (SERZONE®), mirtazapine (REMERON®), zolpidem (AMBIEN®), alprazolam (XANAX®), temazepam (RESTORIL®), diazepam (VALIUM®), or buspirone (BUSPAR®).

For the treatment of fatigue related to multiple sclerosis, the second agent may be amantadine (SYMMETREL®), pemoline (CYLERT®), vitamin D derivatives such as alphacalcidol and calcitrol, or modafinil (PROVIGIL®).

For the treatment of urinary problems related to multiple sclerosis, the second agent may be oxybutynin (DIPTROPAN XL®), desmopressin (DDAVP®), vasopressin, tolterodine (DETROL®), carbamazepine (TEGRETOL®, EPITOL®, ATRETOL, CARBATROL®), imipramine (TOFRANIL®), bethane (URECHOLINE®), phenoxybenzamine (DIBENZYLINE®), terazosin (HYTRIN®), propantheline (PROBANTHINE), oxybutonin (DITROPAN®), hyoscyamine (URISPAS®, CYSTOPAS), baclofen (LIORESAL®), diazepam (VALIUM®), methenamine (HIPREX®, MANDELAMINE®), nitrofurantoin (MACRODANTIN®), phenazopyridine (PYRIDIUM®), or ciprofloxacin (CIPRO®).

For the treatment of psuedobulbar affect related to multiple sclerosis, dextromethorphan (NEURODEX™).

For the treatment of bowel problems related to multiple sclerosis, the second agent may be bisacodyl (DULCOLAX®, BISACOLAX), magnesium hydroxide (milk of magnesia), glycerin (SANI-SUPP®), psyllium hydrophilic mucilloid (METAMUCIL®), sodium phosphate (FLEET ENEMA®), anti-tumor necrosis factor (TNF) (INFLIXIMAB, REMICADE®), or docusate (COLACE®, THEREVAC® PLUS).

For the treatment of sexual dysfunction related to multiple sclerosis, the second agent may be sildenafil (VIAGRA®), alprostadil (PROSTIN VR, MUSE), or papaverine.

For the treatment of spasticity, clonus, and/or muscle tics related to multiple sclerosis, the second agent may be diazepam (VALIUM®), clonazepam (KLONOPIN®, RIVOTRIL), baclofen (LIORESAL®), dantrolene sodium (DANTRIUM®), Tizanidine (ZANAFLEX®, SIRDALUD), clonidine (CATAPRES®), or botulinum toxin (BOTOX®, NERUOBLOC®).

For the treatment of tremors related to multiple sclerosis, the second agent may be clonazepam (KLONOPIN®, RIVOTRIL), gabapentin (NEUROTIN®), primidone (MYSOLINE®), botulinum toxin (BOTOX®, NEUROBLOC), actazolamide (DIAMOX®), and cabidopa-levodopa (SINEMET®), or isoniazid (LANIAZID, NYDRAZID®).

For the treatment of vertigo, nausea, and/or dizziness related to multiple sclerosis, the second agent may be meclizine (ANTIVERT®, BONAMINE), dienhydrinate (DRAMAMINE®), prochlorperazine (COMPAZINE®), scopolamine (TRANSDERM®), or diphenhydramine (BENADRYL®).

For the treatment of multiple sclerosis, the polypeptide mixture of the invention can be administered with or after therapy, such as, plasmaphoresis, reflexology, or total lymphoid radiation.

For the treatment of glaucoma or its symptoms, the second agent may be glatiramer acetate (COPAXONE®), pilocarpine (PILOCAR®, ISOPTO® CARPINE, PILOPINE HS®), isoptocarpine timolol hemihydrate (BETIMOL®), timolol maleate (BLOCADREN®, COSOPT®, TIMOLIDE®, TIMOPTIC®, TIMOPTIC-XE®), betaxolol (BETOPTIC®), levobunolol (BETAGAN®), carteolol (OCUPRESS®), metipranolol (OPTIPRANOLOL®), epinephrine (EPIPEN®, EPIFRIN®, EPPY/N®), dipivefrin (PROPINE®), carbachol (ISOPTO® CARBACHOL), apraclonidine (IOPIDINE®), brimonidine (ALPHAGAN®), dorzolamide (TRUSOPT®, COSOPT®), latanoprost (ZALATAN®), travaprost (TRAVATAN®), brimatoprost (LUMIGAN®), brinzolamide (AZOPT®) potent cholinesterase inhibiters (e.g. echothiophate iodide (PHOSPHOLINE IODIDE®), demecarium, isoblurophate, carbonic anhydrase inhibitors (e.g. dichlorphenamide (DARANIDE®) or acetazolamide), mannitol, oral glycerin, and mydriatics (e.g. homatropine, cyclopentolate, phenylephrine), memantine, or atropine.

For the treatment of glaucoma, the polypeptide mixture of the invention can be administerd with or after therapy, such as, laser trabeculoplasty, filtering surgery, surgery, peripheral iridectomy, laser iridotomy, argon laser trabeculoplasty (ALT), selective laser trabeculoplasty (SLT), or neodymium (YAG laser cyclophotocoagulation).

For the treatment of inflammatory bowel disease (IBD) or its symptoms, the second agent may be glatiramer acetate (COPAXONE®), anticholinergics, diphenoxylate, loperamide, deodorized opium tincture, codeine, antibiotics, metronidazole (METROCREAM®, METROGEL®, METROGEL-VAGINAL®, METROLOTION®, METRO I.V.®, FLAGYL® I.V. RTU, FLAGYL® INJECTION, FLAGYL® ORAL, METRIC 21, PROTOSTAT, NORITATE®, and HELIDAC®), sulfasalazine (AZULFIDINE EN-TABS and ASULFIDINE), corticosteroid therapy (betamethasone (CELESTONE®, SOLUSPAN®), budesonide (ENTOCORT® EC), prednisone (DELTASONE®), methylprednisolone (MEDROL®, MEPROLONE UNIPAK, DEPO-MEDROL®, DEOJECT, DEPOPRED, DURALONE, M-PREDNISOL, MEDRALONE, SOLU-MEDROL®, DEMEDALONE) hydrocortisone (ANUSOL-HC®, CIPRO® HC OTIC, HYDROCORTONE®, COLOCORT™, CORTANE-B®, CORTEF®, CORTIC®-ND, LACTICARE®-HC, PROTOCORT®, PROCTOCREAM® HC, VYTONE®, ZOTO®-HC, ANUCORT-HC, ANUMED HC, CORT-DOME® HIGH POTENCY, HEMORRHOIDAL HC, HEMRIL-HC®. UNISERTS, PROCTOCORT®), antimetabolites, immunosuppressive therapies (e.g., azathioprine (IMURAN®), 6-mercaptopurine (PURINETHOL®), cyclosporine (GENGRAF™, NEORAL®, SANDIMMUNE®), T lymphocyte aphaeresis, 4-amino quinolines, methotrexate (RHEUMATREX®, TREXALL®)), loperamide, 5-aminosalicylic acid (5-ASA) (mesalamine) (ASACOL®, PENTASA®, CLAVERSAL®, CANASA® SUPPOSITORY, ROWASA®), balsalazide (COLAZAL®), sulfasalazine (AZULFIDINE EN-TABS®), olsalazine (DIPENTUM®), azathioprine (AZASAN®, IMURAN®), ACTH 75, ACTH 120, ®), anti-tumor necrosis factor (TNF) (INFLIXIMAB, REMICADE®), or antibiotics (e.g., ampicillin (PRINCIPEN), cefazolin).

For the treatment of IBD, the polypeptide mixture of the invention can be administered with or after therapy, such as, elemental diet, hyperalimentation, surgery, emergency colectomy, subtotal colectomy with ileostomy and rectosigmoid mucous fistula, or proctoclectomy with abdominoperineal resection.

For the treatment of Huntington's disease or its symptoms, the second agent may be glatiramer acetate (COPAXONE®), phenothiazine (chlorpromazine (THORAZINE®) 100 to 900 mg/day), butyrophenone neuroleptics (haloperidol), geldanamycin, RNA interference, trehalose, cystamine, rapamycin, glucocorticoids, nonsteroidal anti-inflammatory drugs (asprin, acetaminophen, ibuprohen (ADVIL®, MIDOL®)), omega-3 fatty acids (eicosapentaenoic acid (EPA) (LAX-101), docosahexanoic (DHA)), minocycline, folic acid, creatine, dichloroacetate, nicotinamide, riboflavin (BEVITAMEL® TABLETS, MEGA-B®, MASCOBAL® GEL, FOLGARD®, NIFREX®-150 FORTE CAPSULES, TRINSICON® CAPSULES), carnitine, tauroursodeoxycholic acid, ginko biloba, coenzyme Q10, vitamin A (MEGADOSE TABLETS, PALMITATE-A, VI-DAYLIN® ADC), vitamin C (PROFLAVANOL® 90 TABLETS, ACES® ANTIOXIDANT SOFT GELS, PERIDIN-C® TABLETS, TRINSICON® TABLETS, VI-DAYLIN® ADC), vitamin E (MEGADOSE TABLETS, UNIQUE E®, ACES® ANTIOXIDENT SOFT GELS, E-GEMS® SOFT GELS, LACTINOL-E® CREME), selenium (ACES® ANTIOXIDENT SOFT GELS), lipoic acid, arginine, mithramycin, remacemide, filuzole, lamotrigine (LAMICTAL®), memantine, gabamentin, HDAC inhibitors, retinoic acid or reserpine.

For the treatment of Amyotrophic Lateral Sclerosis (ALS) or its symptoms, the second agent may be riluzole (RILUTEK®), glatiramer acetate (COPAXONE®), baclofen, phenyloin (DILANTIN®), quinine, or amitriptyline.

For the treatment of ALS, the polypeptide mixture of the invention can be administered with or after therapy, such as, gastrostomy and noninvasive ventilation (e.g., BiPAP (bilevel positive airway pressure), or a tracheostomy and a ventilator).

2. Terms

The invention includes salts of the polypeptide mixture of the invention. As used herein, the term "salts" refers to both salts of carboxyl groups and to acid addition salts of amino groups of the peptide molecule. Salts of a carboxyl group may be formed by means well known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid, citric acid or trifluoroacetic acid. Such salts are preferably used to modify the pharmaceutical properties of the peptide insofar as stability, solubility, etc., are concerned.

The term "mixture" as used in this application in the phrase "mixture of polypeptides of the invention" means a mixture of copolymers of the amino acids comprising L-glutamic acid, L-alanine, L-tyrosine, and L-lysine, wherein some of the polypeptides of the mixture have C-terminal carboxyl groups and others have a diethylamide group instead. The polypeptide in the mixture may include residual impurities as a result of the manufacturing process. Because no reaction goes 100% to completion and, not all impurities can be totally eliminated, small amounts may remain and be present in the mixture. In general, said impurities are of the following three types:

organic impurities, i.e. polypeptides containing protected amino acid residues such as 5-BZ-L-glutamyl and/or N6-TFA-L-Lysyl residues, originating from incomplete removal of the protecting groups during the production process. In addition, the polypeptide mixture of the invention molecules may contain brominated L-tyrosyl residues, formed during production due to the presence of free bromine in the HBr/acetic acid reagent.

The molecular structures of the identified organic impurities are related to the participating monomers, i.e. starting materials. They can also be quantified and referred to as follows:

Residual trifluoroacetyl compounds (expressed as fluoride)

Residual benzylated glutamyl residues (expressed as benzyl bromide)

Residual brominated tyrosyl residues (expressed as bromotyrosine)

Unidentified organic impurities (determined by RP-HPLC): these are small molecular size polypeptides of the same origin with similar structures. These substances probably have similar response factors and the concentration (%) of each impurity can be calculated as % peak area relative to the polypeptide mixture of the invention peak area.

Residual solvents and inorganic impurities covered in the specification such as the residual solvent 1,4 dioxane, residual piperidine and heavy metals.

The term "average molecular weight" as used in this application means the molecular weight of the species of polypeptides present in the mixture in the highest relative proportion (i.e. the peak maximum) when the mixture is subjected to separation by molecular weight on an HPLC gel permeation column. This value can be obtained in several ways, e.g. from the retention time on a calibrated column; or from a correlation between the location of the peak and the location of the cochromatographed copolymer markers of defined sequence and molecular weight. Other methods of determining an average molecular weight such as by light scattering may be employed and will correspond substantially to the value obtained from the peak maximum.

The term "carrier" refers to any binder, disintegrant, glidant, sweetening agent, flavoring, or any other vehicle with which the mixture is administered. Suitable carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

The term "substantially" as used in this document means considerable in quantity or significantly great or being largely, but not wholly, that which is specified.

The term "substantially free" as used in this document means largely, but not wholly, chemically uncombined or not united with, attached to, combined with, or mixed with something specified.

The term "nanoparticle" as used in this document refers to a particle having an average diameter of 1-5000 nanometers (nm).

The term "glatiramer acetate markers" as used in this document refers to the glatiramer acetate markers disclosed in U.S. Pat. No. 6,800,287 B2, issued Oct. 5, 2004 (Gad et al.).

| Abbreviations | |
|---|---|
| BN | batch number |
| CD | circular dichroism |
| CFA | complete Freund's adjuvant |
| CFU | colony forming units |
| DP | drug product |
| DS | drug substance |
| EAE | experimental autoimmune encephalomyelitis |
| ELISA | enzyme-linked immunosorbent assay |
| EU | Endotoxins units |
| FTIR | Fourier transformed infrared absorption spectrum |
| GA | Glatiramer acetate |
| GP-HPLC | gel permeation - HPLC |
| HPLC | high performance liquid chromatography |
| IOP | intraocular pressure |
| L-Ala | L-alanine |

| Abbreviations | |
|---|---|
| L-Glu | L-glutamic acid |
| L-Lys | L-lysine |
| L-Tyr | L-tyrosine |
| MAbs | Monoclonal antibodies |
| mHz | Megahertz |
| MMS | mean maximal score |
| MSCH | mouse spinal cord homogenate |
| MW | molecular weight |
| NMR | nuclear magnetic resonance |
| P | Pressure |
| PAbs | Polyclonal antibodies |
| Ppm | parts per million |
| PBS | phosphate buffer saline |
| q.s. | quantum sufficient |
| RGC | retinal ganglion cells |
| RH | relative humidity |
| RP-HPLC | reversed phase-HPLC |
| RP-chromatography | reversed phase chromatography |
| RRT | relative retention time |
| RS | reference standard |
| RT | retention time |
| SC | Subcutaneous |
| SD | standard deviation |
| STD | Standard |
| TFA- | trifluoroacetyl- |
| TFE | trifluoroethanol |
| UV | ultra violet absorption spectrum |
| RP-HPLC | reversed phase-HPLC |

Drug Substance

The mixture of polypeptides of the invention may be represented by alternative formulae as follows:

1) Structural Formula

$$\text{Poly}[\text{L-Glu}_{12.9-15.3}, \text{L-Ala}_{39.2-46.2}, \text{L-Tyr}_{8.6-10}, \text{L-Lys}_{30-37.4} \text{DEAmide}_{0.11-0.24}] \cdot n\text{CH}_3\text{COOH}$$

The superscripts represent the molar percent range of amino acid and diethylamide residues comprising the various species in the polypeptide mixture of the invention where the sequence of the amino acid residues varies among these individual components.

n represents the number of moles of acetate per one mole of the polypeptide mixture of the invention (max. 26).

2) The "Molar Ratio" Formula

The calculations for formulae 2-5 are based on a DEA range from 700 ppm to 1500 ppm and 10% AcOH (average observed content).

The superscript values are ratios of each amino acid moles and the sum of all moles (amino acid and DEA) found after total hydrolysis of the sample.

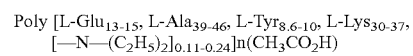

$$\text{Poly }[\text{L-Glu}_{13-15}, \text{L-Ala}_{39-46}, \text{L-Tyr}_{8.6-10}, \text{L-Lys}_{30-37}, [-\text{N}-(\text{C}_2\text{H}_5)_2]_{0.11-0.24}] n(\text{CH}_3\text{CO}_2\text{H})$$

n is the number of acetate counterions for 10% ACOH –n is 26, or 26 acetate residues per one polypeptide molecule of the polypeptide mixture of the invention.

3) The "Molar Component" Formula

The subscripts are presented as ratios between the moles of each component found and the number of moles of the polypeptide mixture of the invention subjected to analysis.

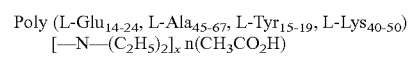

$$\text{Poly }(\text{L-Glu}_{14-24}, \text{L-Ala}_{45-67}, \text{L-Tyr}_{15-19}, \text{L-Lys}_{40-50}) [-\text{N}-(\text{C}_2\text{H}_5)_2]_x \, n(\text{CH}_3\text{CO}_2\text{H})$$

where x=0.13-0.38; i.e., 13%-38% of the molecules have a C-terminal diethylamide.

4) Hybrid Formula

Poly (L-Glu$_{13-15}$, L-Ala$_{39-46}$, L-Tyr$_{8.6-10}$, L-Lys$_{30-37}$)
[—N(C$_2$H$_5$)$_2$]$_x$ n(CH$_3$CO$_2$H)

The superscripts reflect the molar percent range of the amino acid residues; X represents the percentage of molecules with C-terminal diethylamides (13-38); n is the number of acetate counter ions per molecule (15-29). Average molecular weight: 16,000 Daltons (13,500-18,500).

5) The Alternative Structural Formula

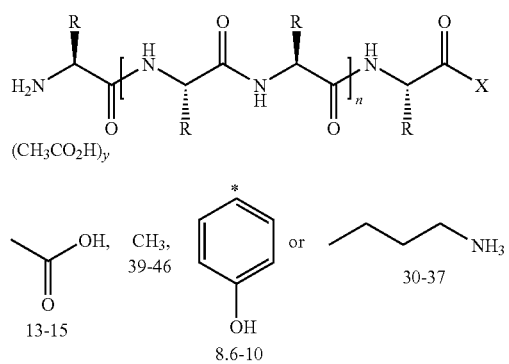

R = (on a molar percentage basis)
X = OH in 68-81% of the molecules and N(C$_2$H$_5$)$_2$ in 13-38% of the molecules;
n = 111-144; and y = 15-29.

The average molecular weight of the polypeptide mixture of the invention for all formulae can be 16,000 daltons, and in the range of 13,500-18,500 daltons.

Polypeptides with molecular weights below 5000 daltons, and in an embodiment those below 4,700 daltons, can be substantially removed from a precursor of the mixture of polypeptides of the invention by ultrafiltration.

While the polypeptide mixture of the invention and GA, the active ingredient of Copaxon®, are characterized by the same molar fraction range for each amino acid residue, other characteristics differ. Physician's Desk Reference (PDR), 56$^{th}$ ed.: Med. Econ. Co., Montvale, USA, 2002, pp. 3306-3310. The average MW of GA is 4,700 to 11,000 daltons, whereas the average MW of the polypeptide mixture of the invention is 16,000±2,500 daltons. There are also differences in chemical properties, biological activity and immunogenicity of the polypeptide mixture of the invention as compared to GA.

The preferred polypeptide mixture of the invention is the acetate salt of synthetic polypeptides prepared by chemically reacting four activated amino acid derivatives: L-Glutamic acid (L-Glu), L-alanine (L-Ala), L-tyrosine (L-Tyr) and L-lysine (L-Lys) (two of them protected i.e. 5-BZ-Glutamate derivative and 6N-TFA-Lysine derivative) in a specified ratio in the presence of a catalytic amount of diethylamine initiator.

The polypeptide mixture of the invention is preferably obtained and stored as a white to slightly yellowish lyophilized material at standard conditions.

The following analyses are typically carried out on the polypeptide mixture: Identification, Assay (on a water-free basis), Acetate Content, pH, Amino Acid Content, DEA content and molecular weight distribution.

Although the polypeptides of the polypeptide mixture of the invention consist of the same four amino acid residues as glatiramer acetate (GA), the physico-chemical and, in particular, the biological characteristics of the two drug substances differ.

In the mixture of polypeptides of the invention, 13-38% of the polypeptides have a diethylamide group at one end (instead of a carboxy group), in certain embodiments from 18-28%, whereas in GA only about 6% are diethylamides. The increased proportion of C-terminal amides is achieved by a controlled modification introduced in the manufacturing process. Thus, polypeptides in the mixture of the invention may have C-terminal carboxylic acids or C-terminal diethylamides. This may be measured by assaying formation of a diethylamine residue after totally degrading the polypeptide mixture. The amount of diethylamine residues upon degradation in the poypeptide mixture of the invention may be from 700 ppm to 1500 ppm on a water and acetate free basis.

In addition, Circular Dichroism (CD) measurements showed a distinct difference in the alpha-helical conformation of GA as compared with the polypeptide mixture of the invention.

GA and the polypeptide composition comprising the mixture of the invention share immunological cross reactivities and so the mechanism of action of the polypeptide mixture of the invention is expected to be similar to that of GA, although unexpectedly, the mixture has a higher immunologic activity. Comparative immunological and biological studies conducted with the polypeptide mixture of the invention and GA demonstrated that the polypeptide mixture of the invention induces a stronger immune response and biological activity in a mouse models for MS (EAE), and in mouse model for neurodegeneration of retinal ganglion cells.

Additionally, the mixture of polypeptides of the invention in embodiments may contain less than 1000 ppm, preferably less than 500 ppm, more preferably less than 100 ppm, or most preferably less than 10 ppm of metal ion impurities. In embodiments the mixture may contain no more than 60 ppm, preferably no more than 30 ppm, preferably no more than 20 ppm, and most preferably no more than 10 ppm, or even be substantially free of heavy metals impurities. In some embodiments the mixture contains no more than 0.10% fluorides, 0.10% polypeptides with residual trifluoroacetyl on the polypeptides, and no more than 0.10% benzyl bromide, (i.e. no more than 0.10% of benzylated glutamyl residues). In additional embodiments, the mixture contain no more than 0.5%, 0.2%, 0.1%, or 0.05% bromotyrosine; no more than 1000 ppm dioxane; and/or no more than 0.2% piperidine.

For investigational use, the drug product is supplied in a single-use, pre-filled syringe containing 1.0 ml of a clear solution of mannitol and the polypeptide mixture of the invention in different dose strengths.

Diethylamides in the Polypeptide Mixture of the Invention

During production, copolymerization of the four amino acids [L-Alanine, L-Glutamic acid, L-Tyrosine and L-Lysine] N-carboxyanhydrides is initiated by the addition of diethylamine. During this process, the diethylamine binds covalently (at which point it is referred to as diethylamide) and remains bound to the end of the polypeptide chains of the protected polypeptides as a result of formation of an amide bond where a carboxyl group would otherwise be present.

As a result of the acidolytic cleavage of the protected polypeptides, two types of polypeptide components are present in the mixture:

a) polypeptides containing the diethylamide moiety at an end thereof ("diethylamide derivatives"), b) diethylamide-free polypeptides which constitutes most of the mixture.

Consequently, in the polypeptide mixture of the invention, diethylamide derivatives are present in the drug substance and are represented in the molecular structural formula of the polypeptide mixture of the invention given above.

Chirality

The optical activity of the polypeptide mixture of the invention originates from the asymmetric centers of the four L-α amino acid residues composing the polypeptide species.

Composition Analysis

Qualitative Spectral Analysis

Proton NMR Spectrum

The proton NMR spectrum exhibits an absorption pattern characteristic of the amino acid residues composing the polypeptides of the polypeptide mixture of the invention.

TABLE 1

Proton NMR shifts (ppm) in Deuterium oxide solution of the polypeptide mixture of the invention on a Bruker 300 mHz instrument (RS)

| Shift (ppm) | Assignment |
|---|---|
| 7.09 | Tyr aromatic protons |
| 7.79 | Tyr aromatic protons |
| 4.21 | Amino acid alpha protons |
| 2.96 | Lys (—$CH_2$—N) |
| 2.27 | Glu (—$CH_2$—$CO_2$) |
| 2.08 | Tyr (—$CH_2$—Ph) |
| 1.87 | Acetate |

Figure 21:
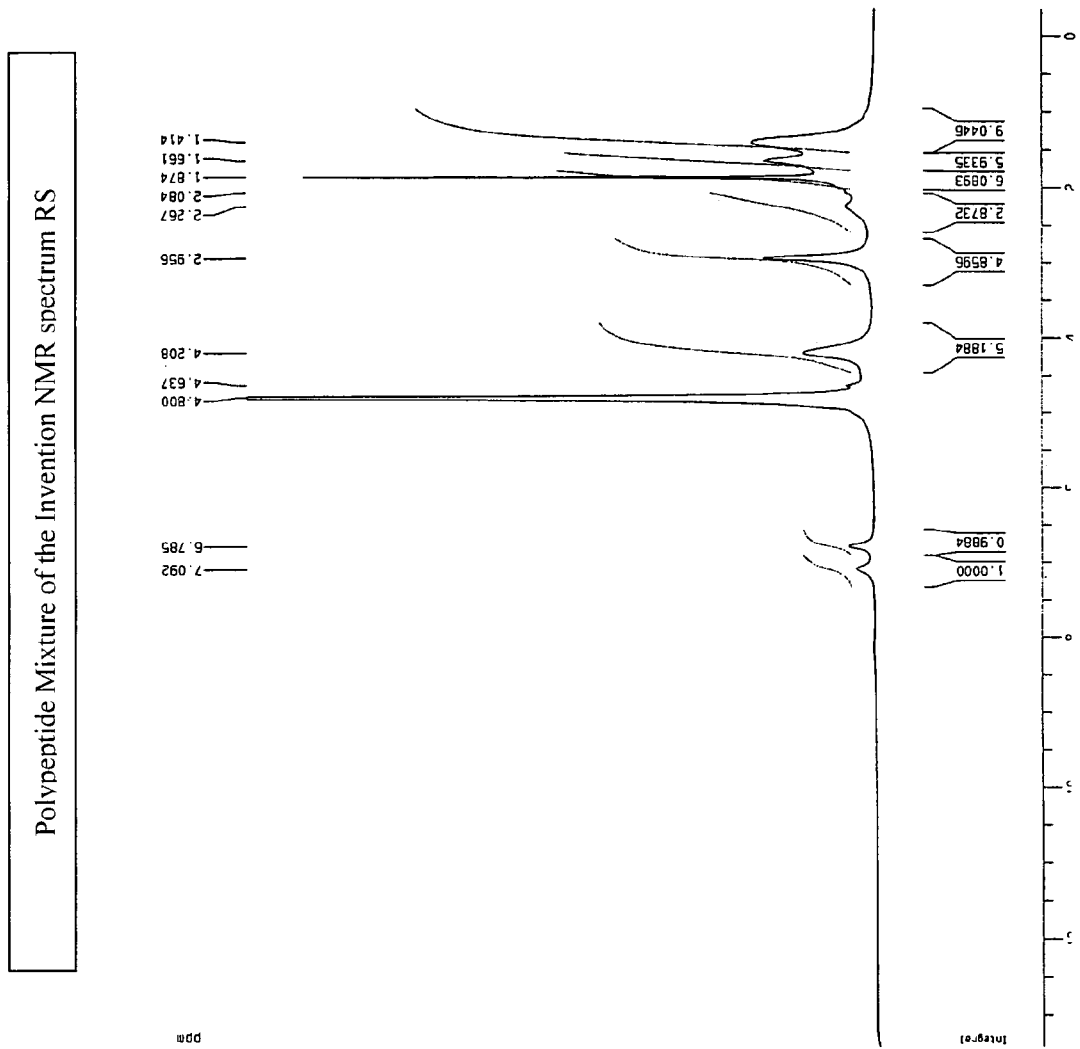
FIG. 21 NMR spectrum (RS) of the polypeptide mixture of the invention.

See also FIG. 21.

Carbon-13 NMR Spectrum

A C-13 spectrum was run on a Bruker DPX-300 instrument (300.1 for protons and 75.5 MHz, for Carbons), in $D_2O$. The chemical shifts of the carbon atoms are presented in. The C-13 shifts are characteristics of the amino acid residues present in the polypeptide mixture of the invention.

TABLE 2

$^{13}C$ chemical shifts (ppm) of the polypeptide mixture of the invention (in deuterium oxide solution) (RS)

| Chemical Shift | Assignment |
|---|---|
| 16.4 | β-Ala |
| 22.7 | γ-Lys |
| 23.8 | acetate $CH_3$ |
| 26.8 | δ-Lys |
| ca. 28 | β-Glu |
| 30.6 | β-Lys |
| 34.1 | γ-Glu |
| ca. 36 | β-Tyr |
| 39.6 | ε-Lys |
| ca. 51 | α-Ala |
| ca. 55 | α-(Lys, Glu, Tyr) |
| 115.9 | 3'-Tyr |
| 128.2 | 1'-Tyr |
| 131.0 | 2'-Tyr |
| 155.1 | 4'-Tyr |
| ca. 175 | amide carbonyls |
| 181.7 | δ-Glu |

Figure 22:
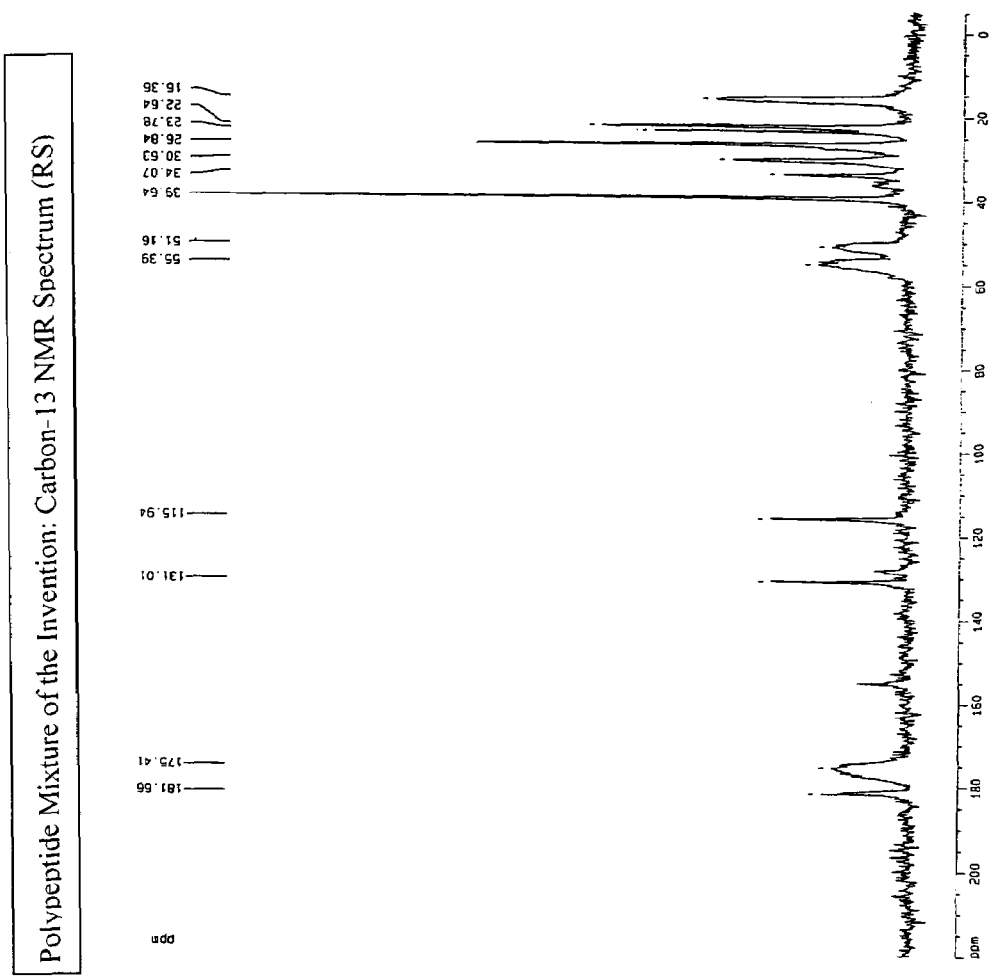
FIG. 22 Carbon-13 NMR spectrum (RS) of the polypeptide mixture of the invention.

See FIG. 22.

Ultraviolet Spectrum

The UV spectrum was measured of the polypeptide mixture of the invention (RS).

TABLE 3

UV absorption data of a 0.1 mg/mL solution of the polypeptide mixture of the invention in water

| Wavelength | Absorbance | Assignment |
|---|---|---|
| 276 | 0.135 | Π-Π* transition of tyrosyl moiety |
| 220 | Shoulder | n-Π* transition of tyrosyl moiety<br>Π-Π* transition of alpha helix conformation |
| 204 | 1.789 | n-Π* transition of C(=O)—NH |

Figure 23:
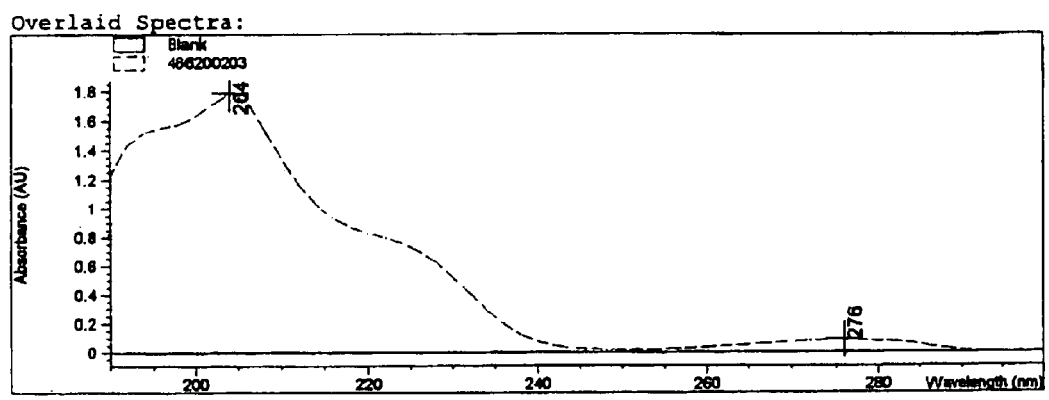
FIG. 23 Ultraviolet Spectrum of the polypeptide mixture of the invention.

The relatively high molar absorptivity at 220 nm, coupled with the relatively low molar fraction of tyrosine (0.086-0.100) in the polypeptide mixture of the invention suggests that the absorption at 220 nm is not due solely to its n-π* transition. Such absorption is also characteristic of alpha-helix regions in polypeptide molecules. The presence of alpha-helix in the polypeptide mixture of the invention has been further verified by circular dichroism measurements. See FIG. 23.

Fourier Transformed Infra Red Spectrum (FTIR)

Spectrum of the Polypeptide Mixture of the Invention (RS)

TABLE 4

IR absorption maxima of a 1% dispersion of the polypeptide mixture of the invention in KBr

| Absorption (cm$^{-1}$) | Assignment |
|---|---|
| 1655.0 | C=O stretching (amide I) |
| 1550.6 | N—H in-plane bending modified by C—N stretch |
| 1406.0 | $CO_2$" symmetric vibration |
| 1248.1 | C—N stretching mode modified by N—H in-plane bending (amide III) |

Figure 24:
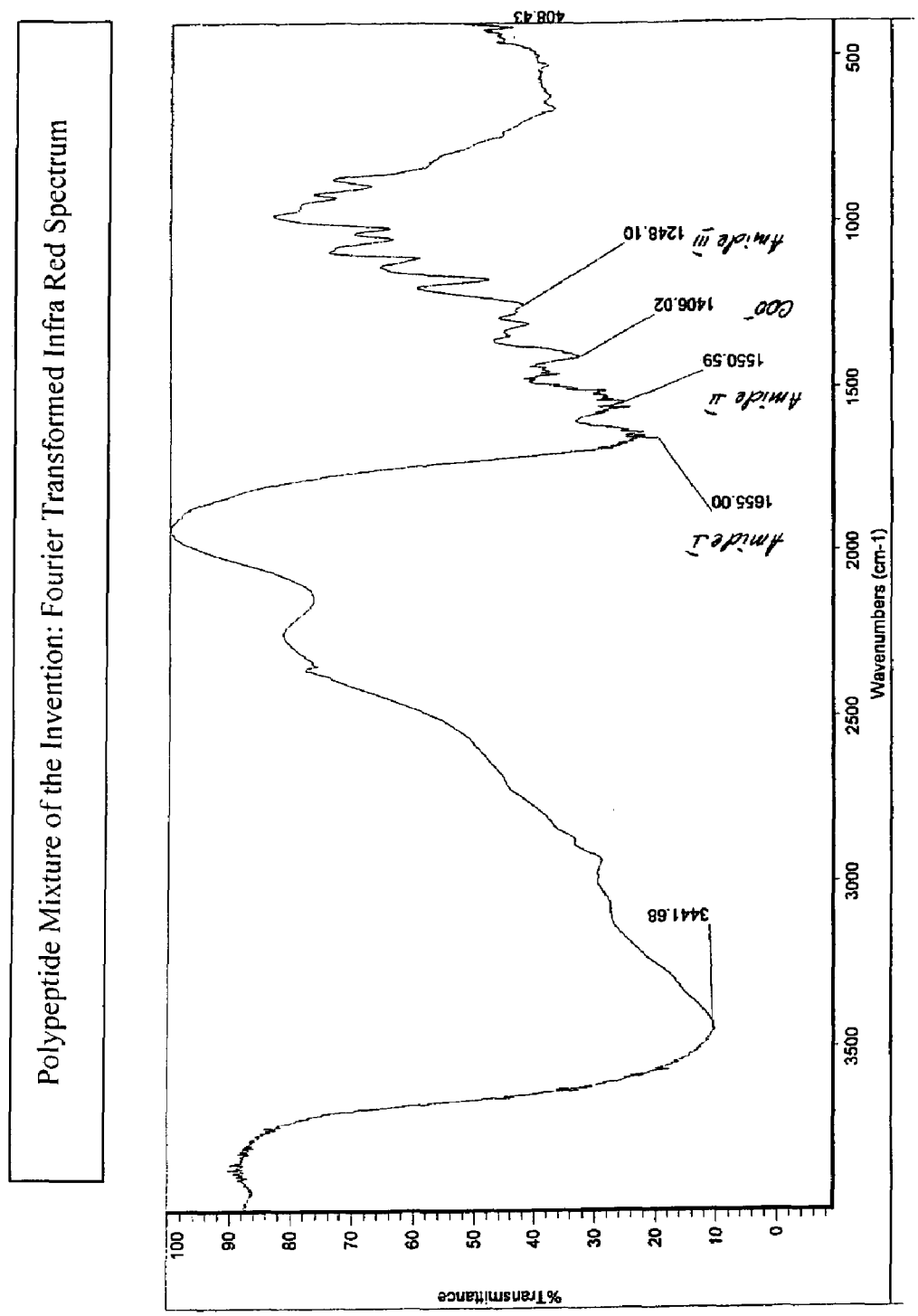
FIG. 24 Fourier transformed infra red spectrum of the polypeptide mixture of the invention FIG. 25 Graphical comparison between molecular sizes of glatiramer acetate and the polypeptide mixture of the invention.

The intensity of the amide I absorption (1655.0 cm") correlates with the degree of the α-helical conformation in the polypeptide mixture of the invention which is verified by circular dichroism measurement. See FIG. 24.

Amino Acid Content

The amino acid content was determined by a method which included quantitative hydrolysis of the sample, derivatization of the free amino acids obtained after the hydrolysis, with orthophtaldialdehyde (OPA) and 2-mercaptoethanol and analysis by RP-HPLC with UV detection at 330 nm.

TABLE 5

Amino Acid Molar Fractions in the Polypeptide Mixture of the Invention (RS)

| Amino Acid | Molar Fraction | Molar Fraction Range |
|---|---|---|
| L-Glu | 0.144 | 0.129-0.153 |
| L-Ala | 0.441 | 0.392-0.462 |
| L-Tyr | 0.091 | 0.086-0.100 |
| L-Lys | 0.324 | 0.300-0.374 |

Edman Degradation

Edman degradation is a method for step-wise sequential analysis of the amino acids composing a polypeptide, starting from the molecular N-terminus. The results of the Edman degradation indicate the specific relative occurrence (expressed in molar fraction) of the four amino acid residues comprising the polypeptides of the polypeptide mixture of the invention.

Because the mixture of polypeptides of the invention contains polypeptides of different sizes and compositions, only limited information on the amino acid residues sequence is available by a standard method of sequencing, such as Edman degradation. The average molar fraction of the amino acids between batches, as measured, is: 0.427 alanine, 0.337 lysine, 0.141 glutamate, and 0.093 tyrosine. However, the test results indicate that L-tyrosine is more prevalent at or near the N-terminus and L-lysine is more prevalent at or near the C-terminus of the polypeptides of the mixture of the invention. Furthermore, although the average molar content of alanine in GA and in the polypeptide mixture of the invention is the same, in the polypeptide mixture of the invention, the first cycle of Edman degradation show that there are fewer polypeptide molecules with alanine at the N-terminus (0.393 molecules) than in GA. Specifically, realative to the average molear content of alanine in the mixture, there are a greater percentage of polypeptide molecules with alanine at the N-terminus in GA, but a lower percentage of polypeptide molecules with alanine at the N-terminus in the polypeptide mixture of the invention.

Molecular Size

Figure 25:
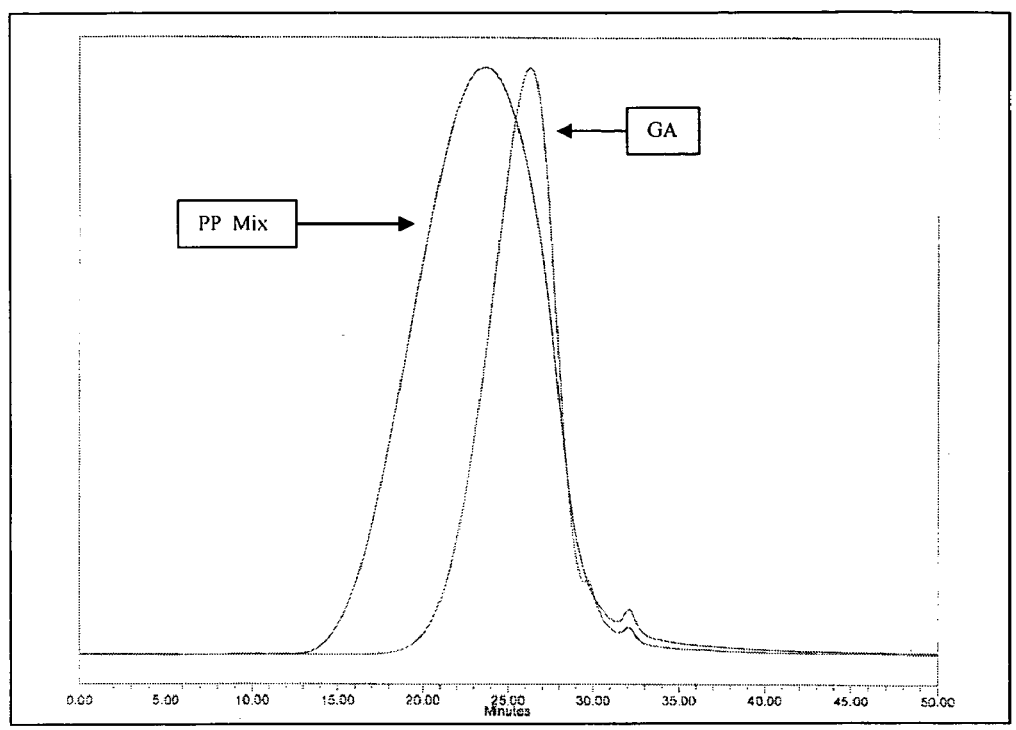

A graphical comparison between the molecular sizes of GA and the polypeptide mixture of the invention appears in FIG. 25. The difference in molecular size between a polypeptide mixture of the invention (RS) and glatiramer acetate (RS) is illustrated by their two overlaid GP-HPLC (Superose 6) chromatograms.

Diethylamide Content Analysis

The polymerization process is initiated by the reaction between diethylamine (DEA) and N-carboxamide amino acid precursors in the reaction mixture. Following the acidolytic cleavage reaction, some of the polypeptide chains retain their C-terminal diethylamides, although most of the polypeptides of the invention are cleavage products with C-terminal carboxylates. Furthermore, the ultrafiltration process removes short peptides which may have either C-terminal carboxylates or diethylamides, while the larger fragments remain in the polypeptide mixture.

In the polypeptide mixture of the invention, 13-38% of the polypeptides chains have diethylamides at the end thereof where a carboxyl is usually present (preferably 18-28%). Thus, the measured free diethylamine content, calculated on a water and AcOH free basis, may vary from 700 ppm to 1500 ppm (70-150 milligrams of diethylamine per 100 grams of polypeptide mixture).

Since neither GA nor the mixture of polypeptides of the invention contain free diethylamine, the percentage of diethylamide substituted derivatives in the polypeptide mixture is actually determined by complete hydrolysis of a sample of polypeptide mixture under strongly alkaline conditions followed by quantitation of liberated diethylamine by headspace chromatography and correction to the water and AcOH free basis.

The percentage of polypeptide chains with C-terminal diethylamides (DTP) may be calculated as follows (for convenience, the calculation is shown for 100 grams of polypeptide mixture):

$$DTP=(DEA/PP) \times 100$$

DEA=moles of diethylamine in 100 grams of polypeptide mixture calculated on the dry basis PP=moles of polypeptide in 100 grams of polypeptide mixture For example, the average molecular weight of a representative batch of a mixture of polypeptides was determined to be 16,192 Da. A 100 gram sample was found to contain 112.4 mg of diethylamine after hydrolysis (calculated on the dry basis), thus the DTP is 24.9.

Figure 26:
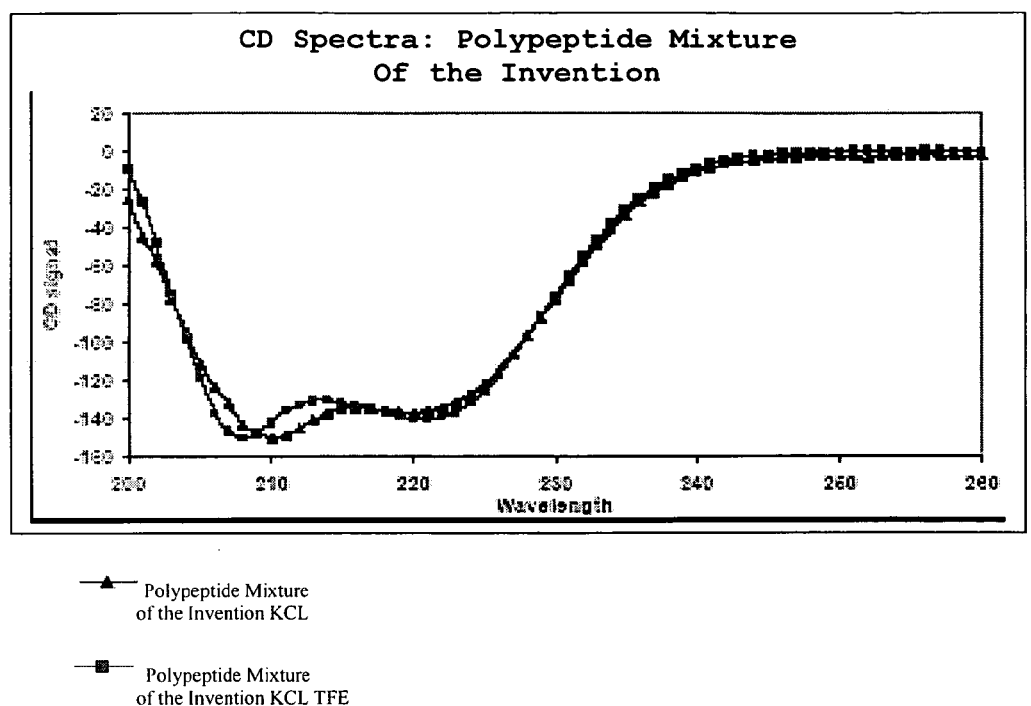
FIG. 26 Circular dichroism analysis of the polypeptide mixture of the invention.

3.5.5 Circular Dichroism (CD) Studies (See FIG. 26)

The polypeptide mixture of the invention was dissolved in phosphate buffer pH 6.8 containing potassium chloride. The initial spectra was determined in this buffer (line with triangles). Minima at about 208 and 220 nm which is characteristic of the presence of alpha-helical conformation.

Trifluoroethanol (TFE), an inducer of alpha-helical conformation was added, and the spectra were recorded. The addition of TFE caused no significant effect on the polypeptide mixture of the invention.

The minimal signal ratio is from 0.91 (solution in buffer) to 0.93 (solution in buffer+TFE). These results represent the polypeptide mixture of the invention with 97.0% of initial α-helical conformation.

On the basis of these test results, it can be concluded that the degree of alpha-helical conformation in the polypeptide mixture of the invention is apparently almost at its maximum and is not affected by the addition of TFE. Contrary to the polypeptide mixture of the invention, glatiramer acetate molecules, which have a smaller degree of alpha-helical conformation, are induced to increase this characteristic by the addition of TFE.

Molecular Weight Distribution Determination

The average molecular weight of the polypeptides in the mixture of the invention was initially determined to be approximately 15,000±2,000 daltons (by multi-angle laser scattering (MALLS). The molecular weight is now being determined by SEC-chromatography. As determined by SEC-chromatography, the same mixture of polypeptides was shown to have an average molecular weight of 16,000±2,500 daltons.

Determination of molecular weights (MW) distribution in the polypeptide mixture of the invention by SEC-chromatography requires a suitable set of MW markers. As the polypeptide mixture of the invention differs from native protein, no commercial protein MW markers could be used for this purpose and markers related to the mixture of polypeptides of the invention ("polypeptide markers") had to be produced. In order to obtain marker set for MW calibration curve, five markers were designed with MW range from about 16,000 Da to 27,000 Da (table 6). The polypeptide markers were produced by recombinant methods. The markers cDNA were sub-cloned into pET-21a vector (Merck cat# 69740) and cloned into HMS174(DE3) *E. coli* strain (Merck cat# 69453). After expression, two precipitations and two chromatography steps gave the markers in at least 80% purity.

Molecular weight determination of the markers was made using a Q-TOF Ultima Global (Micromass) mass spectrometer. Data were deconvoluted using MaxEnt 1 software. The results of molecular mass determination are summarized in Table 6.

TABLE 6

| MS analysis results vs. theoretical MW calculation | | |
|---|---|---|
| Marker # | Theoretical MW* | Measured MW |
| 1 | 15972 | 15971.6 ± 0.2 |
| 2 | 18093 | 18093.5 ± 0.2 |

TABLE 6-continued

MS analysis results vs. theoretical MW calculation

| Marker # | Theoretical MW* | Measured MW |
|---|---|---|
| 3 | 20402 | 20402.0 ± 0.3 |
| 4 | 23627 | 23627.9 ± 0.3 |
| 5 | 26662 | 26662.4 ± 0.3 |

*Theoretical MW was determined according to markers sequence

The MS analysis demonstrate that the markers for the main mass are comparable to the planned mass and all markers are without Met residue on the N' termini.

Figure 28:
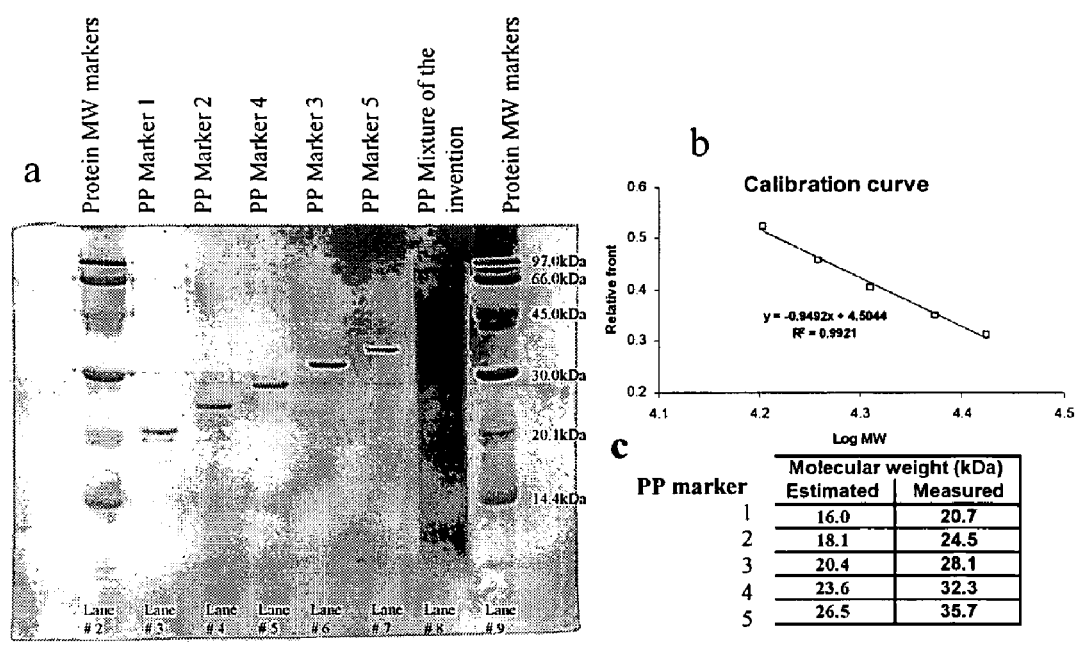
FIG. 28 a) SDS-PAGE analysis of the polypeptide markers which are used to calibrate an HPLC column for the determination of the molecular weight distribution of the polypeptide moisture of the invention; b) calibration curve showing linearity; and c) SDS-PAGE measured mass results that are about 30% higher than expected due to the use of commercial markers.

SDS-PAGE analysis was performed to estimate the markers' characteristics. About 45 μg of the mixture of polypeptides of the invention and LMW-SDS marker kit (Amersham cat # 17-0446-01), and 1 μg of each polypeptide markers were loaded on 14% gel. As shown in FIGS. 28a & 28b the markers align correctly according to their comparative mass. However, calculating the markers molecular weight based on commercially available SDS-PAGE protein markers results in a measured mass about 30% higher then their expected mass (FIG. 28c). Similar results have been experienced previously, thus accentuating the need for specific markers.

Figure 29:
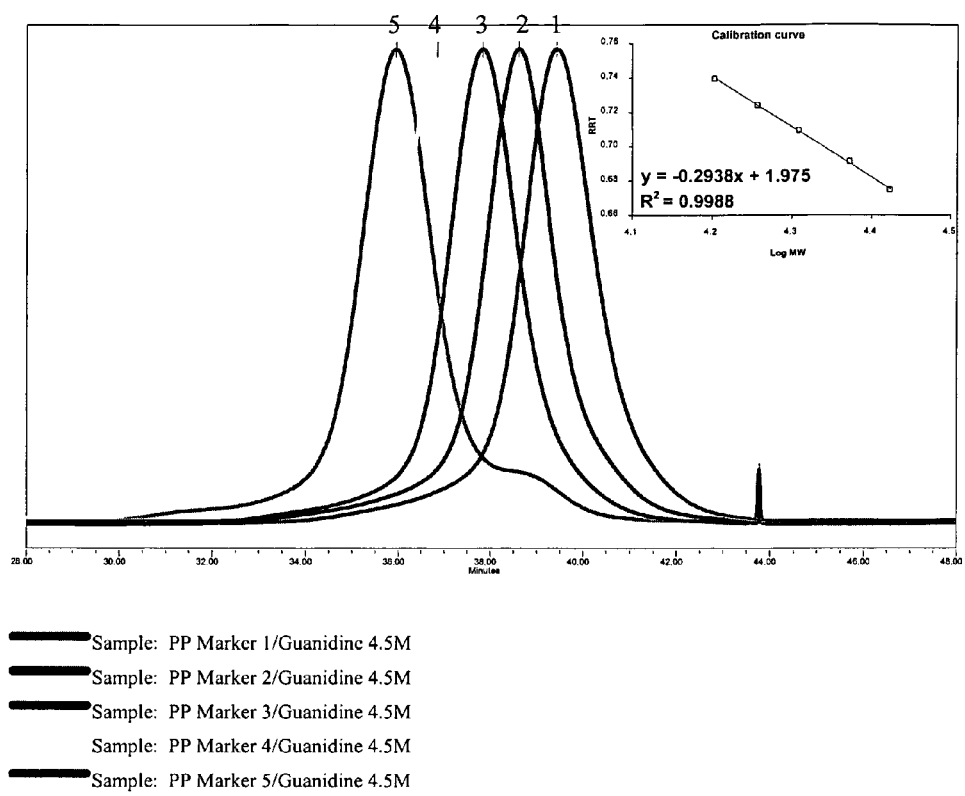
FIG. 29 Superose 6 column separation of the five polypeptide markers.

Core chromatographic conditions at which linear correlation between the markers was obtained was a flow rate of 0.4 ml/min at a guanidine HCl ("GuaHCl") concentration of 4.5 M. The linearity was maintained after the markers were lyophilized and reconstituted with water. The conditions presented nice symmetrical shape peaks with minimum tailing, $R^2$ value of 0.999 and elution time gap between polypeptide markers 1 and 5 of 3.5 min. FIG. 29.

Amino Acid Sequence of Polypeptide Markers 1-5 and the Encoding DNA

Polypeptide Marker 1:
Theoretical MW=15974

| Amino acid content | |
|---|---|
| L-Alanine (A) | 64 |
| L-Glutamate (E) | 21 |
| L-Tyrosine (Y) | 14 |
| L-Lysine (K) | 50 |

Amino acid sequence (149aa):

(SEQ ID NO: 1)
AEKYKAKKAKEKAYKKKAKEAKKAKYKAKEAKAYKAEKKAKYAKAKEKAYA

KAKEAKAYAKAKAKAEKAKAKAKYAEKAKAAKYAEKAAKYAEAKAKAAEAK

YAAEAKEAAKAAEAKYAAKAEAAKYAAEKAAEKYAKAEAAAEAKEAA

DNA sequence:

(SEQ ID NO: 6)
ATGGCCGAGAAATACAAGGCTAAGAAAGCGAAGGAAAAAGCATACAAGAA

AAAGGCCAAAGAAGCAAAAAAGGCAAAATATAAGGCTAAAGAAGCGAAAG

CGTATAAAGCAGAAAAAAGGCGAAATATGCAAAGCAAAGAAAAGGCT

TATGCTAAAGCCAAGGAGGCAAAAGCATACGCGAAAGCCAAAGCAAAAGC

CGAAAAGGCTAAAGCTAAAGCGAAATATGCTGAGAAAGCTAAAGCCGCGA

AGTATGCCGAAAAAGCGGCCAAATATGCGGAAGCCAAAGCAAACGCCGCT

GAGGCAAAATATGCCGCAGAAGCTAAAGAAGCTGCGAAAGCCGCGGAAGC

AAAATACGCGGCAAAGGCAGAAGCGGCCAAATATGCCGCGGGAGAAGGCCG

CGGAAAAGTATGCGAAAGCTGAAGCCGCGGCCGAGGCGAAAGAGGCGGCG

TAA

Polypeptide Marker 2:
Theoretical MW=18095

| Amino acid content | |
|---|---|
| L-Alanine (A) | 73 |
| L-Glutamate (E) | 23 |
| L-Tyrosine (Y) | 16 |
| L-Lysine (K) | 57 |

Amino Acid Sequence (169aa):

(SEQ ID NO: 2)
AKKKYKAKEKKAKKKAKEKKYKAKKAKYKEKAAKYKAKKAKAKYKAKAEK

AKAKAEKAKAYAEKAKAKYAKEAKKYAEKAKKAEYKAKEAAEKAKAYAKE

AAKAEKAAKAAEKAAKAYAKAEAAAKEAAYAAKAEAKAAYAAEAAKAEYA

AEAAKEAAYAAAEYAAEAA

DNA Sequence:

(SEQ ID NO: 7)
ATGGCAAAGAAGAAATATAAGGCGAAAGAAAAGAAGGCTAAGAAGAAAGC

AAAAGAAGAAGTACAAAGCCAAGAAGGCGAAATACAAAGAAAAGGCGG

CAAAGTATAAGGCTAAAAAGGCGAAAGCTAAATACAAAGCCAAAGCCGAG

AAAGCGAAAGCTAAAGCAGAAAAAGCGAAAGCTTATGCGGAAAAAGCGAA

AGCAAAATATGCGAAAGAAGCCAAAAAGTATGCGGAGAAAGCAAAAAAAG

CTGAGTATAAAGCTAAAGAAGCCGCAGAAAAAGCTAAAGCTTATGCCAAA

GAGGCTGCAAAAGCAGAAAAAGCTGCGAAAGCAGCGGAAAAAGCCGCTAA

GGCTTATGCGAAAGCGGAAGCCGCAGCCAAAGAAGCTGCCTACGCCGCGA

AAGCAGAAGCTAAAGCGGCCTATGCCGCAGAGGCAGCCAAAGCGGAATAC

GCGGCTGAAGCGGCAAAAGAGGCGGCTTACGCAGCCGCGGAATACGCGGC

CGAGGCGGCCTAA

Polypeptide Marker 3:
Theoretical MW=20404

| Amino acid content | |
|---|---|
| L-Alanine (A) | 81 |
| L-Glutamate (E) | 27 |
| L-Tyrosine (Y) | 18 |
| L-Lysine (K) | 64 |

Amino Acid Sequence (190aa):

(SEQ ID NO: 3)
AKKKYKAKEKKAKKKAKEKKKYKAKEKKAKKYKEKAAKYKAKKAKKEAAK
YKKAKAEKAKYAKEKAEKAKAYAEKAKAKYAKEAKKYAEKAKKAEYKAKE
AAEKAKAYAKEAAKAEAKAAKYAAEKAAEAAKAAYAKAEAAKAAKEAAYA
AKAEAAKAAYAAEAAKAEYAAEAAKEAAYAAAEYAAAEAA

DNA Sequence:

(SEQ ID NO: 8)
ATGGCAAAGAAGAAATATAAGGCGAAAGAAAAGAAGGCTAAGAAGAAAGC
AAAAGAGAAGAAGAAATACAAAGCCAAGGAAAAGAAAGCCAAAAAGTACA
AGAAAAGGCGGCAAAGTATAAGGCTAAAAAGGCGAAAAAGGAAGCGGCT
AAATACAAAAAGGCCAAAGCCGAGAAAGCGAAATATGCGAAGGAAAAAGC
AGAAAAAGCGAAAGCTTATGCGGAAAAAGCGAAAGCAAAATATGCGAAAG
AAGCCAAAAAGTATGCGGAGAAAGCAAAAAAAGCTGAGTATAAAGCTAAA
GAAGCCGCAGAAAAAGCTAAAGCTTATGCCAAAGAGGCTGCAAAAGCAGA
AGCCAAAGCTGCGAAATATGCAGCGGAAAAAGCCGCTGAGGCTGCCAAAG
CAGCCTATGCGAAAGCGGAAGCCGCAAAAGCAGCCAAAGAAGCTGCCTAC
GCCGCGAAAGCAGAAGCTGCCAAAGCGGCCTATGCCGCAGAGGCAGCCAA
AGCGGAATACGCGGCTGAAGCGGCAAAAGAGGCGGCTTACGCAGCCGCGG
AATACGCGGCCGCGGAGGCCGCGTAA

Polypeptide Marker 4:
Theoretical MW=23630

| Amino acid content | |
|---|---|
| L-Alanine (A) | 96 |
| L-Glutamate (E) | 30 |
| L-Tyrosine (Y) | 21 |
| L-Lysine (K) | 74 |

Amino Acid Sequence (221aa):

(SEQ ID NO: 4)
AKKKYKAKEKKAKAKKKAKEKKKYKAKKEKKAKKYKEKAAKYKAKKEKAK
KEAAKYKKAKKYKAEKAKYAKEKAKEKAKAYAEKAEKAAKYAAKEAKKYA
EKAAEKKAEYKAKEAAEKYAAKAYAAKEAAKAYKEAKAAKYAKAAEKAAA
KEAAKAAYAAKAEAAKEAAKEAAYAAKAEAAAKAAAYAAEAAAKAEYA
AEAAAKEAAYAAAEYAAAEAA

DNA Sequence:

(SEQ ID NO:9)
ATGGCAAAGAAGAAATATAAGGCGAAAGAAAAGAAGGCTAAGGCTAAGAA
GAAAGCAAAAGAGAAGAAGAAATACAAAGCCAAGAAAGAAAAGAAAGCCA
AAAGTACAAAGAAAAGGCGGCAAAGTATAAGGCTAAAAAGGAGAAAGCG

AAAAAGGAAGCGGCTAAATACAAAAAGGCCAAAAAGTACAAAGCCGAGAA
AGCGAAATATGCGAAGGAAAAAGCAAAGAAAAAGCGAAAGCTTATGCGG
AAAAAGCGGAGAAAGCTGCAAAATATGCGGCCAAAGAAGCCAAAAAGTAT
GCGGAGAAAGCAGCTGAGAAAAAGCTGAGTATAAAGCTAAAGAAGCCGC
AGAAAAATACGCGGCTAAAGCTTATGCCGCTAAAGAGGCTGCAAAAGCAT
ATAAGGAAGCCAAAGCTGCGAAATATGCGAAAGCTGCGGAAAAAGCCGCT
GCGAAAGAGGCTGCCAAAGCAGCCTATGCGGCCAAAGCGGAAGCCGCAAA
AGAGGCAGCCAAAGAAGCTGCCTACGCCGCGGCAAAAGCAGAAGCTGCCG
CTGCGAAAGCGGCTGCCTATGCCGCAGAGGCAGCCGCTAAAGCGGAATAC
GCGGCTGAAGCGGCAGCGAAAGAGGCGGCTTACGCAGCCGCGGAATACGC
GGCCGCGGAGGCCGCGTAA

Polypeptide Mixture 5:
Theoretical MW=26665

| Amino acid content | |
|---|---|
| L-Alanine (A) | 107 |
| L-Glutamate (E) | 35 |
| L-Tyrosine (Y) | 23 |
| L-Lysine (K) | 84 |

Amino Acid Sequence (248aa):

(SEQ ID NO: 5)
AKKKYKAKEKKAKYKAKKEKKAKEKKAKKKYKAKKKAAEKKYAKEKKAKE
KAAKKYKAKKEKAKKEAAKYKKAKKYKAEKKAKYAAKEKAKEKAKAYAEK
KAEKAAKYAAKEAKKYAEKAAEKKAEYKAKEAAEKYAAKKAEYAAEKEAA
KAYKEAKAAKYAKAAEKAKAAKEAAKAAYAAKAEAAKEAAKEAAYAAAKA
EAAAYAAAKAAAAYAAEAAAAKAEYAAAEAAAAKEAAYAAAEYAAAAEAAA

DNA Sequence:

(SEQ ID NO: 10)
ATGGCGAAAAAAAAGTACAAAGCTAAGGAGAAAAAGGCGAAATATAAGGC
AAAGAAGGAGAAAAAGGCGAAAGAAAAGAAGGCTAAGAAGAAATATAAAG
CGAAGAAGAAAGCCGCTGAGAAGAAATACGCCAAAGAGAAAAAGGCGAAA
GAAAAGGCGGCAAAGAAATATAAGGCTAAAAAGGAGAAAGCGAAAAAGGA
AGCGGCTAAATACAAAAAGGCCAAAAAGTACAAAGCCGAGAAAAGGCGA
AATATGCGGCCAAGGAAAAAGCAAAAGAAAAGCGAAAGCTTATGCGGAA
AAAAGGCGGAGAAAGCTGCAAAATATGCGGCCAAAGAAGCCAAAAAGTA
TGCGGAGAAAGCAGCTGAGAAAAAGCTGAGTATAAAGCTAAAGAAGCCG
CAGAAAAATACGCGGCTAAAAAGGCCGAGTATGCCGCTGAGAAAGAGGCT
GCAAAAGCATATAAGGAAGCCAAAGCTGCGAAATATGCGAAAGCTGCGGA
AAAAGCCAAAGCTGCGAAAGAGGCTGCCAAAGCAGCCTATGCGGCCAAAG
CGGAAGCCGCAAAAGAGGCAGCCAAAGAAGCTGCCTACGCCGCGGCAAAA

```
-continued
GCAGAAGCTGCCGCTTATGCAGCGGCCAAAGCGGCGGCTGCCTATGCCGC

AGAGGCAGCCGCTAAAGCGGAATACGCGGCTGCAGAAGCGGCAGCGAAAG

AGGCGGCTTACGCAGCCGCGGAATACGCGGCCGCGGCCGAGGCGGCTGCA

TAA
```

Expression and Purification of Polypeptide Markers

Synthetic DNA encoding each of the polypeptide markers of the invention was subcloned into the NdeI and SalT sites of the Pet21-a vector and transformed into *E. coli* strain HMS174 (DE3).

A 10-30 liter culture was grown and expression of the polypeptides was induced with IPTG. After 25-50 hours of fermentation, the cells were harvested and centrifuged. The pellet was resuspended with 50 mM phosphate buffer pH 2.5 and 6M urea and lysed in a Microfluidics homogenizer with cooling coil inline. The homogenate was then centrifuged and the pellet was resuspended with 50 mM phosphate buffer pH 12. The resulting suspension was centrifuged and the supernatant pH was adjusted to 8.0 with HCl. 1 mM MgCl and DNAse were added and the suspension was incubated for 2 hours at room temperature.

Chromatographic Step 1: The ammonium sulfate concentration of the suspension was adjusted to 50% and the markers were loaded on a phenyl sepharose column (Amersham). The markers were eluted from the column using a gradient of 50 mM phosphate buffer pH 8 and the peak fractions were collected.

Chromatographic Step 2: The main peak from the phenyl sepharose column was diluted with 50 mM buffer phosphate pH 8.5 and loaded on a SP-650C column (Tosoh). The markers were eluted from the column using a gradient of 50 mM phosphate buffer pH 8.5/2M NaCl and then collected, desalted and lyophilized.

Comparison of Different Molecular Weight Markers

To compare the chromatographic characters of different MW markers we tested four sets of markers: the polypeptide markers 1-5 as disclosed, Glatiramer acetate markers disclosed in U.S. Pat. No. 6,800,287 and commercially available protein markers from two vendors (sigma cat# MW-GF-70 and Amersham cat# 17-0442-01). All markers were prepared in the same fashion according to the method that was developed during this study including sample preparation with 4.5M guanidine hydrochloride.

Figure 31:
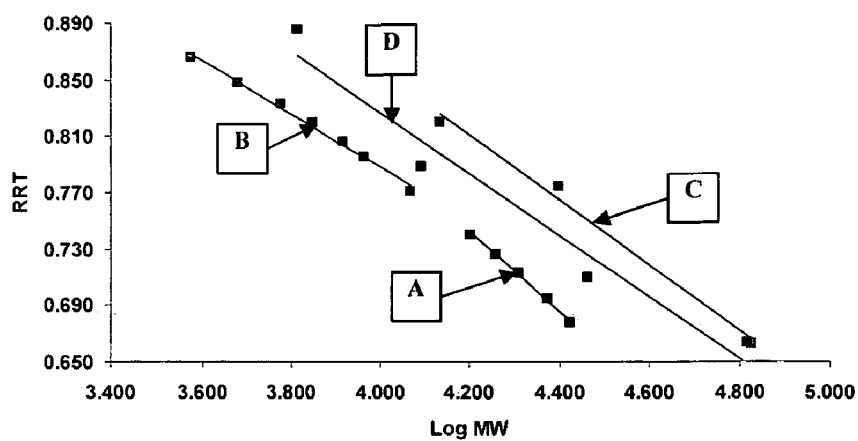
FIG. 31 Comparison of four different sets of molecular weight markers: the polypeptide markers 1-5, glatiramer acetate markers disclosed in U.S. Pat. No. 6,800,287 B2, and commercially available protein markers from two vendors, Sigma cat# MW-GF-70 and Amersham cat # 17-0442-01.

The experiments show (FIG. 31) that these polypeptide markers are almost in line with GA markers disclosed in U.S. Pat. No. 6,800,287 B2 and apparently have identical running characters. The two largest GA markers, 9200 Da and 11700 Da, form together with the polypeptide markers 1-5 an excellent linear correlation ($R^2=0.996$). The smaller GA markers seem to deviate slightly from the straight line; however the differences are most likely due to column range that wasn't designed to include samples with MW as small as the polypeptide markers. Unexpectedly, the two set of protein markers present two unrelated trend lines. The two calibration curves formed by the protein markers set are not comparable with each other and undoubtedly not with the GA markers disclosed in U.S. Pat. No. 6,800,287 B2 and polypeptide markers 1-5.

The test shows that calibrations with commercial MW markers are not comparable with the polypeptide markers 1-5. Even though the commercial markers' trend lines show slope values close to that of the other two sets, their RRT values are significantly larger compared to their MW as if they maintained some level of globular form (they appear smaller then their labeled MW compared to the polypeptide markers 1-5). In addition, under the conditions developed for running the mixture of polypeptides of the invention: one commercial marker was aggregated during preparation (Ovalbumin, Amersham 43000 Da marker), and the others show poor linear correlation.

Molecular Weight Distribution Determination of the Polypeptide Mixture of the Invention After establishing core chromatographic conditions at which linear correlation between the molecular weight markers was obtained, a preliminary experiment to determine the MW of the polypeptide mixture of the invention was performed. The experiment was carried out with the conditions using phosphate buffer pH 3 with 4.5M GuaHCl as mobile phase and 0.4 ml/min flow rate. The MW distribution results of a batch of a mixture of polypeptides of the invention were determined by "Millennium" MW calculation program based on theoretical MW values for the markers.

Figure 30:
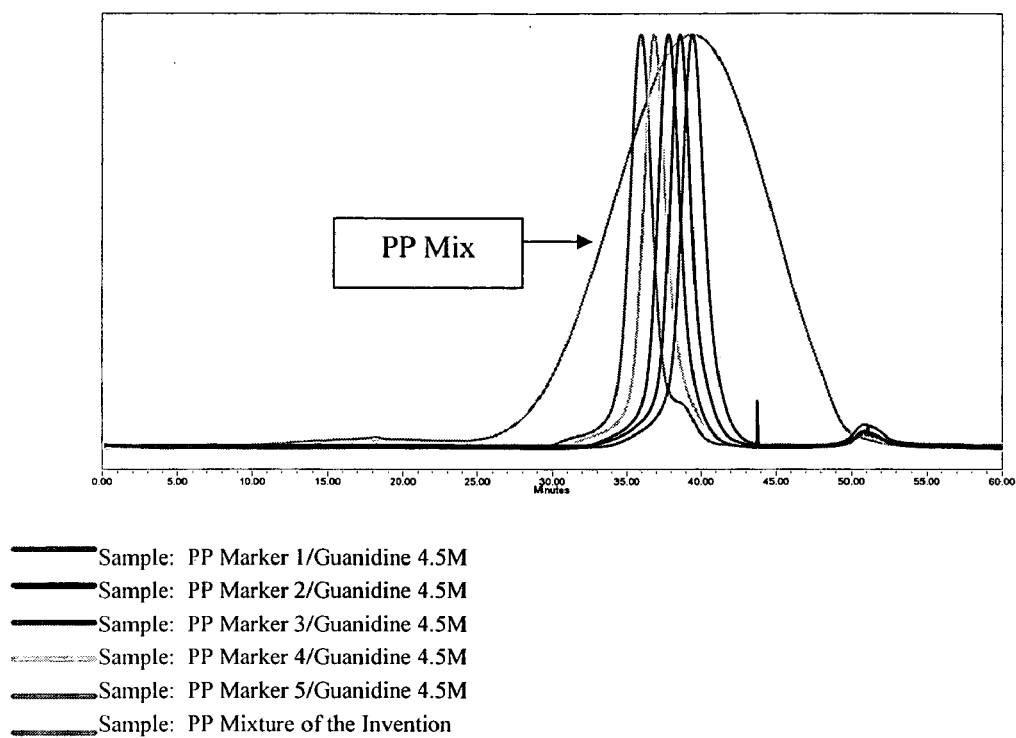
FIG. 30 Overlay of the Superpose 6 colum separation of the five polypeptide markers and the polypeptide mixture of the invention.

As shown in the overlay chromatogram of the polypeptide mixture of the invention and the polypeptide markers (FIG. 30), the markers covered the higher molecular weight region of the polypeptide mixture of the invention. The RT of polypeptide marker 1 (the lower MW marker) and the polypeptide mixture of the invention at its max were about the same. Extension of the MW range covered by markers toward the lower MW region of the polypeptide mixture of the invention can be achieved with 11700 Da and 9200 Da markers, respectively, described in U.S. Pat. No. 6,800,287 B2 for Alexander Gad et al.

Finally, the markers themselves having the four amino acid constituents of the polypeptide of the invention are contemplated as being useful for the same uses and methods as the polypeptide mixture of the invention.

Manufacturing of the Mixture of Polypeptides of the Invention

Description of the Process

Stage 1: Mixtures of Protected Polypeptides

The copolymerization of N-carboxyanhydride derivatives of the four amino acids (L-Ala, L-Glu, L-Tyr and L-Lys) in 1,4 dioxane, stirred at 25° C.±2° C. in the presence of an initiator (diethylamine) 24 hours±¼ hours to yield a mixture of protected polypeptides. The four derivatives of the amino acids used are L-Tyrosine-N-carboxyanhydride, L-Alanine-N-carboxyanhydride, 5-benzyl-L-glutamate-N-carboxyanhydride and 6N-Trifluoroacetyl-L-Lysine-N-carboxyanhydride.

Following copolymerization, process water is added and the protected polypeptides are subjected to precipitation, chopping, and dispersion for 1.25 hours. The protected polypeptides are then subjected to filtration and washing. The filter-cake is dried in a vacuum at 60° C.±5° C. at a pressure of less than 20 mmHg for 12 hours, and then subjected to milling. This yields a mixture of protected polypeptides, wherein the side chain functional groups of two amino acids (glutamic acid and lysine) are protected to avoid cross-linking.

The mixture of protected polypeptides is the first intermediate in the production of the mixtures of polypeptides of the invention.

At this stage, the sequence of amino acid residues in the polypeptides is fixed.

Stage 2: Trifluoroacetylpolypeptides

Treatment of the mixtures of protected polypeptides with a solution of 33% hydrogen bromide in glacial acetic acid at 20° C. for a time determined by a test reaction involves two chemical reactions: cleavage of the benzyl protecting group from the 5-carboxylate side chain of the glutamate residues (deprotection); and acidolytic peptide bond cleavage, reducing the average molecular size of the peptide mixture. The process water is then added, follwed by washing with stirring, decantation, filtration, and drying at 40° C.±2° C. at less than 40 mmHg, thus forming the second intermediate mixtures of trifluoroacetyl polypeptides of reduced average molecular size and weight.

The necessary reaction time is determined by a test reaction prior to the actual execution of production stage 2, directing the reaction to a target value of an average molecular weight of 16,000 daltons. The reaction time is normally 7 to 18 hours at 17-21° C. Thus, the reaction time is 7-15 hours at 18-20° C. and is ~15 hours at ~20° C.

Stage 3: Solution of a Mixture of Polypeptides of the Invention

Treatment of mixtures of trifluoroacetyl polypeptides with aqueous piperidine at 20° C.-26° C. removes the trifluoroacetyl protecting groups from the lysine residues forming a mixture of polypeptides of the invention (base). The resulting product is then subjected to filtration (less than 1.2 µm+0.2 µm) at a temperature less than 15° C. During the ultrafiltration/dilution steps, of which there may be two, low weight polypeptides formed during the first two production stages, salts and piperidine are removed by alternating the ultrafiltration/dilution cycles. After acidification with glacial acetic acid (pH 4.0-4.5) the ultrafiltration/dilution cycles are resumed, reaching pH greater than 5.5, e.g. 5.5-6, and reducing the impurity concentration to the required level. This produces the third intermediate mixture, an acidified mixture of the polypeptides of the invention in solution.

Stage 4: Drug Substance

The third imtermediate mixture is subjected to further filtration (0.2 µm), and then lypopilized. After inicital freezing (−50° C.), the freeze-drying process on the filtered solution of acidified mixture of polypeptides of the invention contained in individual trays in the lyophilizer, is continued step-wise maintaining a controlled pressure of <0.3 mbar.

Following the lyophilization, a white to slightly yellowish material is obtained, characterized by its formula as the acetate salt of the polypeptide mixture of the invention having an average molecular weight range at HPLC peak maximum 16,000±2,500 daltons, as characterized by GC-HPLC calibrated by the polypeptide markers.

The HBr Reagent

In the manufacturing process for the mixtures of polypeptides of the invention, 10%-36% hydrobromic acid in acetic acid can be used to deprotect the protected polypeptides. During the development of the production process it was found that some of the tyrosine residues in trifluoroacetyl polypeptides were brominated. This impurity was isolated and identified. The tyrosine residue was found to react with bromine to form a mono-bromotyrosine moiety comprising either 2-bromotyrosine or 3-bromotyrosine.

After much investigation the inventors discovered that the brominated tyrosine impurity was introduced into the polypeptides through free bromine in HBr/acetic acid. The free bromine was present in 33% HBr/acetic acid bought from a supplier and used in the production process. Thus, the hydrogen bromide and acetic acid solution is contemplated to have less than 500 ppm, in an embodiment less than 100 ppm, or less than 10 ppm of metal ion impurities. In an embodiment, the hydrogen bromide and acetic acid solution is free of metal ion impurities. Furthermore, in the hydrogen bromide and acetic acid solution should have less than 0.5%, 0.1%, 0.05%, 0.01%, or 0.001% of (or to be free of) free bromine and, as noted should have less than 1000 ppm of metal ion impurities.

Thus, measures were taken in order to decrease the level of free bromine in the solution. For example, pre-treatment of 33% HBr/acetic acid with a bromine scavenger was effective in removing some of the free bromine from the HBr/acetic acid solution. Furthermore, the hydrogen bromide and acetic acid solution was handled in a non-metallic reactor, such as a glass-lined or Teflon® lined reactor.

One of the bromine scavengers used in the HBr purification process was phenol. In addition to phenol, other reducing agents, such as sodium bisulfite, may be used. Phenol was chosen as a bromine scavenger because it and its reaction product with bromine (bromophenols) are both substantially non-reactive with protected polypeptides, the mixture of polypeptides of the invention, and the mixture of TFA polypeptides of the invention, and they are easy to remove from the solution during the purification process. Similarly, any bromine scavenging agent may be used provided that it and its reaction product with bromine, are not reactive with protected polypeptides, the mixture of polypeptides of the invention, and the mixture of TFA polypeptides of the invention, and it is easily removable during the final purification process.

Pharmaceutical Form and Strength

A number of different strengths of the polypeptide mixture of the invention have been developed. Immunorecognition tests in vitro by enzyme-linked immunosorbent assay (ELISA) using anti-GA (glatiramer acetate) specific monoclonal and polyclonal antibodies which show high cross reactivity with the polypeptide mixture of the invention, serve the specific identification of the polypeptide mixture of the invention. The biological activity of the material is demonstrated by the ex vivo Potency Test and the in vivo EAE Blocking Test, both carried out on mice.

One out of three regular production batches of the polypeptide mixture of the invention displaying acceptable effect in the glutamate toxicity, intra-occular pressure, and TNBS models described herein was chosen to serve as the Reference. Material.

The material was not subjected to an additional purification process for its use as Reference Standard.

Sandwich ELISA Specific Biorecognition

The biological properties of the mixture of polypeptides of the invention were evaluated by immunorecognition tests using antibodies specific to GA. The immunorecognition of the mixture of polypeptides of the invention by monoclonal and polyclonal antibodies specific to GA was examined by ELISA. Several lab scale preparations of the mixture of polypeptides of the invention were screened and the % binding of antibodies to relevant epitopes was calculated relative to GA RS (100%). Immunorecognition above 100% binding was found, up to 122% and up to 113% bidngin for poly- and mono-clonal antibodies respectively.

Figure 13:
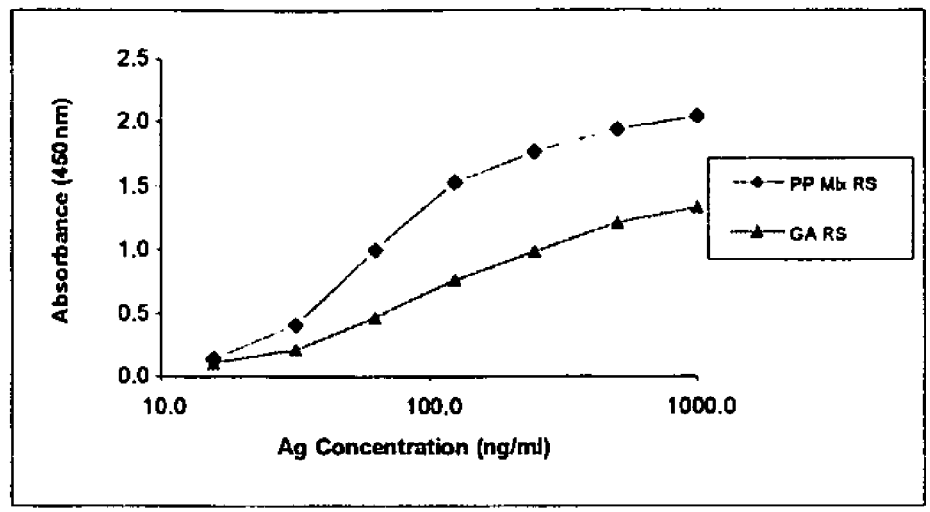
FIG. 13 Binding of GA specific monoclonal antibodies to the mixture of polypeptides of the invention and GA RS (Sandwich ELISA).
Figure 13:
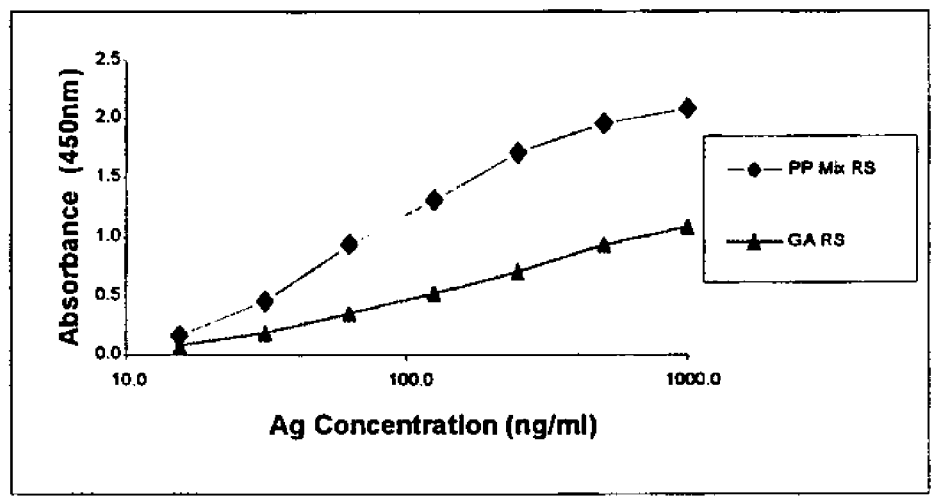

The test batches of the mixture of polypeptides of the invention were identified by GA specific antibodies, indicating that GA and the mixture of polypeptides of the invention share similar B cell epitopes and that there is cross reaction between GA and the mixture of polypeptides of the invention. However, these identification ELISA tests were not quantitative and incapable of evaluating the relative amount of epitopes, hence batches of the mixture of polypeptides of the invention do not show significantly higher binding as compared to GA RS. Consequently, a more sensitive sandwich ELISA method has been developed, enabling a more quantitative evaluation. Results of batches of the mixture of polypeptides of the invention tested by sandwich ELISA are presented in FIG. 13.

The results showed that the amount of antibodies binding to the mixture of polypeptides of the invention were higher than that to GA, indicating higher-immunorecognition, corresponding to its higher immunogenicity, as shown in the EAE models and the ex-vivo potency tests.

A microtiter plate is coated with mouse anti-Glatiramer acetate (anti-GA) monoclonal antibody (MAb) (#4B5/44 or #10F6/32). After washing the excess unbound MAbs and blocking the exposed well surface, the polypeptide mixture of the invention reference standard (RS) or the tested polypeptide mixture of the invention drug substance (DS) batches are allowed to bind the bound anti-GA MAbs. Since the polypeptide mixture of the invention contains the same amino acid residues as GA, similar antigenic determinants are presented in both polypeptides. Therefore, the peptides of the polypeptide mixture of the invention are recognized by anti-GA antibodies in a specific manner. The binding of the polypeptide mixture of the invention to the antibodies is subsequently detected by biotin-conjugated goat anti-GA polyclonal antibodies (PAbs) and streptavidin-conjugated horseradish peroxidase (HRP). The results are expressed as the average of % binding deviation of the tested the polypeptide mixture of the invention DS and GA DS batches to the antibodies, relative to the binding of the polypeptide mixture of the invention RS batch. The extent of binding correlates with the amount of "bio-recognizable" material in the tested batch relative to the RS batch.

TABLE 7

The Polypeptide Mixture Of The Invention:
Sandwich ELISA, specific biorecognition test results.

| Drug Substance (DS) Batch No. | | Data of GP-HPLC MW at HPLC peak max | Results* % Binding deviation | |
|---|---|---|---|---|
| | | | MAbs 10F6/32 | MAbs 4B5/44 |
| Polypeptide Mixture of the Invention | 1 | (16,000 ± 2,500 daltons) average for all three batches | 4% (Pass) | 9% (Pass) |
| | 2 | | 2% (Pass) | 4% (Pass) |
| | 3 | | 3% (Pass) | 3% (Pass) |
| GA | 4 | 8050 daltons | 37% (Fail)** | 47% (Fail) |
| | 5 | 8000 daltons | 35% (Fail)** | 45% (Fail) |
| | 6 | 7100 daltons | 41% (Fail)** | 46% (Fail) |

The average of the % binding deviation values should not be more than 25%
*% binding deviation relative to the polypeptide mixture of the invention RS
**significantly poorer than the polypeptide mixture of the invention The polypeptide mixture of the invention is identified by the immunorecognition test and, as shown in Table 7, this method showed high selectivity to distinguish between the polypeptide mixture of the invention and GA batches. Out of two tested polypeptide mixture of the invention batches, both batches passed (gave test results of 2-9% binding deviation), while all three GA batches failed (gave test results of 35-47% binding deviation).

The results are expressed as the average of % binding deviation of the tested polypeptide mixture of the invention or GA DS batches to the antibodies, relative to the binding of the polypeptide mixture of the invention RS batch (which is considered as 100% binding). A polypeptide mixture of the invention DS batch is considered acceptable if its average absolute % binding deviation is not more than 25%.

Relative Potency Assay

The relative potency of a batch of the polypeptide mixture of the invention is determined ex vivo, using the polypeptide mixture of the invention RS specific T cells. Mice are immunized with 250 μg of the polypeptide mixture of the invention RS in Complete Freund's Adjuvant (CFA). Nine to 11 days after immunization, the animals are sacrificed and a primary culture of lymph node (LN) cells is prepared. The cells are incubated with various concentrations of the polypeptide mixture of the invention RS and with samples of the polypeptide mixture of the invention. Following 19-21 hours of incubation at 37° C. in a humidified CO2 incubator, the culture media are collected and the levels of IL-2 are measured by ELISA. The T-cell response to each polypeptide mixture of the invention batch is tested at five concentrations (within the linear range), and for each batch the % potency relative to that of the polypeptide mixture of the invention RS batch is calculated.

TABLE 8

The Polypeptide Mixture of the
Invention: Immunological Activity Test Results.

| Drug Substance (DS) Batch No. | | MW at HPLC peak max | Potency Test* | |
|---|---|---|---|---|
| | | | Relative % Response | Pass/Fail |
| The Polypeptide Mixture of the Invention | (RS) | (16,000 ± 2,500 daltons) average for all three batches | 100% | Pass |
| | 1 | | 95.3% | Pass |
| | 2 | | 97.4% | Pass |
| GA | (RS) | 7200 daltons | 61.6% | Fail |

Relative % Response values NLT 80%
*Immunological activity relative ro the polypeptide mixture of the invention RS.

As shown in Table 8, the ex-vivo potency test showed high selectivity to distinguish between the polypeptide mixture of the invention and GA batches. Three polypeptide mixture of the invention batches passed (test results of 95.3% and 97.4%) while the GA batch failed (test result of 61.6%).

EAE Blocking Test (Acute Model in Mice)

Experimental Autoimmune Encephalomyelitis (EAE) is an autoimmune disease of the central nervous system induced in animals by immunization with central nervous system material. The encephalotogenic antigen used for EAE induction is the Mouse Spinal Cord Homogenate (MSCH). Blocking of EAE is defined as the reduction of the incidence (reduction in number of sick mice), as well as reduction in the severity of clinical signs typical of the experimental disease (Mean Maximal Score).

The maximal score of each mouse in the group was summed. The mean maximal score of a group is the average maximal score of the animals in the group. The mean maximal score of the group was calculated:

(Σ maximal score of each mouse)/number of mice in the group.

The MMS ratio is the ratio of the MMS of either the RS control group or the MMS of the group in which the batch is tested to the MMS of the EAE control group. The MMS ratio was calculated as follows:

MMS ratio=MMS of group/MMS of EAE control group

The tested batch of the polypeptide mixture of the invention is emulsified together with the MSCH in CFA, and injected into mice known to be sensitive to EAE, i.e. F1 hybrid mice of the SJL/J×BALB/C strain. Each experiment includes a negative control group (EAE induction only) and a positive control group injected with the polypeptide mixture of the invention RS in MSCH emulsion. The incidence and the clinical signs in all groups are observed and scored daily for 20 days from the 10th day post EAE induction.

The biological activity of different batches of the polypeptide mixture of the invention is determined by their ability to block the induction of EAE in mice, that is, by reducing the number of sick animals and lowering the severity of disease (clinical score).

TABLE 9

The Polypeptide Mixture of the Invention: EAE Blocking Test Results

| Batch No. | Percent Activity | Mean Maximal Score Ratio | Conclusion |
|---|---|---|---|
| 1 | 100 | 0.0 | Pass |
| 2 | 100 | 0.0 | Pass |
| 3 | 100 | 0.0 | Pass |

Furthermore, comparative immunological and biological studies conducted recently with the polypeptide mixture of the invention and GA demonstrated that the polypeptide mixture of the invention induces a stronger immune response and biological activity in mouse EAE, which is an experimental model for MS (see dose response comparison between GA and the polypeptide mixture of the invention).

Comparison between the polypeptide mixture of the invention and GA with regard to dose-response in the EAE blocking test Dose-response studies were conducted with four polypeptide mixture of the invention batches which were compared with the dose-response of GA [RS].

The release specification for the EAE blocking test defines a blocking activity of not less than 80%.

A comparison between GA and the polypeptide mixture of the invention displays the following approximate and rounded up values:

| | % Blocking activity | |
|---|---|---|
| Dose | GA | The Polypeptide mixture of the invention |
| 25 | 50 | 57 |
| 50 | 45 | 74 |
| 75 | 43 | 89 |
| 100 | 68 | 88 |
| 150 | 80 | 100 |
| 250 | 100 | 100 |

Figure 27:
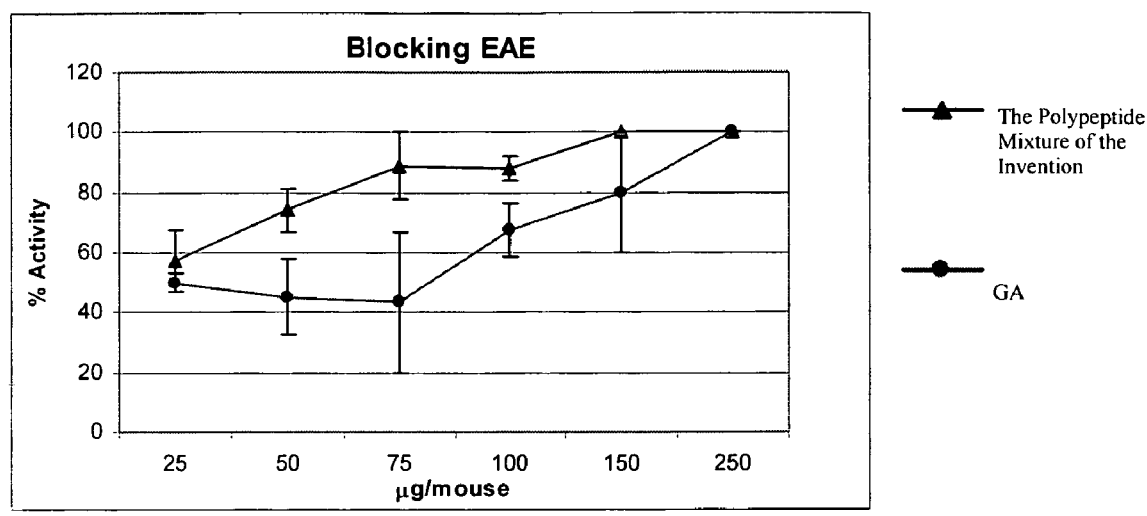
FIG. 27 Dose response of the polypeptide mixture of the invention and glatiramer acetate in the EAE blocking test.

The data indicate that the polypeptide mixture of the invention reaches the minimum blocking activity of 80% already at a dose of approximately 70 μg/mouse, while a dose of at least 150 μg/mouse of GA is needed to reach this level of activity (See FIG. 27).

4.4 Summary of Properties

The following table summarizes the physico-chemical and biological attributes of the polypeptide mixture of the invention.

TABLE 10

Properties of the exemplified mixture of polypeptides of the invention.
The Polypeptide Mixture of the Invention

| TEST | TEST RESULTS |
|---|---|
| Appearance: | White to slightly yellowish lyophilized material |
| Identification: | The IR of the polypeptide mixture of the invention |
| (by IR) | exhibits the following characteristic vibration modes |
| | amide I at 1640-1660 cm$^{-1}$ |
| | amide II at 1530-1570 cm$^{-1}$ conforms |
| | COO" at 1380-1420 cm$^{-1}$ |
| | amide III at 1240-1300 cm$^{-1}$ |
| (by UV) | The UV spectrum of the polypeptide mixture of the invention exhibits a characteristic spectrum at: |
| | Max I: about 275 nm for Aromatic Ring (Tyrosine) |
| | Max II: 195-210 nm for Amide |
| | Shoulder: 220 nm-230 nm for Tyrosine and α-helix |
| | The differences at wavelengths Max I and Max II between sample and standard solutions should not exceed ±3 nm |
| Solubility: | Readily soluble in water in acetate salt form |
| pH: | 6.0* |
| Water: | 5.3%* |
| Average Molecular Weight: (at HPLC peak maximum) | 16,000 ± 2,500 daltons |
| at −ISD (at least 84% of material) | Not more than 41,000 daltons |
| at +ISD (at least 84% of material) | Not less than 7,000 daltons |
| Amino Acid Content | Amino Acid / Molar Fraction / Total amino acid residues (on a water free basis) |
| | L-Glu 0.143   88.5%* |
| | L-Ala 0.435 |
| | L-Tyr 0.09* |
| | L-Lys 0.332 |
| Acetate Content (on a water free basis) | 9.9%* |
| Assay (on a water free basis) | 96.6%* |

TABLE 10-continued

Properties of the exemplified mixture of polypeptides of the invention.
The Polypeptide Mixture of the Invention

| TEST | TEST RESULTS | |
|---|---|---|
| Heavy Metals | LT 20 ppm* | |
| Residual Benzyl Group (Expressed as Benzyl Bromide) | LT0.10%* | |
| Bromintated Tyrosine Residues: (Expressed as Bromotyrosine) | LT 0.2%* | |
| Impurities/Degradation Products By RP Chromatography | Not more than 0.20% each Totals: NMT 0.50% | LT 0.03%* LT 0.03%* |
| Diethylamide derivatives: (Expressed as Diethylamine) | 864 ppm* | |
| Organic Volatile Impurities - residual dioxane | LT10 ppm* | |
| Residual Piperidine | LT 0.2%* | |
| Specific Optical Rotation: | $-70°$* | |
| Circular Dichroism n = 1 | Measured in: Buffer   Buffer + Trifluoroethanol 0.91       0.93 (TFE) No significant change. The α-helical conformation is initially already at its maximum i.e. (~97.0%) | |
| Immunorecognition | * | |
| Binding by polyclonal antibodies | NLT 85% | |
| Binding by two monoclonal antibodies | NLT 85% | |
| Relative Potency ex vivo | NLT 80% | |

*average of 3 batches

Pharmaceutical Development

Hypak® Pre-filled Syringes

In this example, the polypeptide mixture of the invention is a sterile solution packaged in Hypak® pre-filled syringes intended for subcutaneous injection. The composition of the drug product is outlined in the following table:

TABLE 11

Quantitative Composition of The Polypeptide Mixture of the Invention Injection

| Name of Ingredient | Unit Dose mg/ml | Unit Dose mg/ml | Unit Dose mg/ml | Unit Dose mg/ml |
|---|---|---|---|---|
| the Poly Peptide Mixture of the Invention | 5 mg | 15 mg | 30 mg | 50 mg |
| Mannitol | 50 mg | 45 mg | 40 mg | 35 mg |
| Water for Injection | q.s. 1.0 ml | q.s. 1.0 ml | q.s. 1.0 ml | q.s. 1.0 ml |

The above listed four different dose sizes of the polypeptide mixture of the invention drug product have been prepared to be applicable in different clinical studies, e.g. for the treatment of inflammatory and neurodegenerative diseases.

Iso-osmotic Formulation

The goal was to develop an iso-osmotic formulation of the polypeptide mixture of the invention at concentrations of 15 and 30 mg/ml in Mannitol solution, with pH in the range of 5.5 to 8.5, which is suitable for a parenteral application.

The following table summarizes data of experimental batches of the polypeptide mixture of the invention Drug Product.

TABLE 12

Experimental Composition of The Polypeptide Mixture of the Invention Injection

| Excipient | Amount of the polypeptide mixture of the invention dissolved | pH of solution | Solubility | Assay, % | Osmol/kg |
|---|---|---|---|---|---|
| Mannitol 45 mg/ml | 15 mg/ml | 7.2 | Clear solution | Not performed | 0.300 |
| Mannitol 40 mg/ml | 30 mg/ml | 7.4 | Clear solution | before filtration 98.9% after filtration 102.0% | 0.296 |

Due to the chemical similarity between the polypeptide mixture of the invention and glatiramer acetate, mannitol was chosen as the suitable excipient as it is in use for the production of the Copaxone® drug products.

Three sets of the 15 mg and 30 mg doses of the drug product, i.e. a total of six batches, were manufactured from three different lots of active drug substance for the initial development in order to study the stability of the formulation kept under long term and accelerated storage conditions.

Ampoules

The following table lists the polypeptide mixture of the invention Injection development lots manufactured, filled and fuse-sealed in 1 mL USP Type I colorless glass ampoules, under full aseptic conditions in the ampoule filling suite of the sterile manufacturing facility, Teva Pharmaceutical Industries Ltd. Kfar-Sava, Israel. The procedures used for the compounding and sterilizing filtration were similar to those in use for Copaxone®. These lots of the polypeptide mixture of the invention solution were stored in fuse-sealed 1 mL USP Type I colorless glass ampoules to eliminate a possible effect of the syringe and its rubber stopper on the stability of the solution. The ampoules were tested for time zero and placed on hold under long term conditions (2° C.-8° C.) for up to 24 months. These samples will serve as controls, whenever needed.

Drug Product Stability Testing

Storage conditions were as follows:

| Storage Conditions | Test Intervals |
|---|---|
| Long term testing | |
| 2° C.-8° C. | 0, 3, 6, 9, 12, 18, and 24 months |
| Accelerated testing | |
| 25 ± 2° C./60 ± 5% RH | 0, 1, 2, 3, and 6 months |

The stability was evaluated by physical-(color, clarity and particulate matter), physico-chemical-(pH, assay, and impurities/degradation products), microbiological-(sterility, bacterial endotoxins), biological (EAE), abnormal toxicity test (safety) and functional tests.

All physico-chemical, biological and microbiological parameters of the drug product studied for the proposed packaging systems remained within specifications for each storage condition during the listed test period.

Biological Testing

EXAMPLE 1

Biological Effect Evaluation

EAE Test with Preparation of Different Average Molecular Weight

Several laboratory scale preparations (7 gr. each) of increasing average molecular weight (~12,000 Daltons-20,000 Daltons) were produced and their biological activity was tested in EAE models (acute and chronic), and the ex vivo potency test. In this test only the average molecular weight is indicated by MALLS.

In EAE models the clinical score was expressed using daily mean score or mean maximal score parameters. These parameters showed the severity of clinical signs typical of the experimental disease. The incidence and the clinical signs in all groups were observed and scored daily for 20 days from the 10th day post EAE induction, values ranging from 0 for normal behavior to 5 for death. Daily mean score was the mean of scores of all mice in a test group on a given day. Mean maximal score was the sum of maximal scores of all mice in a test group divided by number of mice in the group.

The biological activity of the different preparations was determined by their ability to block the induction of EAE in mice by reducing the number of sick animals and lowering the severity of disease (clinical score).

Figure 10:
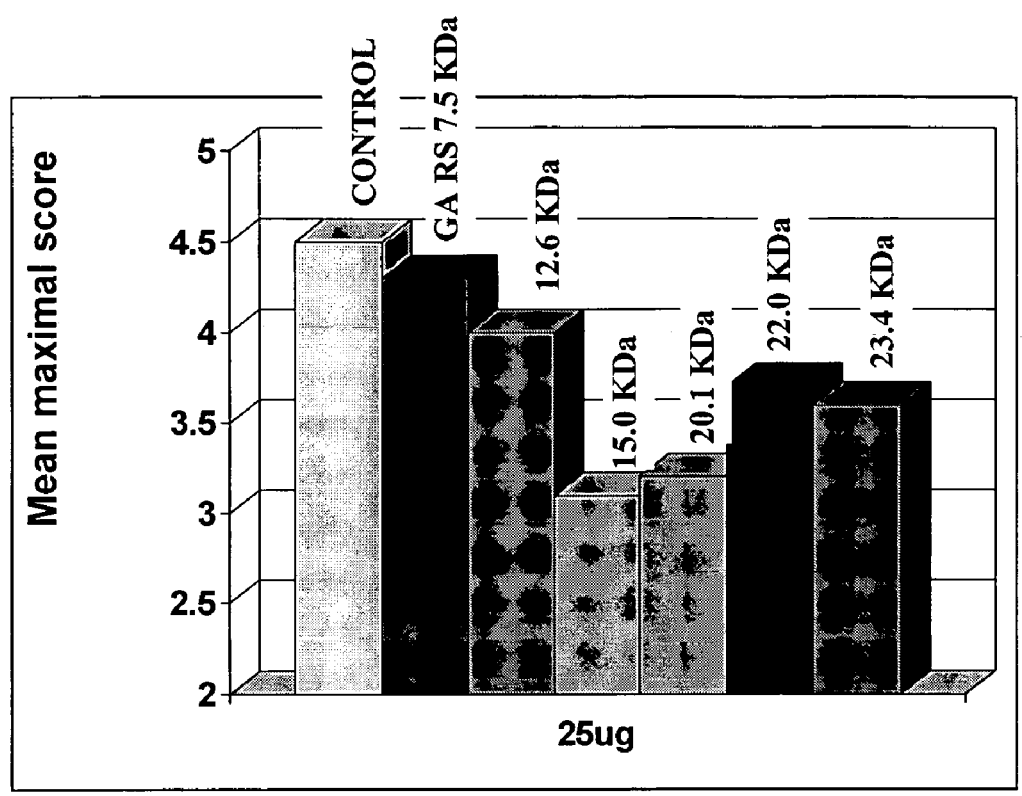
FIG. 10 Mean Maximal Score in Acute EAE in mice, GA vs. batches of polypeptide mixtures of different average molecular weight [KDa=kilodalton].

The preparations of increasing MW were tested in the EAE blocking model (acute). Mice were treated with 25 μg/mouse of either GA or the preparations. The animals were observed over the following 20 days and their daily clinical score was recorded. The experiment compared the EAE blocking activity of the five experimental preparations differing by their molecular weight, and GA RS (FIG. 10).

Figure 11:
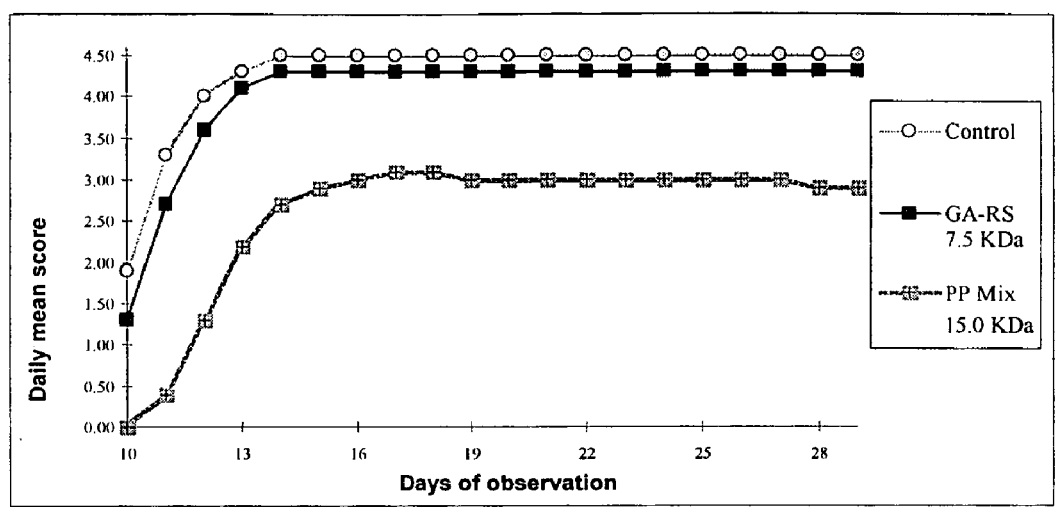
FIG. 11 Daily Mean Score in Acute EAE in mice, GA RS (7.5 KDa) vs. the mixture of polypeptides of the invention (16 KDa).

The results demonstrated the effect of increase in MW on biological activity. At the dose of 25 μg/mouse, GA blocking activity was suboptimal while preparations with MW ranging between 15 and 20 KDa (as determined by MALLS) were more effective in inhibiting acute EAE. See FIG. 11.

MOG-induced EAE (Chronic Model)

In this model the encephalitogenic antigen used for EAE induction was Myelin Oligodendrocyte Glycoprotein (MOG). The encephalitogenic emulsion (MOG+CFA enriched with 5 mg/mL MT) was injected s.c in the right flank of C57BL/6J mice. Concomitantly, pertussis toxin was injected intraperitoneally at a volume dose of 0.1 mL/mouse. Pertussis toxin injection was repeated after 48 hours. A boost of the encephalitogenic emulsion (MOG+CFA enriched with 5 mg/mL MT) was injected sc in the left flank one week later. The mixture of polypeptides of the invention was administered daily, beginning on the first day of clinical sign appearance, until day 30 post immunization.

Figure 9:
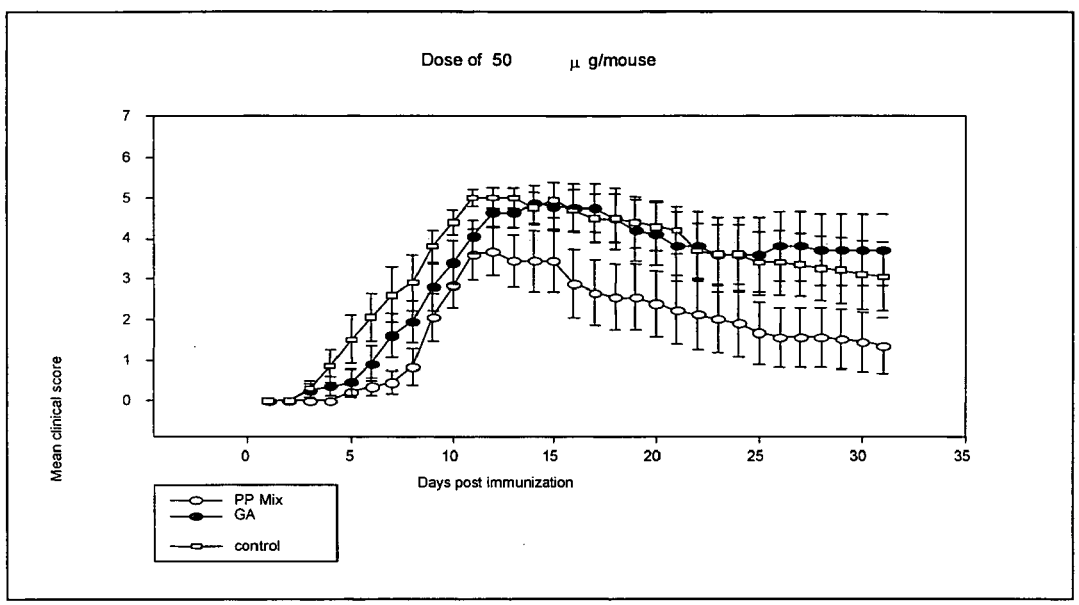
FIG. 9 MOG-induced EAE in mice, GA vs. the mixture of polypeptides of the invention.

The effect of the preparations on chronic MOG-induced EAE (a chronic EAE model where EAE was induced using myelin oligodendrocyte glycoprotein) was compared to that of GA. The results presented in FIG. 9 show that at the dose of 50 μg/mouse, GA (7.5 daltons) is not effective, while the mixture of polypeptides of the invention (~16.0 k daltons) had a significant inhibitory effect.

Biological Effect Evaluation as a Function of Dose Used

Figure 12:
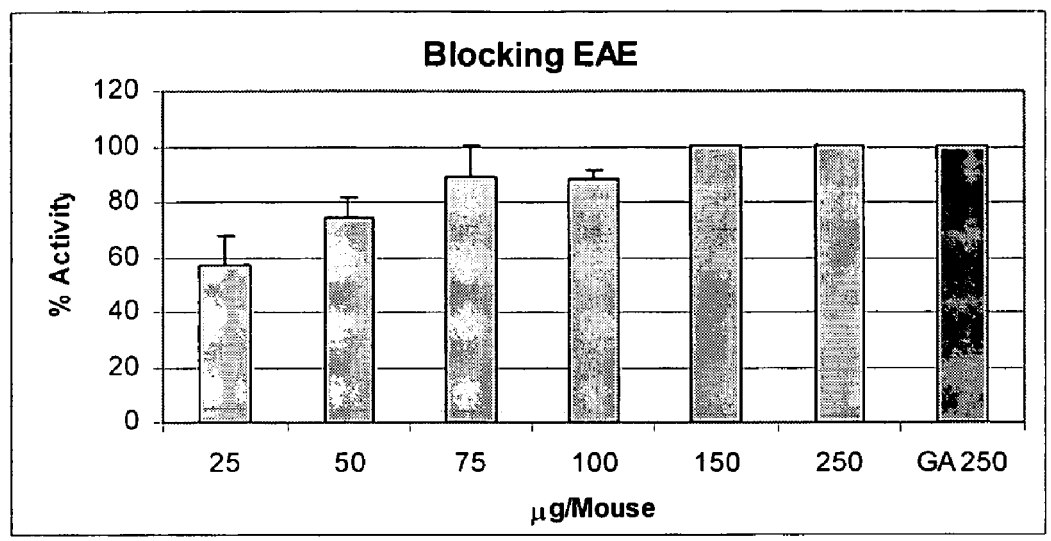
FIG. 12 Dose response of the activity the mixture of polypeptides of the invention in blocking EAE in mice, different dose levels of the mixture of polypeptides of the invention vs. 250 µg/mouse GA RS [average molecular weight of the mixture of polypeptides of the invention ~16.0 Kda].

Dose-response studies with GA RS and the mixture of polypeptides of the invention (~16,000 Daltons) were conducted in the EAE blocking test in mice. The results are presented in FIG. 12.

The results show that, at a dose as low as 75 μg/mouse the mixture of polypeptides of the invention showed 89% activity, and at a dose of 150 μg/mouse, the EAE suppressive activity of the mixture of polypeptides of the invention was equal to that induced by GA RS at 250 μg/mouse (100%), in agreement with the higher immunologic activity of the mixture of polypeptides of the invention. (In dose-response experiments with GA RS, GA batches exerted 100% blocking activity in the 150 μg/mouse dose range.)

EXAMPLE 2A

Single Injection of GA and the Mixture of Polypeptides of the Invention

Intravitreal Glutamate-Induced Toxicity in Mice

Using the model of induced cytotoxicity in mouse optic nerve, studies were conducted to test the potential neuroprotective properties of the mixture of polypeptides of the invention. An insult was induced in mice by intravitreal injection of glutamate at a concentration previously shown to lead to RGC death that is measurable after one week. On the day of glutamate injection (Day 0) male C57BL/6J mice aged 1.5-2 months were anesthetized and each animal's right eye was punctured with a 27-gauge needle in the upper portion of the sclera. Next, a Hamilton syringe with a 30-gauge needle was inserted as far as the vitreal body and a total volume of 1 μl (200 nmol) of L-glutamate dissolved in saline was injected. Four days after the glutamate injection, the mice were anesthetized and a retrograde neurotracer dye (FluoroGold) was injected stereotactically into the superior colliculus of each hemisphere. From the superior colliculus the dye is retrogradely transported into RGCs. Three days later the animals were sacrificed, their eyes enucleated, and the retinas detached, fixed in paraformaldehyde and whole mounted on filters. Labelled cells from four selected fields of identical size were counted. The selected fields were located at approximately the same distance from the optic disk to overcome the variation in RGC density as a function of distance from the optic disc. RGCs were counted under a fluorescent microscope and the average number of RGCs per field in each retina was calculated. The RGC count in a number of uninjured contralateral retinas was used as "healthy control" for the purpose of calculating % Toxicity. For each mouse, the degree of neuronal toxicity induced by the glutamate insult was calculated as follows:

$$\% \text{ Toxicity} = 100 - \left( \frac{RGC\ Count_{Glutamate\ Insult}}{RGC\ Count_{Healthy\ Control}} \right) \times 100$$

The following calculation was used to determine mean percentage of neuronal protection observed in each immunized treatment group of mice:

$$\% \text{ Protection} = \left( \frac{\%\ Toxicity_{Control\ Group} - \%\ Toxicity_{Treated\ Group}}{\%\ Toxicity_{Control\ Group}} \right) \times 100$$

Statistical significance between groups was determined using Student's t-test.

A set of mouse studies was conducted in order to investigate whether a single injection treatment (immunization) with GA and the mixture of polypeptides of the invention would protect RGCs from glutamate-induced toxicity. The following is a list of the pre-insult treatment groups to which the mice were assigned across the set of investigations. The combined number of animals included in each group across the set of investigations is indicated in parentheses:

1) 25 µg/mouse of the mixture of polypeptides of the invention administered on Day −7 before the glutamate insult. (n=15)
2) 75 µg/mouse of the mixture of polypeptides of the invention administered on Day −7 before the glutamate insult. (n=22)
3) 75 µg/mouse GA administered on Day −7 before the glutamate insult. (n=91)
4) No pretreatment administered ("toxicity control"). (n=84)

Figure 2:
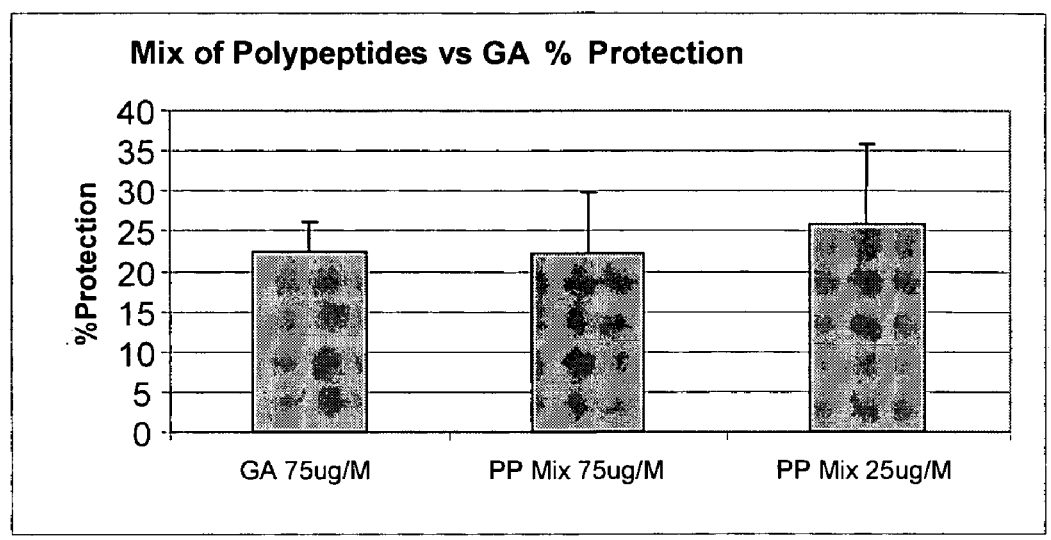
FIG. 2 Effect of a single injection of the mixture of polypeptides of the invention at 25 μg/mouse and at 75 μg/mouse and of GA on survival of RGCs following glutamate-induced toxicity in mice. [The bars represent the mean±SE % protection values in the tested groups calculated vs the mean value of the negative control group. M=mouse.]

The mixture of polypeptides of the invention and GA were dissolved in Phosphate Buffered Saline (PBS) and injected subcutaneously in the flank Results The results displayed in FIG. 2 show that both GA and the mixture of polypeptides of the invention protected RGCs from the toxic effects of an intravitreal glutamate insult in mice. Treatment with GA provided 23% protection, while treatment with the mixture of polypeptides of the invention provided 26% and 22% protection in the low (25 µg/mouse) and high (75 µg/mouse) dose groups, respectively. These effects were statistically significant (p<0.05) relative to the RGC count measured in the negative control group.

EXAMPLE 2B

Effect of Single Injection on the Immune Response to GA and the Mixture of Polypeptides of the Invention An investigation was conducted to assess the immunological response to treatment with GA and the mixture of polypeptides of the invention in mice following a single injection. The study was conducted over a period of 7 days. Male C57BL/6J mice aged 1.5-2 months received a single injection of the mixture of polypeptides of the invention (75 µg/mouse) or GA (75 µg/mouse). During the study period following the injection, subsets of animals in each treatment group were sacrificed on days 1, 3 and 7 post-injection. Spleens were removed and a primary culture of spleen cells was prepared. Cells were activated in vitro with the mixture of polypeptides of the invention or GA and cytokine secretion was measured using commercial ELISA kits. The concentrations of IL-2, IL-10 and IFN-γ determined in the spleen cultures at each time point are plotted in three graphs in FIG. 1. IL-4 was not detected. Taken together, the results show that a single injection of both GA and the mixture of polypeptides of the invention evoked an immunological response, where the peak effect was observed on Day 3 post-injection. The mixture of polypeptides of the invention was found to be more immunogenic than GA.

Results

The presence of an enhanced immunological response following the mixture of polypeptides of the invention administration shows that the mixture of polypeptides of the invention evokes a beneficial T-cell response that, e.g. mediates neuronal protection against loss of RGCs. Moreover, the T-cell response elicited by the mixture of polypeptides of the invention is superior to the T-cell response elicited by GA.

EXAMPLE 2C

Weekly Injections

Polypeptide mixture of the invention immunization was proved to attenuate neuronal cell death induced by exposure to elevated levels of the excitotoxic neurotransmitter glutamate. The neuroprotective effect is dependent upon activation and proliferation of the polypeptide mixture of the invention specific T-cells. Using the model of induced cytotoxicity in mouse optic nerve, the inventors have conducted studies to test the potential neuroprotective properties of the polypeptide mixture of the invention.

The mice were immunized by SC injections of 75 µg/mouse the polypeptide mixture of the invention, or 75 µg/mouse GA, or phosphate buffer saline (PBS) control, administered once a week, nine consecutive injections from Day −63 to Day −7 prior to the induction of glutamate toxicity.

Figure 15:
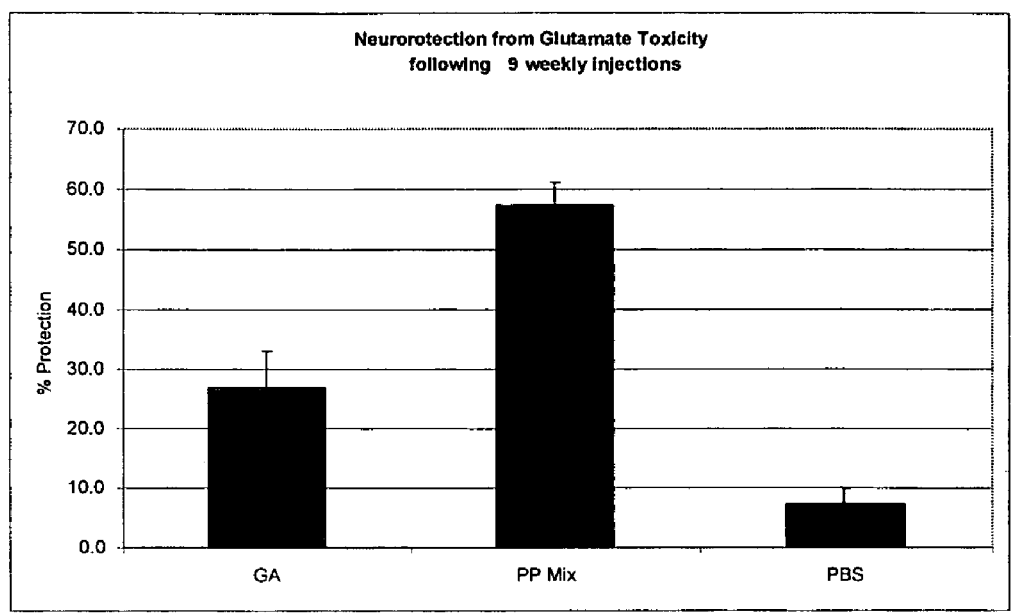
FIG. 15 Neuroprotection from glutamate toxicity following nine weekly injections of the mixture of polypeptides of the invention, GA, or PBS control.

FIG. 15 shows that 9 repeated injections, administered once a week, of 75 µg/mouse of either GA RS or the polypeptide mixture of the invention TS, provide a significant neuroprotective effect on retinal ganglion cells (RGC) survival in the glutamate toxicity model.

Repeated weekly injections of 75 µg of the polypeptide mixture of the invention showed a high and significant neuroprotective effect (p<0.01). Similarly, weekly administration of GA at the same dose level resulted in a good neuroprotective effect (p=0.05), though it was smaller as compared to the effect of the polypeptide mixture of the invention. There was a very small placebo effect.

These data demonstrate that on top of the polypeptide mixture of the invention being effective when administered once weekly, in this administration schedule the polypeptide mixture of the invention is more effective than GA, therefore supporting a weekly administration schedule for the polypeptide mixture of the invention.

EXAMPLE 3

In Vivo Immunological Studies

Effect of Single Injection on the Immune Response to GA and the Mixture of Polypeptides of the Invention An investigation was conducted to assess the immunological response to treatment with GA and the mixture of polypeptides of the invention in mice following a single injection. The study was conducted over a period of 7 days. Male C57BL/6J mice aged 1.5-2 months received a single injection of the mixture of polypeptides of the invention (75 μg/mouse) or GA (75 μg/mouse). During the study period following the injection, subsets of animals in each treatment group were sacrificed on days 1, 3 and 7 post-injection. Spleens were removed and a primary culture of spleen cells was prepared. Cells were activated in vitro with the mixture of polypeptides of the invention or GA and cytokine secretion was measured using commercial ELISA kits. The concentrations of IL-2, IL-10 and IFN-γ determined in the spleen cultures at each time point are plotted in three graphs in FIG. 1. IL-4 was not detected.

Taken together, the results showed that a single injection of both GA and the mixture of polypeptides of the invention evoked an immunological response, where the peak effect was observed on Day 3 post-injection. In most cases, the mixture of polypeptides of the invention was found to be more immunogenic than GA.

Immunological Response to Weekly vs. Daily Injections in Mice (3 Week Study)

Figure 14:
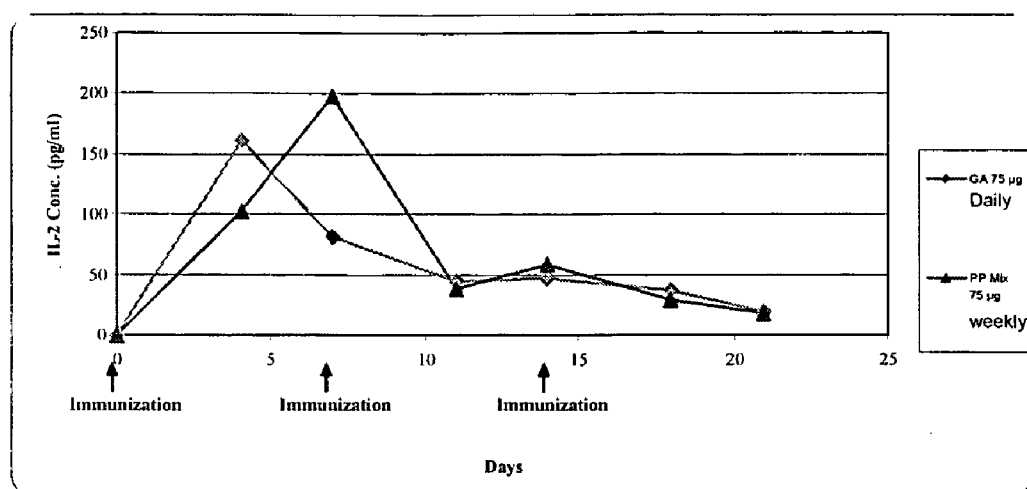
FIG. 14 IL-2 secretion from mouse splenocytes following three weekly injections of the mixture of polypeptides of the invention or daily injections of GA.

Based on the fact that the mixture of polypeptides of the invention was found to be more immunogenic than GA in-vivo, the effect of the mixture of polypeptides of the invention in administration schedule less frequent than that for GA was evaluated. An investigation was conducted to assess the immunological profile of a weekly administration of the mixture of polypeptides of the invention in mice vs. a daily administration of GA. The study was conducted over a period of 21 days (Day 0-Day 21). Mice were injected once a week (total of 3 injections) with the mixture of polypeptides of the invention (75 μg/mouse) or daily with GA (75 μg/mouse). During the study period which followed each of the injections, subsets of animals in each treatment group were sacrificed on days 4 and 7 of each week, spleens were excised and primary cell cultures were prepared. The effect of the treatment was tested by in vitro activation of splenocytes, and specific T-cell response was monitored by detection of cytokines secreted from activated cells. The results of IL-2 measurements are shown in FIG. 14.

Daily injections of GA or once-weekly injections of the mixture of polypeptides of the invention provided a similar immune response of GA-specific T cells, as evident by IL-2 secretion. Once-weekly injections of the mixture of polypeptides of the invention induced a strong IL-2 secretion after the first injection. This secretion decreased ("tolerance") with repeated injections, in parallel with 7-10 daily injections of GA. No significant difference was observed between GA and the mixture of polypeptides of the invention administered once daily or once-weekly, respectively. The levels of additional cytokines, i.e. IFN-γ, IL-10 and IL-4, were examined throughout the tested three weeks. All cytokines determined in the spleen cultures showed similar pattern of initial peak, and a subsequent decline to steady low levels. An additional experiment testing the effect of nine consecutive weekly injections of the polypeptide mixture of the invention showed similar immunological response: a decrease in secretion of all cytokines after the third injection.

EXAMPLE 4

Neuroprotective Effect of the Mixture of Polypeptides of the Invention

Neuroprotective Response in Glutamate Toxicity Model to Weekly Injections in Mice (9 Week Study)

Having shown the immunological response to weekly administration of the mixture of polypeptides of the invention, the effect of weekly repeated injections of the mixture of polypeptides of the invention on protection of RGCs from glutamate toxicity was tested. The mice were immunized by a sc injection of 75 μg/mouse of the mixture of polypeptides of the invention, or 75 μg/mouse GA, or PBS control administered once a week, nine consecutive injections from day −63 to day −7 prior to the induction of glutamate toxicity. FIG. 15 shows that 9 repeated injections, administered once a week, of 75 μg/mouse of either GA RS or the reference standard of the mixture of polypeptides of the invention, provide a significant neuroprotective effect on RGC survival in the glutamate toxicity model. Repeated weekly injections of 75 μg of the mixture of polypeptides of the invention (~16,000 Daltons) showed a high and significant neuroprotective effect ($p<0.01$). Similarly, weekly administration of GA at the same dose level resulted in a good neuroprotective effect ($p=0.05$), though it was smaller as compared to the effect of the mixture of polypeptides of the invention. There was a very small placebo effect.

These data demonstrate that not only is the mixture of polypeptides of the invention effective when administered once weekly, in this administration schedule the mixture of polypeptides of the invention was more effective than GA, therefore supporting a weekly administration schedule for the mixture of polypeptides of the invention.

Discussion of Results

GA fractionation studies showed that peptides characterized by increased molecular size and hydrophobicity exhibit progressively higher effect in both in vivo and ex vivo tests, i.e. the higher the average molecular weight, the higher is the biological activity and immunogenicity. These studies established the basic rationale for the development of the mixture of polypeptides of the invention as an improved product for MS.

Indeed, the mixture of polypeptides of the invention showed increased relative potency ex vivo, antibodies specific to GA recognize the mixture of polypeptides of the invention and the interaction of the antibodies with the mixture of polypeptides of the invention yields a stronger signal in ELISA compared to that of GA, in correlation with an increase in MW of its peptides: the higher the average molecular weight the higher the immunogenicity and potency.

These results were in agreement with the effect of an increase in average molecular weight on activity in vivo in both acute and chronic EAE models. All batches of the mixture of polypeptides of the invention exhibited higher activity in the EAE blocking test, as compared to GA. At a dose as low as 100 μg/mouse, batches of the mixture of polypeptides of the invention reduced the incidence of sick mice (increased % activity) and reduced the severity of the disease to a level similar to that conferred by GA RS at 250 µg/mouse.

The mixture of polypeptides of the invention showed increased immunogenicity in vivo. A single injection of both GA and the mixture of polypeptides of the invention evoked immunological response, where the mixture of polypeptides of the invention was found to be more immunogenic than GA. The presence of an enhanced immunological response following administration of the mixture of polypeptides of the invention lent support to the hypothesis that the mixture of polypeptides of the invention evokes a beneficial T-cell response that mediates neuronal protection.

In agreement with enhanced immunogenicity in vivo of the mixture of polypeptides of the invention, in immunological studies in mice no significant difference was observed between GA and the mixture of polypeptides of the invention administered once daily or once-weekly, respectively. Daily injections of GA or once-weekly injections of the mixture of polypeptides of the invention provided a similar immune response of GA-specific T cells.

The studies of the neuroprotective effect of the mixture of polypeptides of the invention showed that active immunization with the mixture of polypeptides of the invention provides effective neuroprotection from glutamate toxicity, suggesting that the mixture of polypeptides of the invention is a neuroprotective agent that would have clinical benefits in the treatment of neurodegenerative disorders in which glutamate is a prominent participant such as MS, ALS, Huntington's Disease and glaucoma.

Taken together, these findings suggested that the mixture of polypeptides of the invention was efficacious when administered once weekly, was more efficacious than GA, and therefore can potentially confer a therapeutic effect in MS when administered at a lower frequency than GA, supporting weekly administration schedule for the mixture of polypeptides of the invention, and weekly, monthly or bimonthly administration in other neurological disorders.

EXAMPLE 5

Monthly Injections of the Mixture of Polypeptides of the Invention

In order to investigate whether a monthly treatment regimen (immunization) with the mixture of polypeptides of the invention would protect RGCs from glutamate-induced toxicity, mice were assigned to the following pre-insult treatment groups:

1) 25 µg/mouse the mixture of polypeptides of the invention administered once a month (3 times) before the glutamate insult, on Days −63, −35 and −7. (n=29)
2) 75 µg/mouse of the mixture of polypeptides of the invention administered once a month (3 times) before the glutamate insult, on Days −63, −35 and −7. (n=38)
3) No pretreatment administered ("negative control"). (n=38)

The mixture of polypeptides of the invention was dissolved in PBS and injected subcutaneously in the flank.

Results

Figure 3:
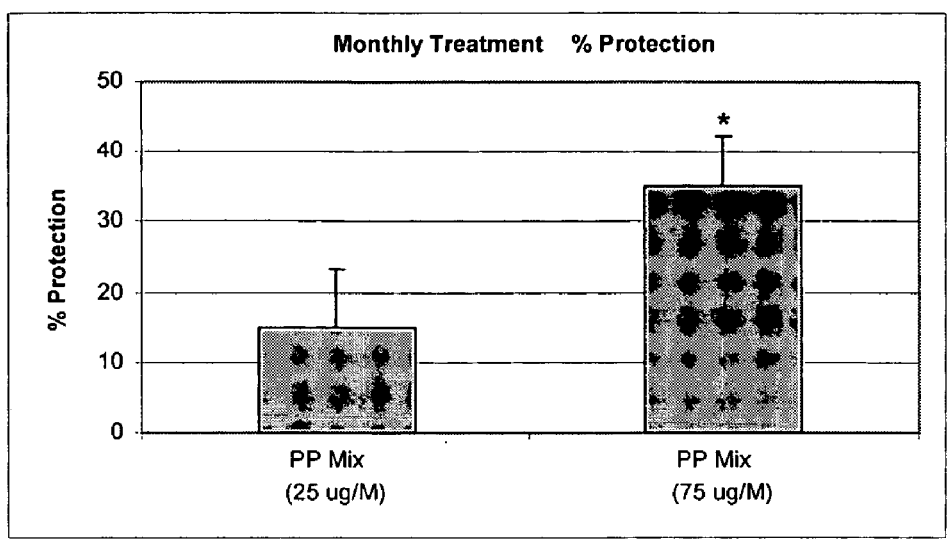
FIG. 3 Effect of three monthly injections of the mixture of polypeptides of the invention on survival of RGCs following glutamate-induced toxicity in mice (three successive injections at 75 μg/mouse). [The bars represent the mean±SE % protection values in the tested groups calculated vs. the mean value of the negative control group. M=mouse.]

The results of the study are displayed in FIG. 3 which shows the protective effects of the mixture of polypeptides of the invention on RGC survival in the immunized treatment groups. The results displayed in FIG. 3 show that treatment with the mixture of polypeptides of the invention protected RGCs. The observed effect was higher in the group treated with monthly repeated administrations of the mixture of polypeptides of the invention at a dose of 75 µg/mouse (35% protection) (p<0.01). The results of the above study show that immunization with the mixture of polypeptides of the invention provides effective neuroprotection from glutamate toxicity, suggesting that the mixture of polypeptides of the invention may have clinical benefits in the treatment of degenerative disorders in which glutamate is a prominent participant, e.g. glaucoma, multiple sclerosis and other neurodegenerative diseases. Farkas R H, Grosskreutz C L, Apoptosis, neuroprotection and retinal ganglion cell death: an overview, Int Ophthalmol Clin 2001, 41:111-130; Sucher N J, Lipton S A, Dreyer E B, Molecular basis of glutamate toxicity in retinal ganglion cells, Vision Res 1997, 37:3483-3493; Osborne N N, Ugarte M, Chao M, Childlow G, Bae J H, Wood J P M, Nash M S, Neuroprotection in relation to retinal ischemia and relevance to glaucoma, Survey of Ophthalmology 1999, 43(Supp 1):S102-S128; and Dreyer E B, Zurakowski D, Schumer R A, Podos S M, Lipton S A, Elevated glutamate levels in the vitreous of humans and monkeys with glaucoma, Arch Ophthalmol 1996; 114:299-305.

EXAMPLE 6

Effect of Monthly Injections on the Immune Response to the Mixture of Polypeptides of the Invention An investigation was conducted to assess the immunological profile of the mixture of polypeptides of the invention in mice during the monthly treatment regimen used in the above study. The experiment duplicated the monthly administration schedule that was used to test the neuroprotective properties of the mixture of polypeptides of the invention following an intravitreal glutamate insult.

The study was conducted over a period of 70 days (Day 0-Day 70). Using the same monthly treatment regimen described above, mice were injected once a month (total of 3 injections) with the mixture of polypeptides of the invention (75 µg/mouse) on three occasions—Days 0, 28 and 56. During the study period which followed each of these injections, subsets of animals in each treatment group were sacrificed on days 3, 7, 14 & 28 post-injection. For the third treatment, the procedure was only conducted 3, 7 & 14 days post-injection. Cytokine secretion from primary spleen cultures was determined as described above.

Figure 4:
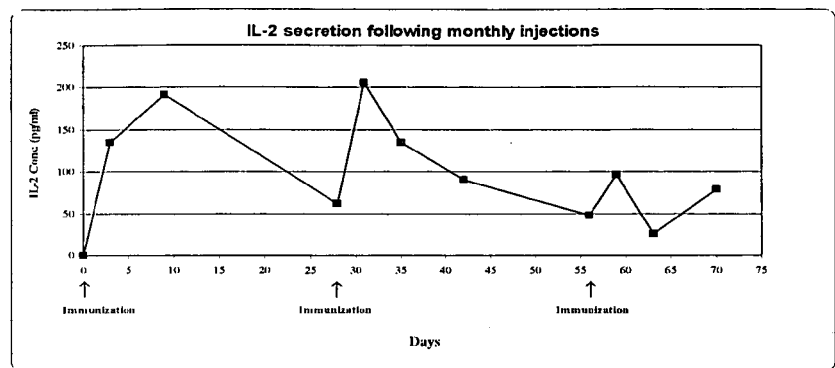
FIG. 4 Cytokine secretion (IL-2, IFN-γ, IL-10, IL-4) from mouse splenocytes following three successive monthly injections of the mixture of polypeptides of the invention (75 µg/mouse).
Figure 4:
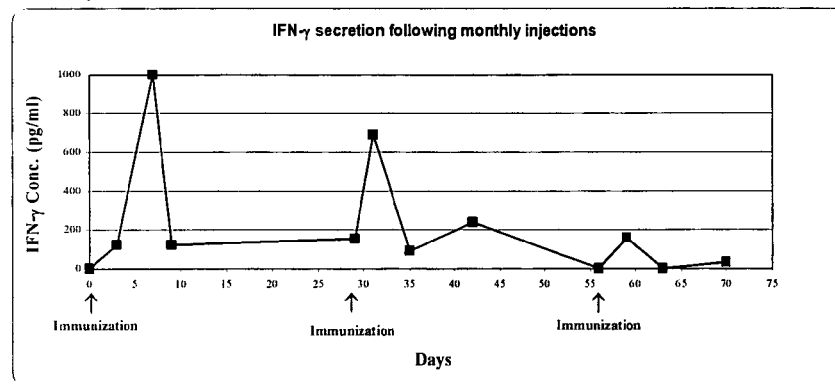
Figure 4:
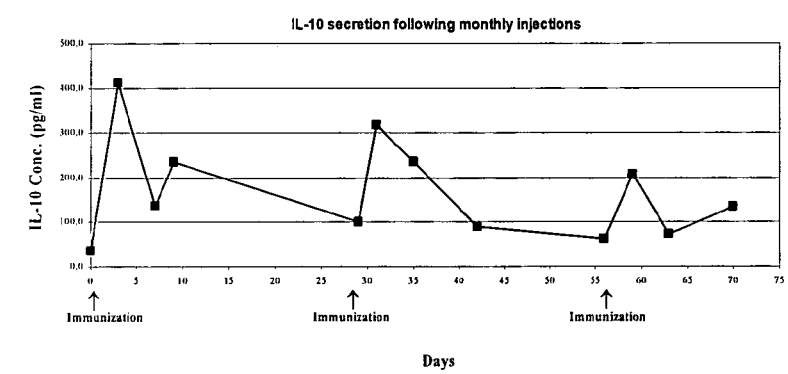
Figure 4:
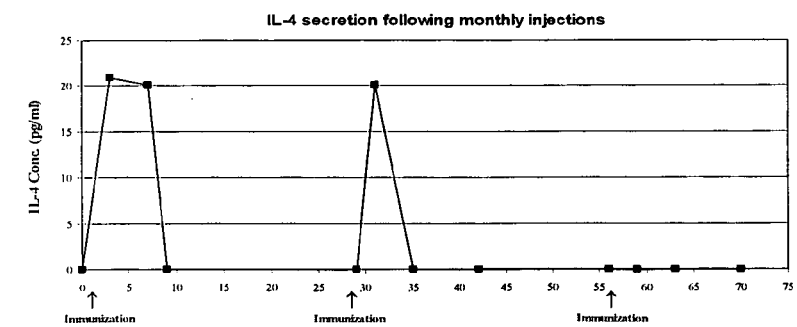

The concentrations of IL-2, IFN-γ, IL-10 and IL-4 determined in the spleen cultures at each time point are plotted in FIG. 4. Taken together, the graphs show that each of the three administrations of the mixture of polypeptides of the invention evoked an immunological response.

EXAMPLE 7

Six Month Study

Mice were treated monthly with 75 µg/mouse of the mixture of polypeptides of the invention or GA, or bi-monthly with the mixture of polypeptides of the invention. Splenocytes were cultured and cytokine levels measured at several timepoints.

Results

Figure 5:
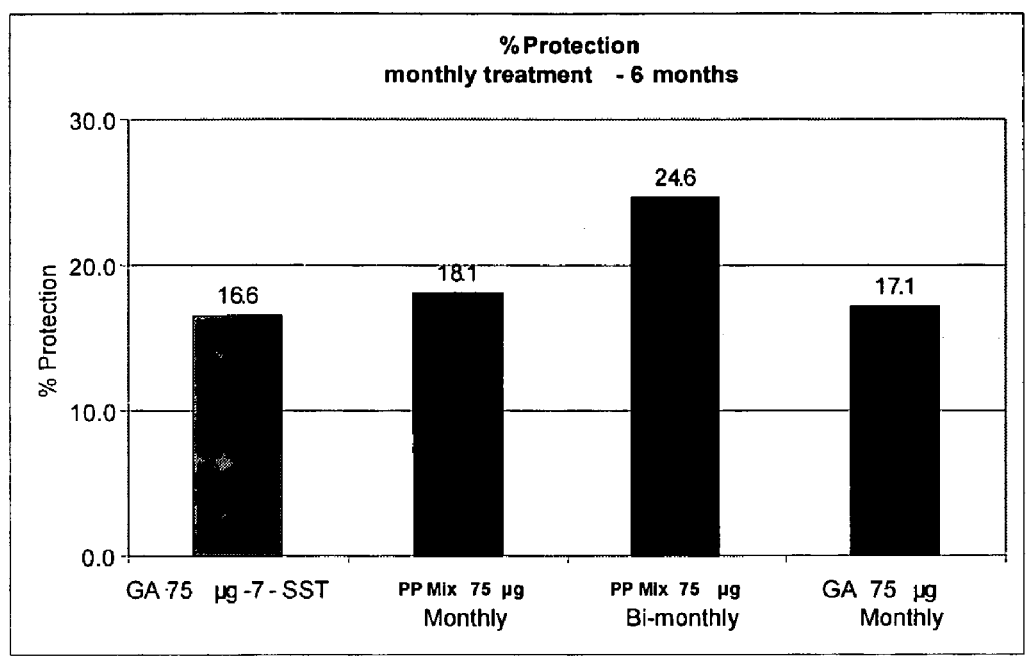
FIG. 5 Protection against glutamate toxicity results from 6 month GA/Mixture of Polypeptides of the Invention study.

Glutamate Toxicity results are shown in FIG. 5. The protection of the positive control group (GA at day −7) is relatively low (the expected result rendering an experiment valid for batch release is above 20-25%), which may be attributed to the "old" age of the mice. All the data collected in this model up-to-date is in 8-12 week old mice. However, relative to the positive control group of the experiment, all the treatment groups showed similar or higher % protection. Furthermore, the effect of bi-monthly administration of the mixture of polypeptides of the invention showed close to statistical significance (p=0.058).

It is important to note that both monthly (total of 6 injections) and bi-monthly (total of 3 injections) schedules of administration provide equal or greater protection than single injection at day −7, i.e. repeated injections in these frequencies are neuroprotective.

Figure 6:
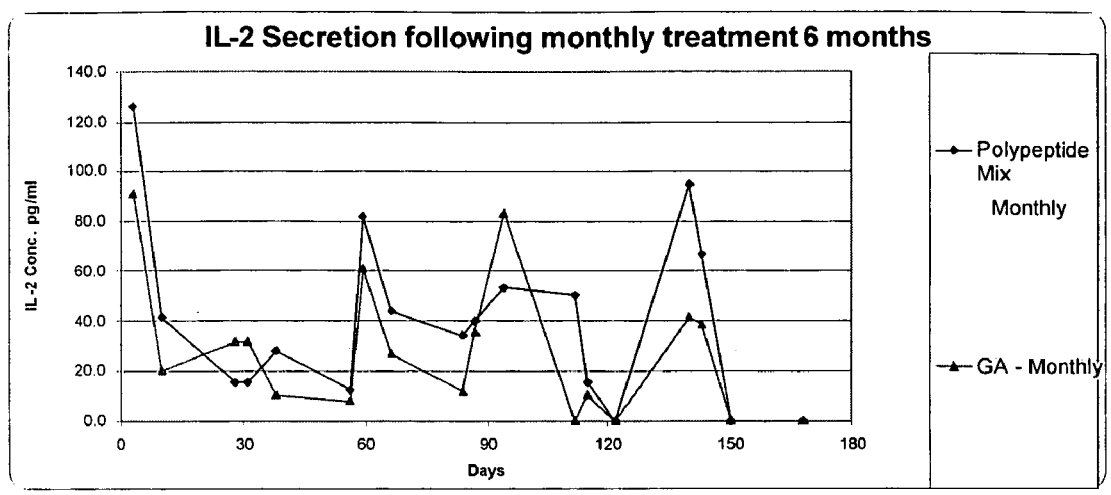
FIG. 6 IL-2 secretions following monthly treatment of the mixture of polypeptides of the invention and GA for 6 months.
Figure 7:
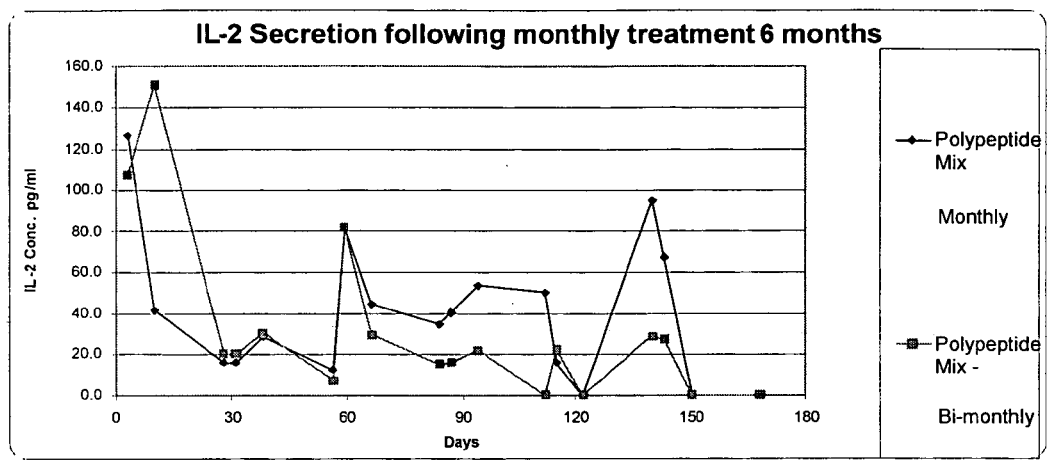
FIG. 7 IL-2 secretions following monthly and bi-monthly treatments of the mixture of polypeptides of the invention for 6 months.
Figure 18:
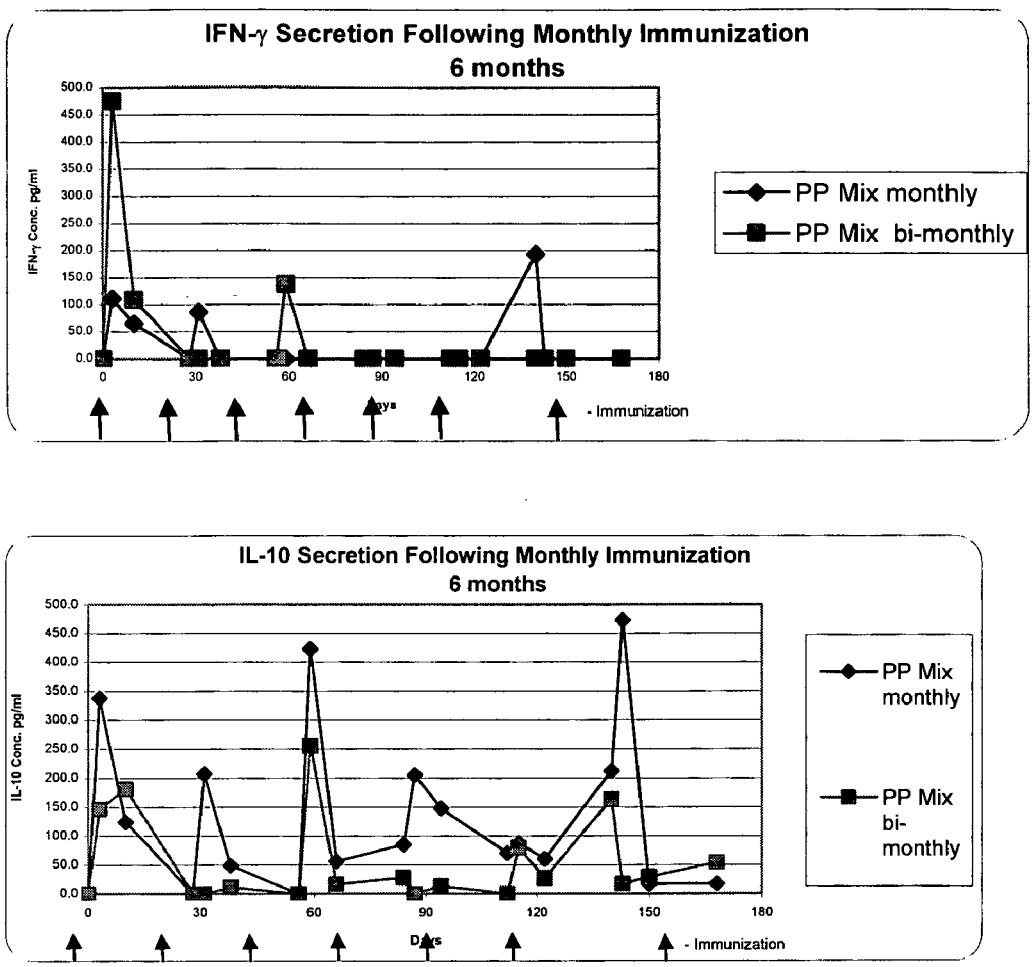
FIG. 18 IFN-γ secretions and IL-10 secretions following a monthly or bi-monthly immunization for 6 months.

Immunology results are shown in FIGS. 6, 7, and 18. IL-2 levels were measured following each injection. The results in FIG. 6 show a rapid rise and decline in the first cycle, as seen in previous experiments, followed by lower peaks in each of the five successive cycles. The current results confirm ability of the mixture of polypeptides of the invention to elicit a stronger T-cell response than GA. The results also confirm the ability of monthly treatment to boost the immune response, albeit at a level about half of the initial response. This response seems to be sufficient to maintain a neuroprotective effect. Bi-monthly injections of the mixture of polypeptides of the invention show the ability to boost the immune response following each injection, though at progressively lower levels (FIG. 7). FIG. 18 shows the TH1-TH-2 shift after several injections, showing a decrease in IFN-γ response and a stable if not rising IL-10 response.

The results also show that the immune response is maintained after each new injection, as indicated by the presence of a peak after each boost.

EXAMPLE 8

Ocular Hypertension in Rats

The effect of the mixture of polypeptides of the invention on RGC survival was tested in a rat model of chronically elevated IOP, a major risk factor in glaucoma.

Materials and Methods

A unilateral increase in IOP was induced in anesthetized male Lewis rats (aged 8 weeks) by laser photocoagulation of the limbal and episcleral veins. Rats received two laser cauterization treatments, one week apart. IOP was measured one week following the second laser treatment. The second laser treatment was followed two weeks later by application of a fluorescent retrograde neurotracer distally to the optic nerve head. One day after dye application (3 weeks after the initial laser treatment) the rats were sacrificed, their retinas excised, fixed in paraformaldehyde and whole mounted on filters. Survival of RGCs was determined by counting the labeled cells using a fluorescent microscope (similar to the procedure described above).

To examine the effect of immunization with the mixture of polypeptides of the invention on the survival of RGCs, rats received a single subcutaneous injection of the mixture of polypeptides of the invention (0, 100, 250, 500, or 1000 μg/rat) prior to the second laser treatment. The number of animals tested in the 100, 250, 500, 1000 μg/rat groups and in the vehicle control (PBS-injected) group was n=11, n=13, n=12, n=7 and n=16, respectively. (See FIG. 8) A further group of naïve animals received no laser treatments (n=3). The "% Protection" of treatment with the mixture of polypeptides of the invention in relation to control (PBS) treatment, and the statistical significance of the effect, were calculated in the manner described Example 2.

Results

By one week after the last laser cauterization, IOP in treated rats had increased to an average of about 39 mm Hg (compared to an IOP of about 17 mm Hg in normal Lewis rats) and it remained at approximately that level thereafter. Furthermore, the number of surviving RGCs in the PBS-treated rats was reduced by about 50% in relation to RGC count obtained from the naïve (non-cauterized) animals. These data indicate that ocular hypertension, induced in these animals by laser cauterization, resulted in a significant loss of RGCs, as predicted by the model.

Figure 8:
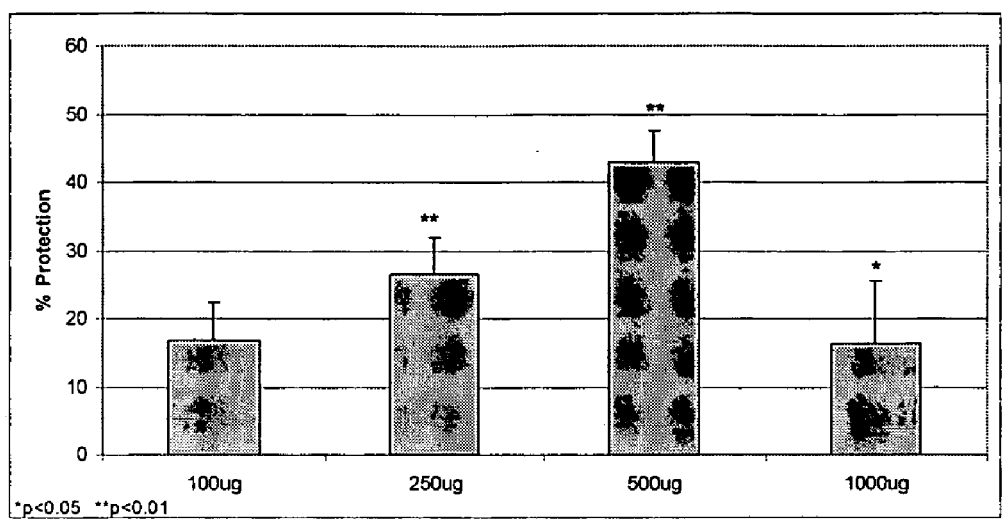
FIG. 8 Effect of treatment with the polypeptide mixture of the invention on survival of RGCs following elevated IOP induced by laser cauterization in rats. [The bars represent the mean±SE % protection values in the tested groups calculated vs. the mean value of the vehicle control group.]

FIG. 8 illustrates the protective effect ("% Protection") of the mixture of polypeptides of the invention on RGC survival in the three immunized treatment groups. The beneficial effect of the mixture of polypeptides of the invention on RGC survival under conditions of elevated IOP appeared to be dose-dependent, with increasing doses of the mixture of polypeptides of the invention providing up to about 43% protection. The most efficacious dose is 500 μg/rat.

Repeated Injections—Treatment Protocol.

Based on the dose response study previously described the dose of 500 μg/rat of the polypeptide mixture of the invention was chosen for testing repeated injections treatment regimen. To examine the effect of the polypeptide mixture of the invention weekly and monthly treatment on the survival of RGCs, rats received repeated subcutaneous injection of 500 μg/rat of the polypeptide mixture of the invention for 12 weeks (weekly treatment—11 injections, monthly treatment—3 injections), starting on the day of the second laser treatment. A control group received weekly PBS, additional positive control (PC) group received a single injection of 500 μg/rat of the polypeptide mixture of the invention on the day of the second laser treatment (Day +7). The number of animals tested in all groups was n=11.

Figure 19:
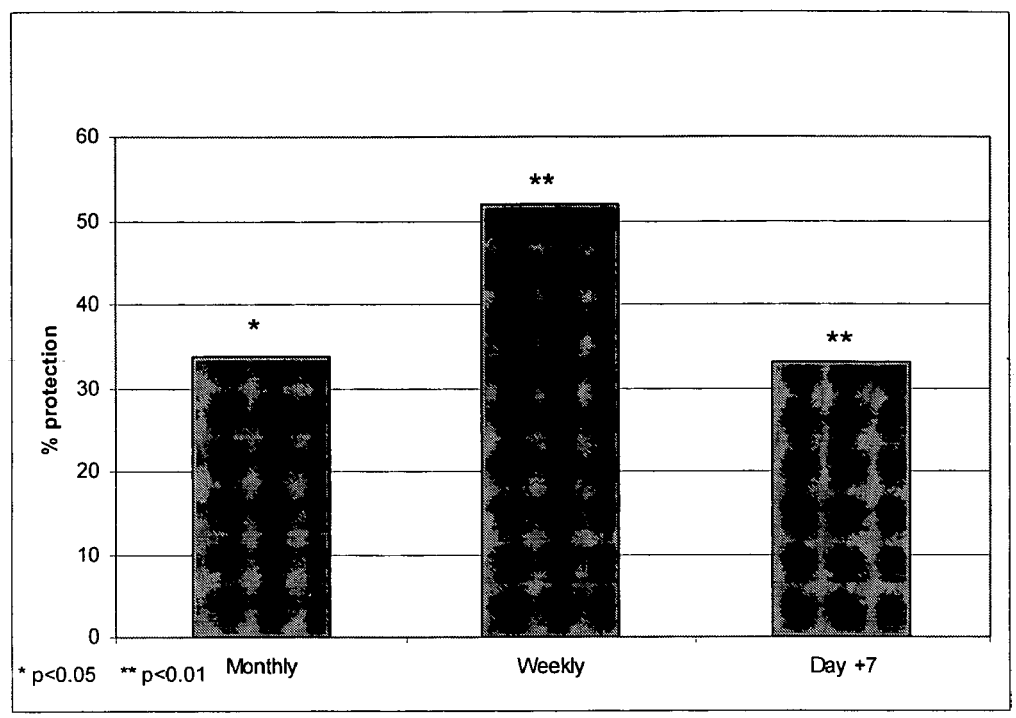
FIG. 19 Protective effect of the mixture of polypeptides of the invention on RGC survival (% of protection after treatment initiated on the day of second laser treatment).

FIG. 19 illustrates the protective effect ("% Protection") of the polypeptide mixture of the invention on RGC survival in the treatment groups. Both monthly and weekly treatment were significantly beneficial as compared to untreated control, p=0.029 and p=0.002 respectively. The effect of weekly treatment is higher than that of the monthly treatment but not statistically significant.

Repeated Injections—Prevention Protocol.

To examine the effect of the polypeptide mixture of the invention weekly and monthly treatment on the survival of RGCs, rats received repeated subcutaneous injection of 500 μg/rat of polypeptide mixture of the invention for 12 weeks (weekly treatment—11 injections, monthly treatment—3 injections), starting 63 days prior to the second laser treatment, last injection for all groups on the day of the second laser treatment. A control group received weekly PBS, additional positive control (PC) group received a single injection of 500 μg/rat of polypeptide mixture of the invention on the day of the second laser treatment (Day +7). The number of animals tested in weekly, monthly, PBS and positive control groups was n=10, n=10, n=12 and n=7 respectively.

Figure 20:
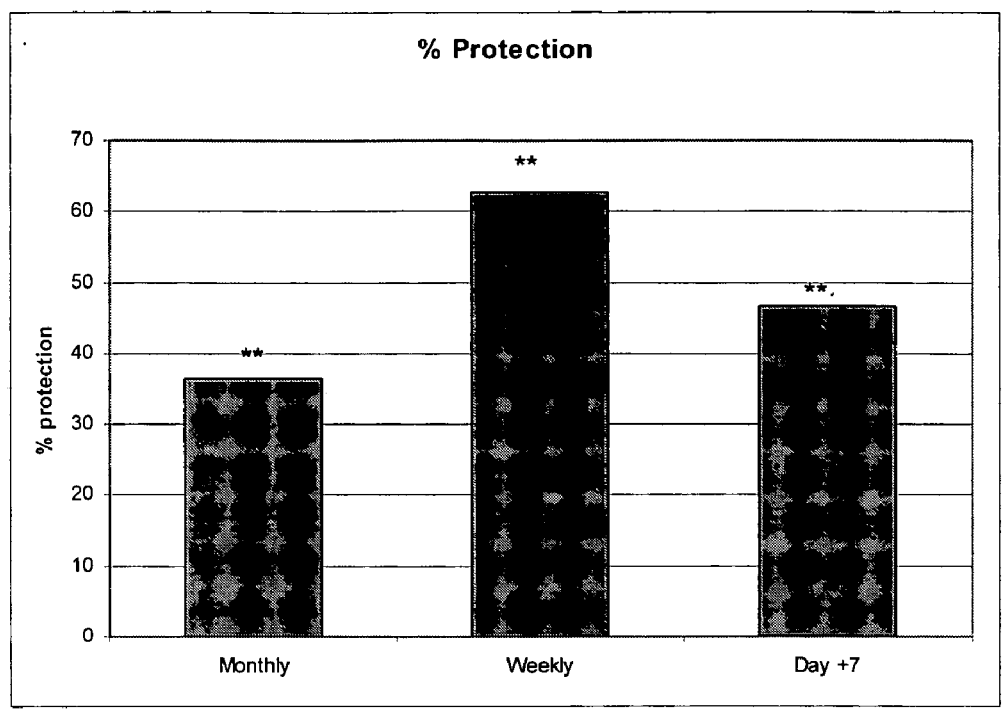
FIG. 20 Protective effect of the mixture of polypeptides of the invention on RGC survival (% of protection after preventive treatment initiated 63 days prior to $2^{nd}$ laser treatment).

FIG. 20 illustrates the protective effect ("% Protection") of polypeptide mixture of the invention on RGC survival in the treatment groups. Both monthly and weekly treatment were significantly beneficial as compared to untreated control, p<0.001. The effect of weekly treatment is significantly higher than that of the monthly treatment (p<0.001), while both regimens are very effective.

EXAMPLE 9

The Mixture of Polypeptides of the Invention in Trinitrobenzene Sulfonic Acid (TNBS) Induced Colitis Model The inflammatory bowel diseases are Crohn's Disease and ulcerative colitis. Both are characterized by chronic inflammation of various sites in the gastrointestinal (GI) tract. Crohn's disease is a nonspecific chronic transmural inflammatory disease that most commonly affects the distal ileum and colon but may occur in any part of the GI tract (Merck Manual of Diagnosis and Therapy (1999), Merck Research Laboratories, (Whitehouse Station, N.J.), 302-312). Ulcerative colitis is a chronic inflammatory and ulcerative disease arising in the colonic mucosa (Merck Manual of Diagnosis and Therapy (1999), Merck Research Laboratories, (Whitehouse Station, N.J.), 302-312).

Figure 16:
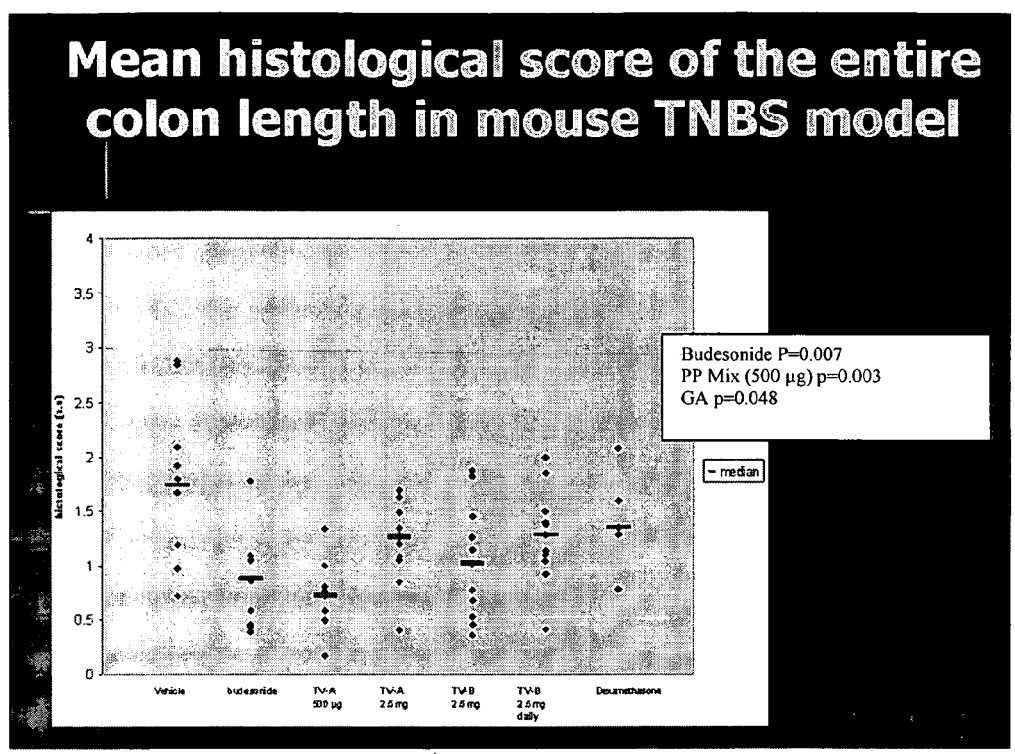
FIG. 16 Activity of the mixture of polypeptides of the invention in the TNBS model in mice versus glatiramer acetate, Budenoside and untreated control.

CSJL mice were treated with either two administrations of the mixture of polypeptides of the invention at days −10 and −4 or two administrations of GA (days −10 and −4) or daily administrations of GA. Budenoside was administered intrarectally at days −1, 0 and 1. Disease was induced by TNBS skin sensitization at day −7 and TNBS rectal sensitization at day 0. Animals were sacrificed at day 2. Read out paramerters were weight loss, diarrhea, colonic shortening, and histological analysis. Results are displayed in FIG. 16.

On day −7 a solution of 3.75 mg TNBS in 150 μl 48% ethanol was applied onto the shaved skin of CSJL mice. On day 0, the animals were anesthetized with isoflurane, after which 1.0 mg TNBS in 100 μl 40% ethanol was administered rectally.

Mice were sacrificed on day 2, colons were dissected from the animals and after removal of the feces the weight and length of the colons was determined.

Figure 17:
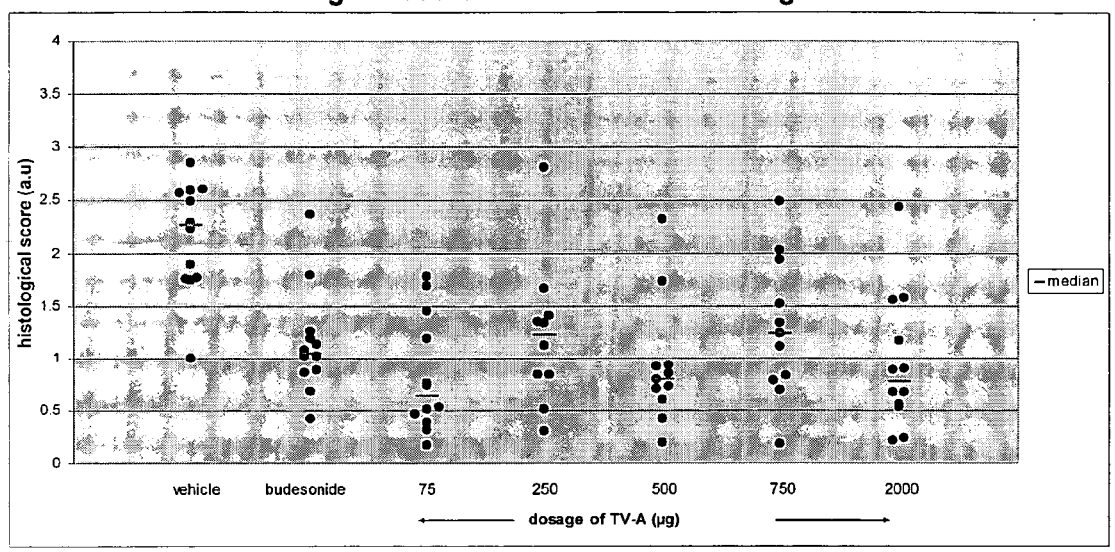
FIG. 17 Mean histological score of the entire colon length in mice treated with the vehicle, budesonide and the polypeptide mixture of the invention in 75, 250, 500, 750, or 2000 µg dosage. The score of each colon tissue magnification field ranged from 0 to 4 (the higher the score, the more severe the disease).

The colon was fixed in 4% buffered formalin and embedded in paraffin. Tissue sections (5 μm) of the formalin fixed colon tissue were stained with hematoxylin/eosin/saffron and evaluated with regard to the extent of inflammation and tissue damage. Histological grading was done in a blinded fashion. The score of each magnification field ranged from 0 to 4 (the higher the score, the more severe the disease) (See FIG. 17).

Mice rectally treated with budesonide developed significantly less severe colitis than vehicle-treated mice evident from significantly less weight loss, a lower clinical score, less redness of the colon and a lower histological score.

This study showed that the mixture of polypeptides of the invention inhibits the development of TNBS induced colitis. The mixture of polypeptides of the invention had a significant and beneficial effect on the body weight, the clinical score, redness of the colon and the histological score. (See FIGS. 20 and 21).

Regardless of dosage, the mixture of polypeptides of the invention inhibited the extent and severity of inflammation and tissue damage present both in the rectal half and in the proximal half of the colon.

The mixture of polypeptides of the invention was most effective at a dosage of 75 μg, 500 μg and 2 mg per mouse.

The dose response for the mixture of polypeptides of the invention was bell shaped which is characteristic of the activity of immunomodulators.

EXAMPLE 10

Activity of the Mixture of Polypeptides of the Invention in the Balb/C Mouse DSS Model Balb/c mice were subjected to experimental colitis induction by providing 3.5% DSS in the drinking $H_2O$, continuously supplied ad libitum for a duration of 7 days, followed subsequently by 3 days of regular drinking $H_2O$ until study termination on study day 10. Disease activity was measured with the following parameters: Mortality; Body Weight; Clinical Score and Colon Length.

| Score | % Weight loss | Clinical Signs (Stool consistency & Rectal bleeding) |
|---|---|---|
| 0 | <0 | Normal/Formed |
| 1 | 0-4.9 | Past/Formed |
| 2 | 5-9.9 | Pasty/Unformed to Soft |
| 3 | 10-20 | Diarrhea or Blood traces in stool |
| 4 | >20 | Gross rectal bleeding |
| 5 | Death | Death |

DSS-induced colitis was evident in the control (PBS) group, as seen by mortality (30%), weight loss, clinical severity and shortening of the colon. Treatment with both GA and the mixture of polypeptides of the invention improved clinical severity. The treatment regimen of 100 mg/kg (2 mg/mouse) the mixture of polypeptides of the invention administered on days 0, 4 and 8, proved to be more effective than daily treatment. There was a dose-dependent improvement in clinical outcome using the mixture of polypeptides administered on 3 occasions (days 0, 4 and 8).

EXAMPLE 11

Clinical Testing

Glaucoma

Glaucoma is a group of ocular diseases characterized by progressive damage to the eye at least partly due to elevated intraocular pressure (IOP)("Glaucoma", Merck Manual of Diagnosis and Therapy (1999), Merck Research Laboratories, (Whitehouse Station, N.J.), 733-738). Additionally, glaucoma is characterized by retinal ganglion cell (RGC) death, axon loss and an excavated appearance of the optic nerve head (Alward, "Medical Management of Glaucoma", N Eng J Med, 1998; 339:1298-1307). Glaucoma can be diagnosed before vision loss occurs by visual field testing and by ophthalmoscopic examination of the optic nerve to detect "cupping." The management of glaucoma is based on lowering the IOP to prevent further optic nerve damage. The mean IOP in normal adults is 15 to 16 mm Hg; the normal range is 10 to 21 mm Hg. The first step in the management of glaucoma is based on lowering the IOP using topically applied medications (Coleman, "Glaucoma", Lancet, 1999; 354: 1803-1810). Currently there are five major classes of medications that are used to lower the IOP: β-adrenergic antagonists, adrenergic agonists, parasympathomimetics, prostaglandin-like analogues and carbonic anhydrase inhibitors (Medeiros, et al., "Medical Backgrounders: Glaucoma", Drugs of Today 2002; 38:563-570). Although most medications are applied topically to the eye, they can cause severe systemic side effects and adversely affect the quality of the patient's life. If additional lowering of IOP is indicated or if medication fails to sufficiently lower the IOP, laser trabeculoplasty is usually the next step. If IOP is still not adequately controlled, incisional glaucoma surgery is indicated (Id). The lowering of IOP, although significantly reducing the extent of neuronal loss, does not ensure cessation of the disease process, because the loss of Retinal Ganglion Cells (RGCs) may continue. Recent studies of the association between IOP regulation and visual field loss after medical or surgical intervention showed that ongoing neuronal loss reflected in visual field tests can be diminished if the IOP is low. However, neuronal loss may continue to occur after reduction of IOP (Bakalash, et al., "Resistance of Retinal Ganglion Cells to an Increase in Intraocular Pressure is Immune-dependent", Invest Ophthalmol Vis Sci 2002; 43:2648-2653).

Glaucomatous optic neuropathy appears to result from specific pathophysiological changes and subsequent death of RGCs and their axons. The process of RGC death is thought to be biphasic: a primary injury responsible for initiation of damage followed by a slower, secondary degeneration attributable to the hostile environment surrounding the degenerating cells (Kipnis, et al., "T Cell Immunity To Copolymer 1 Confers Neuroprotection On The Damaged Optic Nerve: Possible Therapy For Optic Neuropathies", Proc Natl Acad Sci 2000; 97:7446-7451).

RGC death mechanisms in experimental animal models of glaucoma and human glaucoma have been shown to involve apoptosis. Although the molecular mechanism triggering the apoptosis has not been identified, deprivation of neurotrophic factors, ischemia, chronic elevation of glutamate and disorganized nitric oxide metabolism are suspected to be possible mechanisms (Farkas, et al., "Apoptosis, Neuroprotection and Retinal Ganglion Cell Death: An Overview", Int Ophthalmol Clin 2001; 41:111-130). In addition, it would not be surprising if the mechanisms leading to RGC death shared common features with other types of neuronal injury, such as signaling by reactive oxygen species, depolarization of mitochondria, or induction of transcriptionally regulated cell death (Weinreb, et al., "Is Neuroprotection a Viable Therapy for Glaucoma?" Arch Ophthalmol 1999; 117:1540-1544).

It has been hypothesized that an excessive release of the excitatory amino acid glutamate in the retina may contribute to cell death. Glutamate is an important neurotransmitter in the retina, but when released in excess it can be toxic to RGCs. It is therefore essential that glutamate levels be tightly regulated within the retina. Glutamate toxicity seems to be mediated, at least in part, through N-methyl-D-aspartate (NMDA) receptors that can allow entry of excessive amounts of calcium. The increase in intracellular calcium appears to activate the enzyme nitric oxide synthase, which generates reactive oxygen species. These free radicals ultimately destroy the cell. Neuronal ischemia has been proposed as the mechanism underlying the glutamate elevation observed in glaucoma (Sucher, et al., "Molecular Basis of Glutamate Toxicity in Retinal Ganglion Cells", Vision Res 1997; 37:3483-3493; Osborne, et al., "Neuroprotection in Relation to Retinal Ischemia and Relevance to Glaucoma", Survey of Ophthalmology 1999; 43(Supp 1):S102-S128).

In the brain, glutamate abnormalities have been implicated in a number of neurologic diseases, including Alzheimer's disease, Huntington's disease, Parkinson's disease and epilepsy (Sucher, et al., "Molecular Basis of Glutamate Toxicity in Retinal Ganglion Cells", Vision Res 1997; 37:3483-3493). Elevated glutamate concentrations have been found in the vitreous of patients with glaucoma and also in monkeys with experimental glaucoma (Dreyer, et al., "Elevated Glutamate Levels in the Vitreous of Humans and Monkeys with Glaucoma", Arch Ophthalmol 1996; 114:299-305). However, whether abnormalities of glutamate metabolism play a causative role in either primary glaucomatous RGC death or in secondary RGC degeneration remains uncertain.

In recent years there has been increasing interest in preventing progression of glaucomatous optic neuropathy using approaches based on the premise that glaucoma is a neurodegenerative disease (Fisher, et al., "Vaccination for Neuroprotection in the Mouse Optic Nerve: Implications for Optic Neuropathies", J Neurosci 2001; 21:136-142). Neuroprotection of the glaucomatous optic nerve would therefore be an adjunctive therapeutic paradigm for use with conventional IOP-lowering treatments (Schwartz, et al., "Potential Treatment Modalities for Glaucomatous Neuropathy: Neuroprotection and Neurodegeneration", J. Glaucoma 1996; 5:427-432). Research led to the development of the concept of "protective autoimmunity", i.e. a physiological response in which auto-reactive T cells confer protection against neurodegeneration (Schwartz, et al., "Protective Autoimmunity Against the Enemy Within: Fighting Glutamate Toxicity", Trends in Neurosciences, 2003; 26:297-302; Moalem, et al., "Autoimmune T Cells Protect Neurons form Secondary Degeneration after Central Nervous System Axotomy", Nat Med 1999; 5:49-55).

Neuroprotection is a novel therapeutic paradigm for slowing or preventing degeneration and death of neurons to maintain their physiological function. An important advantage of the neuroprotective strategy is that it allows treatment of disease for which the specific etiology is either unknown or differs among patients. This is particularly relevant to the treatment of glaucoma where neuroprotection should be effective independently of whether a particular patient's glaucoma is due to primary or secondary disease mechanisms (Weinreb, et al., "Is Neuroprotection a Viable Therapy for Glaucoma?", Arch Ophthalmol 1999; 117:1540-1544). Though significantly decreasing neuronal loss, the current IOP-lowering medications do not halt the progressive nature of glaucoma, and the loss of RGCs may continue even after the IOP has been reduced. Thus, the greatest unmet medical need in glaucoma is a therapeutic agent capable of protecting ocular tissue from continued degeneration.

Several approaches to neuroprotection in glaucoma have been proposed. A neuroprotective approach has been suggested which relies on delivering neurotrophins to the retina to compensate for the deprivation of target-derived neurotrophins resulting from blockade of retrograde axoplasmic transport (Weinreb, et al., "Is Neuroprotection a Viable Therapy for Glaucoma?", Arch Ophthalmol 1999; 117:1540-1544). Memantine, an N-methyl-D-aspartate (NMDA) antagonist, reduced ganglion cell loss in a rat model of IOP-induced retinal ischemia (Lagreze, et al. "Memantine is Neuroprotective in a Rat Model of Pressure-induced Retinal Ischemia", Invest Ophthalmol Vis Sci 1998; 39:1063-1066) and is presently being tested in clinical trails with glaucoma patients (Vision Newsletter, Fall 2002, ucsfeye.net/visionsfal02p2.shtml). In a rat model of high IOP, vaccination with Cop-1 significantly reduces the pressure-induced death of RGCs (Schwartz, "Neurodegeneration and Neuroprotection in Glaucoma: Development of a Therapeutic Neuroprotective Vaccine: the Friedenwald Lecture", Invest Ophthalmol Vis Sci 2003; 44:1407-1411; Bakalash, et al., "Antigenic Specificity of Immunoprotective Therapeutic Vaccination for Glaucoma. Invest Ophthalmol Vis Sci 2003; 44:3374-3381; Schwartz M., "Neuroprotection as a Treatment for Glaucoma: Pharmacological and Immunological Approaches", Eur J Ophthalmol 2003; 13:S27-31).

Recent investigations showed that neuroprotection of crush-injured rat optic nerves can be obtained by active immunization with GA on the day of injury and by adoptive transfer of GA-reactive T cells (Kipnis, et al., "T Cell Immunity To Copolymer 1 Confers Neuroprotection on the Damaged Optic Nerve: Possible Therapy For Optic Neuropathies", Proc Natl Acad Sci 2000; 97:7446-7451). GA demonstrated neuroprotective properties in a glutamate-induced toxicity model in mice and in a rat model of elevated intraocular pressure (IOP) by protecting the animals from RGC loss inflicted by intravitreal injection of glutamate (Schori et al., "Vaccination for Protection of Retinal Ganglion Cells Against Death From Glutamate Cytotoxicity and Ocular Hypertension: Implications for. Glaucoma", Proc Natl Acad Sci 2001; 98:3398-3403). Furthermore, in the rat ocular hypertension model, which simulates glaucoma, immunization with GA significantly reduced the RGC loss from 27.8% to 4.3%, without affecting the IOP (Id). Vaccination with GA resulted in significant neuroprotection in rat models of optic nerve crush and chronic glaucoma (Schwartz, "Vaccination for Glaucoma: Dream or Reality?", Brain Res Bull. 2004; 62(6):481-4).

GA-specific activated T cells are used to promote nerve regeneration or to prevent or inhibit the secondary degenerative effects which may follow primary nervous system injury or the effects of neurodegenerative processes caused by a disease or condition including glaucoma (U.S. Patent Application Publication 2002-0037848 A1, published Mar. 28, 2002 (Eisenbach-Schwartz et al.); U.S. Patent Application Publication 2003-0004099 A1, published Jan. 2, 2003 (Eisenbach-Schwartz et al.)).

Multiple Sclerosis

Multiple Sclerosis (MS) is a debilitating autoimmune disease characterized by destruction of myelin (demyelination) in the central nervous system. Relapsing-remitting multiple sclerosis (RR MS) is the most common form of the disease at time of initial diagnosis (Noseworthy, et al., "Multiple Sclerosis", N Engl J Med 2000; 343:938-952). Although RR MS patients typically have mild manifestations between relapses initially, nearly 60% experience a secondary progressive course 15 years after diagnosis. This proportion increases to 90% at 25 years after disease onset, which leaves the majority of patients disabled at a relatively young age (Bjartmar, et al., "Pathological Mechanisms and Disease Progression of Multiple Sclerosis: Therapeutic Implications", Drugs of Today 2002; 38:17-29).

The prevalence of MS varies considerably around the world. (National Multiple Sclerosis Society, available at nationalmssociety.org) The prevalence is highest in northern Europe, southern Australia and the middle part of North America. Worldwide, MS may affect 2.5 million individuals. The reasons for the variation in the prevalence and incidence of MS worldwide are not understood. Environmental and genetic explanations have been offered, and both factors probably have a role. Typically, patients are diagnosed between the ages of 20 and 50. MS is found in two to three times as many women as men. The basis for this difference is unknown (National Multiple Sclerosis Society, nationalmssociety.org).

The management of MS has been substantially advanced by the availability of four injectable disease-modifying agents: interferon beta-1b (Betaseron®), interferon beta-1a intramuscular (Avonex®) and interferon beta-1a subcutaneous (Rebif®) and glatiramer acetate (Copaxone®). After several years of experience with these immunomodulatory drugs, it is the consensus that these agents reduce future disability and improve the quality of life for many individuals with R-R MS. It is thus recommended that immunomodulatory therapy should begin shortly after R-R MS diagnosis and continue for many years. (Freedman M S, Blumhardt L D, Brochet B, Comi G, Noseworthy J H, Sandberg-Wollheim M, Soelberg Sørensen P and the Paris Workshop Group. International consensus statement on the use of disease-modifying agents in multiple sclerosis. Multiple Sclerosis 2002; 8:19-23.)

The choice of the specific agent remains highly dependent on the physician's opinion of its relative potency and the patient's anticipated tolerance to treatment-related side effects. Copaxone® is generally well tolerated and may be most effective for mildly disabled patients with a recent diagnosis of MS who wish to start treatment early in the course of the illness (Noseworthy, et al., "Multiple Sclerosis", N Engl J Med 2000; 343:938-952).

Recent experimental evidence implicates glutamate, the major neurotransmitter in the mammalian brain, as an important contributing factor in MS pathogenesis. Glutamate levels had been found to be elevated in the cerebrospinal fluid of MS patients, and its concentration is associated with the severity and course of the disease. This excitotoxicity, secondary to autoimmunity, could indeed underlie a substantial part of the lesions observed in MS (Matute, et al., "The Link Between Excitotoxic oligodendroglial Death and Demyelinating Diseases", Trends Neurosci. 2001; 24:224-30; Gilgun-Sherki, et al., "Riluzole Suppresses Experimental Autoimmune Encephalomyelitis: Implications for the Treatment of Multiple Sclerosis", Brain Res. 2003; 989:196-204).

Based on the foregoing, two clinical trials are being undertaken.

Glaucoma Clinical Trial

A multi-center, randomized double-blind, placebo-controlled, multiple-dose, three-arm study to assess the tolerability, safety and the efficacy of subcutaneous injections of the mixture of polypeptides of the invention in patients with glaucomatous optic neuropathy at high risk to progress. The study is designed to evaluate the tolerability, safety and the efficacy of multiple subcutaneous injections of the investigational medicinal product in this patient population. The secondary objective of the study is to evaluate the immunological response in patients following multiple subcutaneous injections of the mixture of polypeptides of the invention. The study lasts one year or more and includes male and female subjects suffering from open-angle glaucoma who meet criteria for high risk to progress. The subject receives placebo or the mixture of polypeptides of the invention (5, 15, 30 or 50 mg) in either weekly or monthly subcutaneous injections. Subjects attend the study sites periodically for safety, immunological and efficacy (functional and structural) evaluations throughout the entire study period.

Results

Patients treated with the mixture of polypeptides of the invention exhibit an increase in immunological response to the mixture of polypeptides of the invention as compared to the group receiving the placebo. Additionally, the group receiving the mixture of polypeptides of the invention demonstrates increased protection against loss of RGCs and consequent reduced severity of glaucoma symptoms, e.g. reduced atrophy of the optic nerve, as compared to the group receiving the placebo. The patients receiving the mixture of polypeptides of the invention also demonstrate reduced visual field loss and increased preservation of the retina and of the structural integrity of the optic nerve.

Multiple Sclerosis Clinical

The clinical trials of the mixture of polypeptides of the invention for MS are open-label pilot studies designed to evaluate the efficacy, tolerability and safety of once-weekly subcutaneous injections of the mixture of polypeptides of the invention (15 mg or 30 mg) in relapsing-remitting MS patients (n=25 patients per study). Magnetic resonance imaging (MRI) studies provide the strongest evidence for a neuroprotective effect in MS patients. The effect of the mixture of polypeptides of the invention is evaluated by the change from baseline in the total number of $T_1$ gadolinium-enhancing lesions. The immunological response to the mixture of polypeptides of the invention is evaluated.

A number of different strengths of the mixture of polypeptides of the invention have been developed. The complete composition of a single prefilled syringe of 15 mg or 30 mg of the mixture of polypeptides of the invention are presented in Table 13.

TABLE 13

Composition of Two Strengths of the mixture of polypeptides of the invention in a Prefilled Syringe

| Ingredient | Strength of the mixture of polypeptides of the invention | | Function |
| --- | --- | --- | --- |
| | 15 mg | 30 mg | |
| The mixture of polypeptides of the invention (mg) | 15 | 30 | Active Substance |
| Mannitol (mg) | 45.0 | 40.0 | Excipient (Bulking Agent) |
| Water for injections | q.s. to 1.0 ml | q.s. to 1.0 ml | Solvent |

The storage conditions for the prefilled syringes of the mixture of polypeptides of the invention were refrigeration (2° to 8° C./36° to 46° F.). However, excursions from recommended storage conditions to room temperature conditions (15° to 30° C./59° to 86° F.) for up to one week were shown to have no adverse impact on the product.

Two Phase II, open-label pilot studies in RR-MS patients are presently ongoing. These studies are designed to evaluate the efficacy, tolerability, safety and immunogenicity of once weekly sc injections of the polypeptide mixture of the invention (15 mg or 30 mg) in MS patients. Specifically, the studies evaluate once-weekly injections of the polypeptide mixture of the invention on MRI disease activity as reflected by the total number of T1 gadolinium [Gd]-enhancing lesions and new T2 lesions; and to evaluate the tolerability and safety of the polypeptide mixture of the invention in subjects with R-RMS.

Polypeptide Mixture of the Invention (15 Mg)

Thirty-eight (38) subjects [29 (76.3%) females] were enrolled in this study. The mean age is 33.8 years (range 20-48); all, besides one subject, are Caucasians. Mean body mass index (BMI) is 23 (range 17-24), mean MS duration is 4.7 years (range 0.2-20.6). According to the CRF database, 37 subjects are still ongoing; one subject prematurely discontinued due to adverse event. The mean treatment duration since the first study drug injection is 71.7 days (range 29-108).

Polypeptide Mixture of the Invention (30 Mg)

Twenty-seven (27) subjects [18 (66.7%) females] were enrolled in this study. The mean age is 33.6 years (range 18-51); all, besides one subject, are Caucasians. Mean BMI is 23.3 (range 17-34), mean MS duration is 2.4 years (range 0.2-13.6). According to the CRF database, 25 subjects are still ongoing; two subjects prematurely discontinued due to adverse event. The mean treatment duration since the first study drug injection is 52.1 days (range 1-90).

Results

Patients treated with the mixture of polypeptides of the invention exhibit a change in immunological response to glatiramer acetate/or high molecular weight glatiramer acetate as compared to the group receiving the placebo. Patients treated with the mixture of polypeptides of the invention have reduced the proportion of re-enhancing lesions and new MS lesions evolving into "black holes" as compared to the group receiving the placebo, suggesting a global central mechanism of action and a potential neuroprotective effect. Thus the mixture of polypeptides of the invention has a beneficial clinical effect in the long term, since axonal degeneration is believed to cause irreversible chronic damage in MS.

| | |
| --- | --- |
| Design | Subjects are evaluated at study sites at ten scheduled visits: weeks −10 (screening), −6, 0 (baseline); one week post baseline (visit 1); and at weeks 4, 12, 24, 28, 32 and 36 (termination). Following the pre-treatment evaluations at weeks −10 (screening), −6 and 0 (baseline), eligible subjects are enrolled and receive once-weekly injections of the polypeptide mixture of the invention for a period of 36 weeks. Subjects undergo 3 pre-treatment MRI scans as follows: week −10 (screening), week −6 and 14-18 days prior to the week 0 (baseline) visit; and 4 on-treatment MRI scans at weeks 12, 28, 32 and 36 (termination). |
| Outcome Measures | Primary Efficacy Endpoint<br><br>Change in the sum of T1 Gd-enhancing lesions measured at pre-treatment (weeks −10 [screening]; −6; and 14-18 days prior to week 0 [baseline]) to the sum of T1 Gd-enhancing lesions measured in the last study trimester (weeks 28, 32 and 36 [termination]).<br>Secondary Efficacy Endpoint<br><br>Change in the sum of new T2 lesions from pre-treatment (weeks −6 and 0 [baseline]) to the sum of new T2 lesions in the last 2 treatment visits (weeks 32 and 36 [termination]).<br>Safety Outcome Measures<br><br>Incidence, frequency and severity of Adverse Events (AEs); Changes in vital signs, ECG and routine clinical laboratory parameters |
| Exploratory Analysis | The following tests are performed on peripheral blood lymphocytes (PBL): Proliferation response. Elispot for the detection of IL-4, IL-5, IL-10 and IFN-γ secreting cells. Cytokines secretion as determined by ELISA: IL-4, IL-5, IL-10 and IFN-γ. Serum samples are collected for testing anti-GA antibodies (total Ig, IgG1, IgG2, IgM and IgE). |

What is claimed is:

1. A composition comprising a mixture of polypeptides, wherein each polypeptide (a) is a copolymer of the amino acids L-glutamic acid, L-alanine, L-tyrosine, and L-lysine, and (b) may be in the form of a pharmaceutically acceptable salt; and wherein in the mixture (i) the polypeptides have an average molecular weight in the range 13,500 to 18,500 daltons, (ii) 13% to 38% of the polypeptides have a diethylamide group instead of a carboxyl group present at one end thereof, and (iii) 68% of the polypeptides have a molecular weight between 7,000 and 41,000 daltons.

2. The composition of claim 1, wherein the average molecular weight is 16,000 daltons.

3. The composition of claim 1, wherein the amino acids are present in the mixture in an amount such that the average molar fraction of the amino acids is: L-glutamic acid 0.129-0.153; L-alanine 0.392-0.462; L-tyrosine 0.086-0.100; and L-lysine 0.300-0.374.

4. The composition of claim 3, wherein the amino acids are present in the mixture in an amount such that the average molar fraction of the amino acids is: L-glutamic acid 0.141; L-alanine 0.427; L-tyrosine 0.095; and L-lysine 0.338.

5. The composition of claim 1, wherein 19% to 28% of the polypeptides in the mixture have diethylamide at one end thereof.

6. The composition of claim 5, wherein the remainder of polypeptides in the mixture have a carboxyl group at the C-terminus.

7. The composition of claim 1, wherein 35-45% of the polypeptides in the mixture have a L-alanine at the N-terminus.

8. The composition of claim 1, wherein less than 5% of the polypeptides in the mixture have a molecular weight below 4,700 daltons.

9. The composition of claim 8, wherein less than 3% of the polypeptides in the mixture have a molecular weight below 4,700 daltons.

10. The composition of claim 1, wherein the mixture of polypeptides has a circular dichroism value of 0.91.

11. The composition of claim 1, wherein the polypeptides are in the form of a pharmaceutically acceptable salt.

12. The composition of claim 11, wherein the pharmaceutically acceptable salt is an organic salt.

13. The composition of claim 12, wherein the organic salt is an acid addition salt.

14. The composition of claim 13, wherein the acid addition salt is an acetate salt.

15. The composition of claim 11, wherein the pharmaceutically acceptable salt is a chloride salt.

16. The composition of claim 1, further characterized by having at least 90% suppressive activity in an EAE blocking test when administered at a dose of 100 µg/mouse of the polypeptide mixture.

17. The composition of claim 1, wherein the composition is lyophilized.

18. A pharmaceutical composition comprising a therapeutically effective amount of the composition of claim 1 and a pharmaceutically acceptable carrier.

19. The pharmaceutical composition of claim 18, wherein the pharmaceutically acceptable carrier comprises mannitol.

20. The pharmaceutical composition of claim 18, wherein the pharmaceutically acceptable carrier is a liposome.

21. The pharmaceutical composition of claim 18, wherein the pharmaceutical composition further comprises an adjuvant.

22. The pharmaceutical composition of claim 21, wherein the adjuvant is selected from the group consisting of alum, a phospholipid, a DNA adjuvant, complete Freund's adjuvant, and incomplete Freund's adjuvant.

23. The pharmaceutical composition of claim 22, wherein the adjuvant is a phospholipid.

24. The pharmaceutical composition of claim 18, wherein the polypeptide mixture is in a nanoparticle.

25. The pharmaceutical composition of claim 18, wherein the polypeptide mixture is attached to a nanoparticle.

26. The pharmaceutical composition of claim 25, wherein the polypeptide mixture is attached electrostatically to the nanoparticle.

27. The pharmaceutical composition of claim 18, wherein the effective amount is 0.1 mg to 70 mg.

28. The pharmaceutical composition of claim 27, wherein the effective amount is 1 mg.

29. The pharmaceutical composition of claim 27, wherein the effective amount is 5 mg.

30. The pharmaceutical composition of claim 27, wherein the effective amount is 15 mg.

31. The pharmaceutical composition of claim 27, wherein the effective amount is 20 mg.

32. The pharmaceutical composition of claim 27, wherein the effective amount is 30 mg.

33. The pharmaceutical composition of claim 27, wherein the effective amount is 50 mg.

34. The pharmaceutical composition of claim 18, wherein the composition has a pH between 5.5 and 9.0.

35. The pharmaceutical composition of claim 34, wherein the pH is between 5.5 and 8.5.

36. The pharmaceutical composition of claim 35, wherein the pH is between 5.5 and 6.

37. The pharmaceutical composition of claim 18, further comprising at least one of riluzole, glatiramer acetate, baclofen, phenytoin, quinine, amitriptyline, phenothiazine, chlorpromazine, butyrophenone neuroleptics, geldanamycin, trehalose, cystamine, rapamycin, glucocorticoid, nonsteroidal anti-inflammatory drug, minocycline, folic acid, creatine, dichloroacetate, nicotinamide, riboflavin, carnitine, tauroursodeoxycholic acid, ginko biloba, coenzyme Q10, vitamin A, vitamin C, vitamin E, selenium, lipoic acid, arginine, mithramycin, remacemide, filuzole, lamotrigine, memantine, gabamentin, HDAC inhibitors, retinoic acid, reserpine, anticholinergics, diphenoxylate, loperamide, deodorized opium tincture, codeine, metronidazole, sulfasalazine, corticosteroid, azathioprine, 6-mercaptopurine, cyclosporine, 4-amino quinolines, loperamide, 5-aminosalicylic acid (5-ASA), balsalazide, olsalazine, ACTH 75, ACTH 120, antibiotic, pilocarpine, isoptocarpine timolol hemihydrate, timolol maleate, betaxolol, levobunolol, carteolol, metipranolol, epinephrine, dipivefrin, carbachol, apraclonidine, brimonidine, dorzolamide, latanoprost, travaprost, brimatoprost, brinzolamide, cholinesterase inhibitor, demecarium, isoblurophate, carbonic anhydrase inhibitor, mannitol, oral glycerin, mydriatics, memantine, atropine, meclizine, dienhydrinate, prochiorperazine, scopolamine, diphenhydramine, clonazepam, gabapentin, primidone, botulinum toxin, actazolamide cabidopa-levodopa, isoniazid, diazepam, clonazepam, dantrolene sodium, tizanidine, clonidine, sildenafil, aiprostadil, papaverine, bisacodyl, magnesium hydroxide, glycerin, psyllium hydrophilic mucilloid, sodium phosphate, anti-tumor necrosis factor (TNF), docusate, oxybutynin, desmopressin, vasopressin, tolterodine, carbamazepine, imipramine, bethane, phenoxybenzamine, terazosin, propantheline, oxybutonin, hyoscyamine, methenamine, nitrofurantoin, phenazopyridine, ciprofloxacin, amantadine, pemoline, vitamin D derivative, modafinil, fluoxetine, sertraline, venlafaxine, citalopram, parocetine, trazodone, nortriptyline, imipramine, dothiepin, lofepramine, doxepin, protriptyline, tranylcypromine, moclobemide, bupropion, nefazodone, mirtazapine, zolpidem, alprazolam, temazepam, buspirone, gabatentin, topiramate, zonisamide, desipramine, imipramine, doxepin, protriptyline, pentozifylline, hydroxyzine, natalizumab, steroids, muscle relaxants, prednisolone, dexamethasone, corticotrophin, immunosuppressants, acyclovir, azathioprine, cyclophosphamide, mitoxantrone, methotrexate, cladribine, interferons, laquinimod, alemtuzumab, 4-aminopyridine, 3,4-diaminopyridine, eliprodil, IV immunoglobin, pregabalin, or ziconotide.

38. The pharmaceutical composition of claim 18, wherein the composition is lyophilized.

39. A process for preparing a pharmaceutical composition comprising combining a therapeutically effective amount of the composition of claim 1 with a pharmaceutically acceptable carrier.

40. A method of treating a human subject afflicted with a neurodegenerative disease comprising administering to the human subject a therapeutically effective amount of the composition of claim 1 as to thereby treat the human subject.

41. A method of alleviating a symptom of an neurodegenerative disease comprising administering to the human subject the composition of claim 1 in an amount effective to alleviate the symptom.

42. A method of treating a human subject afflicted with an inflammatory bowel disease comprising administering to the human subject a therapeutically effective amount of the composition of claim 1 so as to treat of the inflammatory bowel disease.

43. A method of alleviating a symptom of an inflammatory bowel disease comprising administering to the human subject the composition of claim 1 in an amount effective to alleviate the symptom.

* * * * *